US009068019B2

(12) United States Patent
Kim et al.

(10) Patent No.: US 9,068,019 B2
(45) **Date of Patent: *Jun. 30, 2015**

(54) MODIFIED HUMAN TUMOR NECROSIS FACTOR RECEPTOR-1 POLYPEPTIDE OR FRAGMENT THEREOF, AND METHOD FOR PREPARING SAME

(75) Inventors: Sung Wuk Kim, Seongnam-si (KR); Sung Soo Jun, Seongnam-si (KR); Seung Kook Park, Seoul (KR); Song Young Kim, Suwon-si (KR); Eun Sun Kim, Suwon-si (KR); Jae Kap Jeong, Suwon-si (KR); Ha Na Kim, Suwon-si (KR); Yeon Jung Song, Yongin-si (KR)

(73) Assignee: HANALL BIOPHARMA CO., LTD., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/502,675

(22) PCT Filed: Oct. 19, 2010

(86) PCT No.: PCT/KR2010/007160

§ 371 (c)(1), (2), (4) Date: Jun. 21, 2012

(87) PCT Pub. No.: WO2011/049350

PCT Pub. Date: Apr. 28, 2011

(65) Prior Publication Data

US 2012/0251486 A1 Oct. 4, 2012

(30) Foreign Application Priority Data

Oct. 19, 2009 (KR) ........................ 10-2009-0099219

(51) Int. Cl.

| | |
|---|---|
| ***A61K 38/19*** | (2006.01) |
| ***C12N 1/21*** | (2006.01) |
| ***C07K 14/525*** | (2006.01) |
| ***C07K 14/705*** | (2006.01) |

(52) U.S. Cl.

CPC ................................ *C07K 14/70578* (2013.01)

(58) Field of Classification Search

None

See application file for complete search history.

(56) References Cited

U.S. PATENT DOCUMENTS

| | | | | |
|---|---|---|---|---|
| 5,665,859 | A * | 9/1997 | Wallach et al. | 530/328 |
| 6,419,919 | B2 * | 7/2002 | Mountz et al. | 424/93.2 |
| 7,745,579 | B1 | 6/2010 | Wallach et al. | |
| 8,097,704 | B2 | 1/2012 | Kim et al. | |
| 2002/0090676 | A1 * | 7/2002 | Hauptmann et al. | 435/69.1 |

FOREIGN PATENT DOCUMENTS

| | | | |
|---|---|---|---|
| KR | 10-2006-0092292 | B1 | 8/2006 |
| KR | 10-0748293 | B1 | 8/2007 |
| KR | 10-0804126 | B1 | 2/2008 |
| KR | 10-0847010 | B1 | 7/2008 |
| WO | WO 9941374 | A2 * | 8/1999 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Wong et al (Clin Immunol. Feb. 2008: 126(2); 121-136).*
Gores et al (FASEB J. Jun. 2009;23(6):1625-37).*
Gomez-Gallego et al (Eur Neurol 2008; 59: 91-93).*
JR Bradley, "TNF-Mediated Inflammatory Disease," Journal of Pathology, 2008, vol. 214, pp. 149-160.
John D. Carter, "Treatment of Relapsing Polychondritis with a TNF Antagonist," Journal of Rheumatology, 2005, vol. 32, No. 7, pp. 1411-1414.
A Edrees, "Successful Use of Etanercept for the Treatment of Reiter's Syndrome: a Case Report and Review of the Literature," http://www.ncbi.nlm.nih.gov/pubmed/21785961, Jul. 24, 2013, 1 page.
"Treatment of Longstanding Active Giant Cell Arteritis with Infliximab: Report of Four Cases," Concise Communications, pp. 2933-2935, 2001.
Kammoun-Krichen et al., "A Potential Role of TNFR Gene Polymorphisms in Autoimmune Thyroid Diseases in the Tunisian Population," http://www.ncbi.nlm.nih.gov/pubmed/18571427, Jul. 24, 2013, 1 page.
Koulmanda et al., "The Role of TNF-α in Mice with Type 1- and 2-Diabetes," http://www.plosone.org/article/info:doi/10.1371/journal.pone.0033254, Jul. 8, 2013, 9 pages.
Mazza et al., "Innovative Uses of Tumor Necrosis Factor a Inhibitors," Dermatol. Clin., 2010, vol. 28, pp. 559-575.
Moss et al., "TNF-a and Chronic Fatigue Syndrome," Journal of Clinical Immunology, 1999, vol. 19, No. 5, pp. 314-315.
Opree et al., "Involvement of the Proinflammatory Cytokines Tumor Necrosis Factor-a, IL-1b, and IL-6 But Not IL-8 in the Development of Heat Hyperalgesia: Effects on Heat-Evoked Calcitonin Gene-Related Peptide Release from Rat Skin," Society for Neuroscience, 2000, pp. 6289-6293.
Perides et al., "Immunology: TNF-α-dependent Regulation of Acute Pancreatitis Severity by Ly-6Chi Monocytes in Mice," The Journal of Biological Chemistry, 2011, pp. 13327-13335.
"http://journal.publications.chestnet.org/," Chest, 2001, vol. 120, No. 1, pp. 2S-3S.

(Continued)

*Primary Examiner* — Brian J Gangle
*Assistant Examiner* — Andrea McCollum
(74) *Attorney, Agent, or Firm* — Sughrue Mion, PLLC

(57) ABSTRACT

The present invention relates to a modified human tumor necrosis factor receptor-1 polypeptide to be coupled to a tumor necrosis factor in vivo or ex vivo, or to a fragment thereof. The modified human tumor necrosis factor receptor-1 polypeptide or the fragment thereof according to the present invention exhibit improved resistance against in vivo protease activity, and thus exhibit improved bioavailability and an improved absorption rate.

8 Claims, 9 Drawing Sheets

(56) References Cited

OTHER PUBLICATIONS

Ramos-Casals et al., "A Systematic Review of the Off-Label Use of Biological Therapies in Systemic Autoimmune Diseases," Medicine, 2008, vol. 87, No. 6, pp. 345-364.

Sugihara et al., "Interleukin-1 and Tumor Necrosis Factor a Blockade Treatment of Experiment," Arthritis Rheum, 2012, vol. 64, No. 8, 1 page.

Titelbaum et al., "Anti-Tumor Necrosis Factor Alpha-Associated Multiple Sclerosis," American Society of Neuroradiology, 2005, vol. 26, pp. 1548-1550.

Van Horssen, "TNF-α in Cancer Treatment: Molecular Insights, Antitumor Effects, and Clinical Utility," The Oncologist, 2006, vol. 11, pp. 397-408.

* cited by examiner

MODIFIED HUMAN TUMOR NECROSIS FACTOR RECEPTOR-1 POLYPEPTIDE OR FRAGMENT THEREOF, AND METHOD FOR PREPARING SAME

CROSS REFERENCE TO RELATED APPLICATIONS

This application is a National Stage of International Application No. PCT/KR2010/007160 filed on Oct. 19, 2010, which claims priority from Korean Patent Application No. 10-2009-0099219, filed on Oct. 19, 2009, the contents of all of which are incorporated herein by reference in their entirety.

TECHNICAL FIELD

The present invention relates to a modified human tumor necrosis factor receptor-I polypeptide or a fragment thereof which is capable of binding to a tumor necrosis factor in vivo or ex vivo and a method for producing the same.

BACKGROUND ART

Inflammation is the body's defense response which is induced by antigenic stimulation. An inflammatory response may worsen pathologically when inflammation takes place even after the removal of infectious antigenic substances or an inflammatory response is induced by an inappropriate stimulus such as an auto-antigen. Such an inflammatory response involves a variety of cytokines. In particular, as a cytokine which serves to control inflammation, a tumor necrosis factor (hereinafter, referred to as "TNF") was identified.

TNF was originally discovered as a protein which eliminates tumor cells (Carswell et al., PNAS 72:3666-3670, 1975; Old et al., Science 230: 630-632, 1985; and Beutler et al., Nature 316:552-554, 1985). TNF is a class of cytokines produced by numerous cell types, including monocytes and macrophages, and is directly involved in inflammatory responses. At least two TNFs (TNF-α and TNF-β) have been previously described, and each is active as a trimeric molecule and is believed to initiate intracellular signaling by crosslinking receptors (Engelmann et al., J. Biol. Chem., 265:14497-14504). TNFs induce inflammatory responses in vivo to regulate cell-mediated immune responses and defense mechanisms and have important physiological effects on a number of different target cells (Selby et al., Lancep 1:483, 1988; Starnes et al., J. Clin. Invest 82:1321, 1988; Oliff et al., Cell 50; 555, 1987; Waage et al., Lancept 1:355, 1987; and Aggarwal et al., Nat. Rev. Immunol. 3:745-756, 2003). However, it was demonstrated that an excess of TNFs results in a pathological condition such as rheumatoid arthritis, degenerative arthritis, psoriasis or Crohn's disease, and suppression of TNFs exhibits therapeutic effects on the diseases (Feldmann et al., Nat. Med. 9:1245-1250, 2003; Kooloos et al., Drug Discov. Today 12:125-131, 2007; Rutgeerts et al., Gastroenterology 126:1593-1610, 2004; Rothe et al., Nature 364:798-802, 1993; Kafrouni et al., J. Leukocyte Biol. 74:564-571, 2003; Rahman et al., Plos Pathog. 2:e4, 2006; Chan et al., J. Biol. Chem. 278:51613-61621, 2003; and Wajant et al., Cell Death Differ. 10:45-65, 2003).

Tumor necrosis factor receptor (hereinafter, referred to as "TNFR") is a cytokine receptor which binds to TNF.

Two types of TNFRs, known as p55-TNFRI and p75-TNFRII, have been currently discovered. Expression of TNFRI can be demonstrated in almost every mammalian cell while TNFRII expression is largely limited to cells of the immune system and endothelial cells.

The two TNF receptors exhibit 28% amino acid sequence similarity therebetween. Both receptors have an extracellular domain and have four cysteine-rich domains.

The cytoplasmic portion of TNFRI contains a "death domain" which initiates apoptotic signaling. TNFRII has no death domain and the function thereof has not been yet clearly defined. In addition, TNFRI and TNFRII exhibit a difference in terms of affinity for TNF-α which is a ligand. It is known that TNFRI exhibits an affinity 30 times or higher than that of TNFRII (Tartaglia et al., J. Biol. Chem. 268:18542-18548, 1993; and Bernard et al., Cytokine 7:759-770, 1995). Due to such affinity difference, a variety of attempts have been made for the development of pharmaceuticals regarding TNFRI.

TNFR adhering to the cell surface is cleaved by protease to produce soluble TNFR. The soluble TNFR neutralizes an excess of TNF to control the level of TNF. In cases such as autoimmune disease and chronic inflammation excessively high levels of TNF overwhelms the ability to self-regulate.

In order to artificially control TNF signaling, various strategies of blocking TNF have been attempted including inhibition of TNF synthesis, inhibition of TNF secretion or shedding, and inhibition of TNF signaling. Among TNF blocking methods, a method of blocking TNF signaling by preventing binding of TNFR to TNF has been applied for the development of pharmaceuticals. For example, etanercept, which is prepared by fusing a TNFRII extracellular region to the Fc region of an antibody, and antibodies capable of binding to TNF, adalimumab and infliximab have been used globally as a therapeutic agent for treating rheumatoid arthritis, psoriasis, ankylosing spondylitis, or the like.

Lenercept, which is a fusion protein of an antibody Fc to a TNFRI extracellular domain produced by applying the same technique as in the anti-rheumatoid arthritis drug etanercept, has completed a phase II clinical trial in Europe and USA (Furst et al., J. Rheumatol. 30:2123-2126, 2003; and Rau et al., J Rheumatol. 30:680-690, 2003 Arbraham et al., Crit. Care Med. 29:503-510, 2001). In addition, research has been carried out for a TNFRI dimer and a pegylated soluble TNFRI molecule (Carl et al., Ann. Rheum. Dis. 58:173-181, 1999; Solorzano et al., J. Appl. Physiol. 84:1119-1130, 1998; Carl et al., Advanced Drug Delivery Reviews 55:1315-1336, 2003; Honghui et al., J. Clin. Pharmacol. 45:490-497, 2005; and Yugal et al., The American Journal of Pathology 172: 1411-1418, 2008).

Further, as an approach to reduce immunogenicity of TNFRI and increase the ability of TNFRI to bind with TNF, modification of amino acid sequences has been studied. In particular, a TNFRI mutant, against which the occurrence of an antibody has been decreased through partial substitution of the amino acid sequence of TNFRI, and a TNFRI mutant, which has an increased ability of TNFRI to bind with TNF, are known (U.S. Pat. No. 7,144,987).

Research has been actively made to find an active site responsible for binding of TNFR to TNF, and it is known that the fourth domain of TNFR is not essential for binding with TNF, and when deletion of the second and third domains results in loss of TNF binding activity (Corcoran et al., Eur. J. Biochem. 233:831-840, 1994; Chin-Hsuch et al., J. Biol. Chem. 270:2874-2878, 1995; and Scallon et al., Cytokine 7:759-770, 1995). Further, a certain region of the third domain for binding of TNFRI to TNF may be made deficient, and the amino acid sequence consisting of amino acid residues 59 to 143 of a human TNFRI polypeptide (SEQ ID NO: 1) is known to be a region showing a biological activity of TNFRI (U.S. Pat. No. 6,989,147).

Therefore, since binding of TNFRI to TNF is made in this region, other regions may include considerable added groups, eliminated groups or substituted groups.

Meanwhile, in order to enhance bioavailability, TFNRI is used in the form of a TNFRI polypeptide fragment rather than full-length TNFRI. For the purpose of producing an effective injection and oral formulation capable of minimizing protease cleavability and enhancing cellular permeability, TFNRI needs to be prepared as small in size as possible.

In addition, since protein therapeutics are cleared by general processes such as metabolism during in vivo circulation, glomerular filtration, and action of proteases in gastrointestinal tracts, tissues and blood, there is difficulty in delivery of a protein therapeutic to a target site while retaining an intrinsic activity of the protein in vivo. In particular, clearance of a drug by protease has significant effects on a half-life of a protein therapeutic upon administration thereof via oral administration, vascular injection, intramuscular injection, or the like.

A human tumor necrosis factor inhibitor, which is one of protein therapeutic drugs and controls in vivo TNF, has been developed in the form of an injection, but the administration of an injection has problems associated with pain and risk of infection. Therefore, another approach is required such as reduction of injection frequency or oral administration. Enhancement of stability of a human tumor necrosis factor inhibitor is essential for this purpose, but protease-induced degradation constitutes a great obstacle thereto.

Accordingly, an important goal of the development of an orally administrable protein therapeutic is to develop a protein therapeutic exhibiting protease resistance while having biological activity.

DISCLOSURE OF THE INVENTION

Technical Problem

Therefore, the present invention is intended to provide a modified human tumor necrosis factor receptor-I (TNFRI) polypeptide or a fragment thereof, which has a TNF inhibitory activity in vivo or ex vivo and exhibits improved resistance to protease present in the gastrointestinal tract, cytoplasm and blood.

Technical Solution

Unless stated otherwise, all technical and scientific terms used in the specification, examples and appended claims have the meanings defined below.

As used herein, the term “human tumor necrosis factor receptor-I” or “human tumor necrosis factor receptor-I polypeptide” (hereinafter, referred to as “TNFRI” or “TNFRI polypeptide”) refers to a polypeptide consisting of 455 amino acids derived from a human and capable of binding to TNF.

As used herein, the term “human tumor necrosis factor receptor-I fragment” or “human tumor necrosis factor receptor-I polypeptide fragment” (hereinafter, referred to as “TNFRI fragment” or “TNFRI polypeptide fragment”) refers to a fragment of TNFRI which has an amino acid sequence 100% identical to a corresponding amino acid sequence of TNFRI and which shows a deletion of at least one amino acid residue of the TNFRI. The deleted amino acid residue(s) may be located at any position of the polypeptide, such as the N-terminus, the C-terminus, or in between these. The fragment shares at least one biological property with full-length TNFRI. Representative is a fragment consisting of a 108- or 126-amino acid sequence extending from amino acid residue 41 of the N-terminus of TNFRI, each being designated as TNFRI108 or TNFRI126 herein.

As used herein, the term “TNFRI variant” or “TNFRI mutant” or “TNFRI fragment variant”, “TNFRI fragment mutant” or “modified TNFRI polypeptide”, or “modified TNFRI polypeptide fragment” refers to a TNFRI polypeptide or a fragment thereof which shares a sequence identity of less than 100% with the TNFRI polypeptide or a fragment thereof isolated from the native or recombinant cells as defined below. Typically, the TNFRI variant has an amino acid sequence identity of approximately 70% or higher with a wild-type or native TNFRI or TNFRI fragment. The sequence identity is preferably at least approximately 75%, more preferably at least approximately 80%, still more preferably at least approximately 85%, even more preferably at least approximately 90%, and most preferably at least approximately 95%.

As used herein, the term “single variant” refers to a variant with a mutation at one position in the amino acid sequence of a human tumor necrosis factor receptor-I or human tumor necrosis factor receptor-I fragment.

As used herein, the term “double variant” refers to a variant with a mutation at two positions in the amino acid sequence of a human tumor necrosis factor receptor-I or human tumor necrosis factor receptor-I fragment.

As used herein, the term “triple variant” refers to a variant with a mutation at three positions in the amino acid sequence of a human tumor necrosis factor receptor-I or human tumor necrosis factor receptor-I fragment.

As used herein, the term “TNFRIm” refers to a TNFRI fragment having an amino acid sequence consisting of an m number of amino acids extending from amino acid residue 41 of the N-terminus of the amino acid sequence of TNFRI. For example, the TNFRI108 fragment refers to a TNFRI fragment having a 108-amino acid sequence extending from amino acid residue 41 of the TNFRI N-terminus. Another example is TNFRI126 that has a 126-amino acid sequence extending from amino acid residue 41 of the TNFRI N-terminus.

As used herein, the term “Met-TNFRIm” refers to a TNFRI fragment having an amino acid sequence consisting of an m number of amino acids extending from amino acid residue 41 of the TNFRI N-terminus in which methionine originally absent in TNFRI amino acid sequence has been added to the N-terminus for the purpose of expression of TNFRI in *E. coli.*

The symbol “xAz,” as used herein refers to the substitution of amino acid x at position A with amino acid z in the amino acid sequence. For example, K48Q refers to a glutamine (Gln) residue substituted for a lysine (Lys) residue at position 48.

The present invention relates to a modified TNFRI polypeptide or a fragment thereof having a TNF inhibitory activity in vivo and/or ex vivo and improved protease resistance, a method for producing the same, and use thereof.

As a result of extensive and intensive studies to develop a TNFRI variant having increased stability in vivo and/or ex vivo, the inventors of the present application have constructed a TNFRI variant having increased protease resistance, by substituting one or more amino acid residues of the amino acid sequence of a native TNFRI fragment which are anticipated to be recognized and cleaved by proteases with one or more amino acid residues which are neither recognized nor cleaved by proteases and which do not significantly change physicochemical properties.

Therefore, the present invention provides a modified TNFRI polypeptide or a fragment thereof having improved protease resistance through the amino acid modifications at one or more specific positions of an amino acid sequence of a native TNFRI polypeptide or a fragment thereof.

The modified TNFRI polypeptide or a fragment thereof in accordance with the present invention has excellent pharmaceutical bioavailability and exhibits an activity even without containing sugar chains, and therefore may be easily produced in microbial cells as well as animal cells.

More specifically, the present invention will be reviewed hereinafter.

The present invention provides a modified TNFRI polypeptide or a fragment thereof containing amino acid modifications at one or more positions selected from the group consisting of positions 61, 68, 78, 85, 106, 107, 109, 121, 128, 133, 135, 136, 138, 141, 150, 156, 161, 200, 203, 206 and 207 in the amino acid sequence of a native human TNFRI polypeptide as set forth in SEQ ID NO: 1 or a fragment thereof; more preferably one or more positions selected from the group consisting of positions 68, 85, 109, 128, 133, 135, 136, 141 and 161; and most preferably one or more positions selected from the group consisting of positions 68, 109, 133, 135, 136, 141 and 161.

Amino acid modifications at the above-specified positions are modifications to have increased protease resistance as compared to an unmodified TNFRI polypeptide or a fragment thereof, and include not only substitutions of amino acids but also additional chemical modifications of amino acids at the above-specified positions, such as post-translational modifications of a protein, for example, glycosylation by a carbohydrate moiety, acylation (e.g., acetylation or succinylation), methylation, phosphorylation, hesylation, carbamylation, sulfation, prenylation, oxidation, guanidination, amidination, carbamylation (e.g., carbamoylation), trinitrophenylation, nitration, and PEGylation. The modified TNFRI polypeptide or a fragment thereof in accordance with the present invention exhibits increased resistance against in vivo proteases by the amino acid modifications at the above-specified positions. The chemical modifications may be carried out by manipulation of amino acids according to a conventional method known in the art.

The present invention provides a modified TNFRI polypeptide or a fragment thereof containing amino acid substitutions at one or more positions selected from the group consisting of positions 61, 68, 78, 85, 106, 107, 109, 121, 128, 133, 135, 136, 138, 141, 150, 156, 161, 200, 203, 206 and 207 in the amino acid sequence of a native human TNFRI polypeptide as set forth in SEQ ID NO: 1 or a fragment thereof.

Preferably, the present invention provides a modified TNFRI polypeptide or a fragment thereof containing amino acid substitutions at one or more positions selected from the group consisting of positions 68, 85, 109, 128, 133, 135, 136, 141 and 161 in the amino acid sequence of a native human TNFRI polypeptide as set forth in SEQ ID NO: 1 or a fragment thereof, and more preferably one or more positions selected from the group consisting of positions 68, 109, 133, 135, 136, 141 and 161.

The amino acid substitutions at positions 61, 68, 78, 85, 106, 107, 109, 121, 128, 133, 135, 136, 138, 141, 150, 156, 161, 200, 203, 206 and 207 in the amino acid sequence of a native human TNFRI polypeptide as set forth in SEQ ID NO: 1 or a fragment thereof are substitutions of original amino acid residues with amino acid residues which are neither recognized nor cleaved by proteases and which do not significantly change physicochemical properties, and preferably includes substitutions of R(Arg) with Q(Gln) or H(His); E(Glu) with Q(Gln) or N(Asn); K(Lys) with Q(Gln) or N(Asn); D(Asp) with N(Asn) or Q(Gln); M(Met) with I(Ile) or V(Val); P(Pro) with A(Ala) or S(Ser); Y(Tyr) with I(Ile) or H(His); F(Phe) with I(Ile) or V(Val); W(Trp) with H(His) or S(Ser); and L(Lue) with I(Ile) or V(Val).

Further, the present invention provides a modified TNFRI polypeptide or a fragment thereof containing one or more amino acid substitutions selected from the group consisting of K61Q, K61N, L68I, L68V, D78Q, E85N, R106H, R106Q, K107Q, M1091, R121H, R121Q, R128H, R128Q, R133Q, Y135I, Y135H, W136H, W136S, E138Q, E138N, F141I, F141V, L150I, L1561, K161Q, K161N, E200Q, K203Q, E206Q, D207Q and D207N in the amino acid sequence of a native human TNFRI polypeptide as set forth in SEQ ID NO: 1 or a fragment thereof.

Preferably, the present invention provides a modified TNFRI polypeptide or a fragment thereof containing one or more amino acid substitutions selected from the group consisting of L68I, L68V, E85N, M1091, R128H, R133Q, Y135I, W136S, F141I, F141V, K161Q and K161N in the amino acid sequence of a native human TNFRI polypeptide as set forth in SEQ ID NO: 1 or a fragment thereof, more preferably one or more amino acid substitutions selected from the group consisting of L68I, L68V, M1091, R133Q, Y135I, W136S, F141I, F141V, K161Q and K161N, and still further preferably one or more amino acid substitutions selected from the group consisting of L68I, L68V, R133Q, Y135I, F141I, K161Q and K161N.

Preferably, the present invention provides a modified TNFRI polypeptide or a fragment thereof containing one or two amino acid modifications as mentioned above.

Namely, the present invention provides a modified TNFRI polypeptide or a fragment thereof containing one or two amino acid substitutions selected from the group consisting of K61Q, K61N, L68I, L68V, D78Q, E85N, R106H, R106Q, K107Q, M1091, R121H, R121Q, R128H, R128Q, R133Q, Y135I, Y135H, W136H, W136S, E138Q, E138N, F141I, F141V, L150I, L1561, K161Q, K161N, E200Q, K203Q, E206Q, D207Q and D207N in the amino acid sequence of a native human TNFRI polypeptide as set forth in SEQ ID NO: 1 or a fragment thereof; preferably a modified TNFRI polypeptide or a fragment thereof containing one or two amino acid substitutions selected from the group consisting of L68I, L68V, E85N, M1091, R128H, R133Q, Y135I, W136S, F141I, F141V, K161Q and K161N in the amino acid sequence of a native human TNFRI polypeptide as set forth in SEQ ID NO: 1 or a fragment thereof; and further preferably a modified TNFRI polypeptide or a fragment thereof containing one or two amino acid substitutions selected from the group consisting of L68I, L68V, R133Q, Y135I, F141I, K161Q and K161N in the amino acid sequence of a native human TNFRI polypeptide as set forth in SEQ ID NO: 1 or a fragment thereof.

As a preferred embodiment of the modified TNFRI polypeptide or a fragment thereof containing two amino acid substitutions, the present invention provides a modified TNFRI polypeptide or a fragment thereof containing two amino acid substitutions selected from the group consisting of L68V, R133Q, F141V, K161Q, K161N, E200Q and D207N in the amino acid sequence of a native human TNFRI polypeptide as set forth in SEQ ID NO: 1 or a fragment thereof. More preferably, the present invention provides a modified TNFRI polypeptide or a fragment thereof containing two amino acid substitutions of L68V and one amino acid substitution selected from R133Q, F141V, K161Q, K161N, E200Q or D207N in the amino acid sequence of a native human TNFRI polypeptide as set forth in SEQ ID NO: 1 or a fragment thereof. Further preferably, the present invention provides a modified TNFRI polypeptide or a fragment thereof containing amino acid substitutions selected from L68V/K161Q, L68V/K161N or L68V/D207N in the amino acid sequence of a native human TNFRI polypeptide as set forth in SEQ ID NO: 1 or a fragment thereof.

The fragment of a native human TNFRI polypeptide as set forth in SEQ ID NO: 1 refers to a portion of a native human TNFRI polypeptide having an effect substantially equivalent to that of the native human TNFRI polypeptide. In particular, the present invention employs an amino acid sequence consisting of amino acid residues 41-211 (SEQ ID NO: 2; TNFRI171) of the amino acid sequence of native human TNFRI as set forth in SEQ ID NO: 1; an amino acid sequence consisting of amino acid residues 41-166 (SEQ ID NO: 3; TNFRI126) of the amino acid sequence of native human TNFRI as set forth in SEQ ID NO: 1; and an amino acid sequence consisting of amino acid residues 41-148 (SEQ ID NO: 4; TNFRI108) of the amino acid sequence of native human TNFRI as set forth in SEQ ID NO: 1. However, the fragment of a native human TNFRI polypeptide as set forth in SEQ ID NO: 1 in accordance with the present invention is not limited to the above-mentioned TNFRI171, TNFRI126 and TNFRI108 as long as it exhibits an effect substantially equivalent to that of a native human TNFRI polypeptide.

The term "fragment" of a modified TNFRI polypeptide refers to a portion of a modified TNFRI polypeptide which exhibits an effect substantially equivalent to that of the modified TNFRI polypeptide and can be easily produced by those skilled in the art.

Therefore, the modified TNFRI polypeptide or a fragment thereof having improved protease resistance in accordance with the present invention encompasses those illustrated below.

The present invention provides a modified human tumor necrosis factor receptor-I polypeptide or a fragment thereof (TNFRI171 variant or a fragment thereof) containing amino acid modifications at one or more positions selected from the group consisting of positions 61, 68, 78, 85, 106, 107, 109, 121, 128, 133, 135, 136, 138, 141, 150, 156, 161, 200, 203, 206 and 207 of the amino acid sequence consisting of amino acid residues 41-211 in the amino acid sequence of a native human tumor necrosis factor receptor-I as set forth in SEQ ID NO: 1; preferably amino acid modifications at one or more positions selected from the group consisting of positions 68, 85, 109, 128, 133, 135, 136, 141 and 161; and more preferably amino acid modifications at one or more positions selected from the group consisting of positions 68, 109, 133, 135, 136, 141 and 161. Here, regarding the amino acid modifications, the same as in specific modifications and preferred modifications described above shall apply to the amino acid modifications at the above-specified positions.

The present invention provides a modified human tumor necrosis factor receptor-I polypeptide or a fragment thereof (TNFRI126 variant or a fragment thereof) containing amino acid modifications at one or more positions selected from the group consisting of positions 61, 68, 78, 85, 106, 107, 109, 121, 128, 133, 135, 136, 138, 141, 150, 156 and 161 in the amino acid sequence consisting of amino acid residues 41-166 of the amino acid sequence of a native human tumor necrosis factor receptor-I as set forth in SEQ ID NO: 1; preferably amino acid modifications at one or more positions selected from the group consisting of 68, 85, 109, 128, 133, 135, 136, 141 and 161; and further preferably amino acid modifications at one or more positions selected from the group consisting of positions 68, 109, 133, 135, 136, 141 and 161. Here, regarding the amino acid modifications, the same as in specific modifications and preferred modifications described above shall apply to the amino acid modifications at the above-specified positions.

The present invention provides a modified human tumor necrosis factor receptor-I polypeptide or a fragment thereof (TNFRI108 variant or a fragment thereof) containing amino acid modifications at one or more positions selected from the group consisting of positions 61, 68, 78, 85, 106, 107, 109, 121, 128, 133, 135, 136, 138 and 141 in the amino acid sequence consisting of amino acid residues 41-148 of the amino acid sequence of a native human tumor necrosis factor receptor-I as set forth in SEQ ID NO: 1; preferably amino acid modifications at one or more positions selected from the group consisting of positions 68, 85, 109, 128, 133, 135, 136 and 141; and further preferably amino acid modifications at one or more positions selected from the group consisting of positions 68, 109, 133, 135, 136 and 141. Here, regarding the amino acid modifications, the same as in specific modifications and preferred modifications described above shall apply to the amino acid modifications at the above-specified positions.

Further, the present invention provides a modified TNFRI polypeptide or a fragment thereof containing the above-specified amino acid modifications or the corresponding modifications in the polypeptide substantially identical to a TNFRI polypeptide having the amino acid sequence as set forth in SEQ ID NO: 1. The term "polypeptide substantially identical to a TNFRI polypeptide having the amino acid sequence as set forth in SEQ ID NO: 1" refers to a polypeptide containing numbers and kinds of amino acid modifications not detrimental to an intrinsic activity of TNFRI, that is, amino acid substitution, deletion, addition or other modifications. Specifically, the present invention provides a modified TNFRI polypeptide or a fragment thereof containing modifications corresponding to the above-specified amino acid modifications in the variant having homology of more than 90%, more than 95%, more than 96%, more than 97%, more than 98% or more than 99% with a polypeptide having the amino acid sequence as set forth in SEQ ID NO: 1.

The above-mentioned variant has sequence homology of more than 90%, more than 95%, more than 96%, more than 97%, more than 98%, or more than 99% with a polypeptide having the sequence as set forth in SEQ ID NO: 1, except the amino acid modifications of the present invention for improving resistance to protease, and includes allelic variant isoforms of human TNFRI polypeptide, tissue-specific isoforms and allelic variants thereof, synthetic variants with one or more amino acid mutations, replacements, deletions, insertions or additions, synthetic molecules prepared by translation of nucleic acids, proteins isolated from human and non-human tissue and cells, chimeric TNFRI polypeptides and modified forms thereof.

As used herein, the term "corresponding modification" refers to a modification of residues compared among or between polypeptides that are other isoforms. That is, the "corresponding modification" means a modification corresponding to the amino acid modification of the present invention for improving resistance to protease at the position having a residue identified to be functionally unchangeable upon sequence alignment with the amino acid sequence of a native human TNFRI polypeptide as set forth in SEQ ID NO: 1. Those skilled in the art can readily identify modifications of residues that correspond between or among such polypeptides. For example, by aligning the sequences of TNFRI polypeptides, one of skill in the art can identify corresponding residues, using conserved and identical amino acid residues as guides.

Further, the present invention provides a TNFRI polypeptide or a fragment thereof containing the amino acid sequence represented by any one of SEQ ID NO: 6 to SEQ ID NO: 266, preferably a TNFRI polypeptide or a fragment thereof containing the amino acid sequence represented by any one of SEQ ID NOS: 18, 19, 33, 52, 62, 69, 70, 73, 78, 79, 94, 95, 109, 128, 138, 145, 146, 149, 154, 155, 164, 165, 178, 179, 193, 212, 222, 229, 230, 233, 238, 239, 248, 249, or 258 to 266, and more preferably a TNFRI polypeptide or a fragment thereof containing the amino acid sequence represented by any one of SEQ ID NOS: 18, 19, 69, 70, 78, 94, 95, 145, 146, 154, 164, 165, 178, 179, 229, 230, 238, 248, 249, or 261 to 263.

The modified TNFRI polypeptide or a fragment thereof in accordance with the present invention may further contain other chemical modifications such as post-translational modifications of a protein, for example, glycosylation by a carbohydrate moiety, acylation (e.g., acetylation or succinylation), methylation, phosphorylation, hesylation, carbamylation, sulfation, prenylation, oxidation, guanidination, amidination, carbamylation (e.g., carbamoylation), trinitrophenylation, nitration, and PEGylation, for the purpose of increasing protease resistance, decreasing immunogenicity, or maintaining or enhancing biological activity, in addition to the above-mentioned amino acid modifications.

Further, the present invention provides a gene encoding the foregoing TNFRI polypeptide or a fragment thereof.

The gene encoding a TNFRI polypeptide or a fragment thereof in accordance with the present invention includes a gene engineered for optimization of the expression in *E. coli*. Due to the difference in gene codon between human and *E. coli*, when a human gene is expressed in *E. coli*, an expression yield of the gene is low. For this reason, a gene engineered to be suitable for the expression in *E. coli* based on a human TNFRI gene, for example the TNFRI gene of SEQ ID NO: 5 may be used in the present invention. Such a gene exhibits a higher expression level than a human TNFRI gene, when it is inserted into an *E. coli* expression vector (for example, pET44a (Cat. No: 71122-3, Novagen)) and then expressed in an *E. coli* cell with no addition of codon (e.g.: BL21(DE3)). Therefore, using the above gene, a TNFRI fragment and a TNFRI variant may be efficiently produced in *E. coli.*

Further, the present invention provides a vector containing the same gene. The vector that can be used for the introduction of a gene in the present invention may be a vector known in the art, preferably a vector having a cleavage map of FIG. 1 or FIG. 5.

Further, the present invention provides a microbial or animal cell transformed with the vector. The microbial or animal cell that can be used for the transformation of a vector in the present invention may be a known microbial or animal cell for transformation used in the art, preferably an *E. coli* cell, a CHO cell, or an HEK293 cell, and more preferably an *E. coli* cell (for example, *E. coli* BL21(DE3)).

The present invention provides a method for producing TNFRI using *E. coli.*

TNFRI may be produced by using an animal cell (Bernie et al., The Journal of Pharmacology and Experimental Therapeutics. 301: 418-426, 2002; and Scallon et al., Cytokine. 7:759-770, 1995).

Since when it is expressed in *E. coli*, TNFRI is expressed in the form of an inclusion body which is not conformationally active, a process of refolding into an active protein is required (Silvia et al., Analytical Biochemistry 230: 85-90, 1995; and Karin et al., Cytokine. 7:26-38, 1995). Therefore, the modified TNFRI polypeptide or a fragment thereof in accordance with the present invention may be produced by expressing TNFRI in the form of an inclusion body in *E. coli*, refolding the expressed TNFRI into active TNFRI, and purifying the active TNFRI by using gel filtration chromatography or the like. Alternatively, the modified TNFRI polypeptide or a fragment thereof in accordance with the present invention may be produced in the form of a soluble protein instead of an inclusion body granules in *E. coli*, using an expression method involving attachment of a hydrophilic fusion protein, a low-temperature culture method, or the like. In Examples of the present invention, TNFRI as a soluble protein is produced in *E. coli* by linking a hydrophilic NusA protein to the N-terminus of a TNFRI protein.

Further, the present invention provides a method for producing a TNFRI polypeptide or a fragment thereof, including introducing the gene into a suitable vector, transforming the vector into a host cell to give a transformant, and culturing the transformant in a medium to express the TNFRI polypeptide or a fragment thereof.

Further, the present invention provides a method for the treatment of a TNF-mediated disease or internal symptom (hereinafter, referred to as "TNF-mediated disease"). Examples of the TNF-mediated disease, the related sequelae and symptoms associated therewith include: adult respiratory distress syndrome; anorexia; cancer (e.g., leukemia); chronic fatigue syndrome; graft-versus-host rejection; hyperalgesia; inflammatory bowel disease; neuroinflammatory disease; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia rheumatica and giant cell arteritis); septic shock; radiotherapy-induced side effects; systemic lupus erythematous; temporomandibular joint disease; thyroiditis and tissue transplantation.

Further, the present invention provides a composition for the prevention or treatment of rheumatoid arthritis or TNF-mediated disease, containing the modified TNFRI polypeptide or a fragment thereof.

Further, the present invention provides a composition for the prevention or treatment of rheumatoid arthritis or TNF-mediated disease, containing a gene encoding the modified TNFRI polypeptide or a fragment thereof, a vector containing the gene or a microbial or animal cell transformed with the vector.

The pharmaceutical composition of the present invention may be administered via an intravenous or subcutaneous route, in addition to an oral route and by inhalation. The pharmaceutical composition may be prepared for storage or administration by mixing a TNFRI variant having desired purity with pharmaceutically acceptable carriers, excipients or stabilizers. Acceptable carriers, excipients or stabilizers are nontoxic to recipients in the dosages and concentrations employed, and include buffers such as phosphate, citrate, acetate and other organic acid salts; antioxidants such as ascorbic acid; low-molecular weight (less than about 10 residues in length) peptides including polyarginine and proteins such as serum albumin, gelatin or immunoglobulin; hydrophilic polymers such as polyvinylpyrrolidone; amino acids such as glycine, glutamic acid, aspartic acid or arginine; and other carbohydrates including monosaccharides, disaccharides, cellulose and derivatives thereof, glucose, mannose or dextrins; chelating agents such as EDTA; sugar alcohols such as mannitol or sorbitol; counterions such as sodium; and/or non-ionic surfactants such as TWEEN™, Pluronics or polyethylene glycol (PEG).

The pharmaceutical composition of the present invention may be formulated in the form of a sterile composition for injection according to a conventional method known in the art. The sterile composition for injection may contain a solution or suspension of the active compound in a vehicle such as water or naturally occurring vegetable oil like sesame, peanut or cottonseed oil or a synthetic fatty vehicle like ethyl oleate. The sterile composition for injection may be incorporated into a buffer, a preservative, an antioxidant and the like according to an accepted pharmaceutical practice.

A modified TNFRI polypeptide or a fragment thereof, or a gene encoding the same, or a vector containing the same gene, or a microbial or animal cell transformed with the vector in accordance with the present invention is incorporated in a therapeutically effective amount for the TNF-mediated disease in a pharmaceutical composition.

As used herein, the term "therapeutically effective amount" refers to the amount/dose of an active ingredient or pharmaceutical composition that is sufficient to elicit an effective response (i.e., a biological or medical response of an animal or human sought by a researcher, veterinarian, medical doctor or other clinician) upon administration to a subject. The therapeutically effective amount is intended to encompass an amount to produce symptomatic alleviation of the disease or disorder being treated. It is apparent to those skilled in the art that the therapeutically effective amount and dosing frequency of the active ingredient of the present invention will vary depending on desired effects. Therefore, an optimum dosage can be readily determined by those skilled in the art and may be adjusted according to various factors such as type and severity of the disease, contents of active ingredients and other ingredients in the composition, dosage form, and the age, weight, physical condition and gender of the subject, as well as diet, administration timing and route and excretion rate of the composition, duration of treatment, and concurrent medication. For example, for adults, the TNFRI variant of the present invention is preferably administered at a dose of 0.01 to 1,000 mg/kg once a day, and more preferably 0.1 to 100 mg/kg once a day.

The TNFRI polypeptide or a fragment thereof in accordance with the present invention may be administered as an addition for other therapies and may be administered with other pharmaceutical compositions suitable for the indication being treated. The TNFRI polypeptide or a fragment thereof in accordance with the present invention and any of one or more known or novel anti-inflammatory drugs may be administered separately or in combination. Information regarding the compounds corresponding to such drugs can be found in "The Merck Manual of Diagnosis and Therapy", Sixteenth Edition, Merck, Sharp & Dohme Research Laboratories, Merck & Co., Rahway, N.J. (1992) and in "Pharmaprojects", PJB Publications Ltd.

As an example of the combination use, the TNFRI polypeptide or a fragment thereof in accordance with the present invention may be used in combination with first line drugs for control of inflammation, classified as non-steroidal, anti-inflammatory drugs (NSAIDs), for the treatment of TNF-mediated diseases, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis).

As another example of the combination use, the TNFRI polypeptide or a fragment thereof in accordance with the present invention may be used in combination with any of one or more slow-acting antirheumatic drugs (SAARDs) or disease modifying antirheumatic drugs (DMARDS), prodrug esters or pharmaceutically acceptable salts thereof, for the treatment of TNF-mediated diseases and multiple sclerosis as defined above.

As a further example of the combination use, the TNFRI polypeptide or a fragment thereof in accordance with the present invention may be used in combination with any of one or more COX2 inhibitors, prodrug esters or pharmaceutically acceptable salts thereof for the treatment of TNF-mediated diseases as defined above.

Further, the TNFRI polypeptide or a fragment thereof in accordance with the present invention may be used in combination with any of one or more antibacterial drugs, prodrug esters or pharmaceutically acceptable salts thereof for the treatment of TNF-mediated diseases as defined above.

The TNFRI polypeptide or a fragment thereof in accordance with the present invention may be used for the treatment of TNF-mediated diseases as defined above, in combination with any of one or more compounds given below: granulocyte colony stimulating factor; thalidomide; tenidap; tiapafant; nimesulide; panavir; rolipram; sulfasalazine; balsalazide; olsalazine; mesalazine; prednisolone; budesonide; methylprednisolone; hydrocortisone; methotrexate; cyclosporin; peptide T; (1R,3S)-cis-1-[9-(2,6-diaminopurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

The TNFRI polypeptide or a fragment thereof in accordance with the present invention may be used in combination with one or more additional TNF inhibitors for the treatment of TNF-mediated diseases as defined above. Such TNF inhibitors include compounds and proteins which block in vivo synthesis or extracellular release of TNF: for example, anti-TNF antibodies including MAK 195F Fab antibody (Holler et al. (1993), 1st International Symposium on Cytokines in Bone Marrow Transplantation, 147); CDP 571 anti-TNF monoclonal antibody (Rankin et al. (1995), British Journal of Rheumatology, 34:334-342); BAY X 1351 murine anti-tumor necrosis factor monoclonal antibody (Kieft et al. (1995), 7th European Congress of Clinical Microbiology and Infectious Diseases, 9); CenTNF cA2 anti-TNF monoclonal antibody (Elliott et al. (1994), Lancet, 344:1125-1127 and Elliott et al. (1994), Lancet, 344:1105-1110).

Further, the present invention provides a pharmaceutical preparation containing the TNFRI polypeptide or a fragment thereof. Preferably, the pharmaceutical preparation of the present invention further contains a pharmaceutically acceptable excipient. The pharmaceutical preparation of the present invention may be in the form of a pharmaceutical formulation selected from the group consisting of an oral formulation, an inhaler, an injection, a transmucosal formulation, and an external application.

The pharmaceutical preparation of the present invention contains a therapeutically effective amount of a pharmaceutically acceptable diluent, preservative, solubilizer, emulsifier, adjuvant or carrier.

In addition, the pharmaceutical preparation of the present invention contains additives including buffer (e.g. Tris buffer, acetate buffer, or phosphate buffer), detergents (e.g. TWEEN™ 80), antioxidants (e.g. ascorbic acid, sodium metabisulfite), preservatives (e.g. Thimerosal, benzyl alcohol)

and bulking substances (e.g. lactose, mannitol) which have been commonly used in the art. The additives may be incorporated into particulate preparations of polymeric compounds such as polylactic acid or polyglycolic acid or into liposomes. The pharmaceutical preparation of the present invention may contain hyaluronic acid for the purpose of promoting sustained duration in circulation. The pharmaceutical preparation of the present invention may optionally contain pharmaceutically acceptable liquid, semisolid, or solid diluents that serve as pharmaceutical vehicles, excipients, or media, including, but not being limited to, polyoxyethylene sorbitan monolaurate, starches, sucrose, dextrose, gum acacia, calcium phosphate, mineral oil, cocoa butter, and theobroma oil.

The pharmaceutical preparation of the present invention also contains inert additives which furnish protection against the stomach environment, and release of the biologically active material in the intestine.

The pharmaceutical preparation of the present invention is prepared using known techniques, including mixing, dissolving, granulating, dragee-making, levigating, emulsifying, encapsulating, entrapping or tabletting processes.

The pharmaceutical preparation of the present invention may be in the form of a liquid (e.g., a suspension, elixir and/or solution) or a solid (e.g., a powder, tablet and/or capsule), or may be formulated in the form of a depot. The depot preparation is typically longer acting than non-depot preparations. The depot preparation is prepared using suitable polymeric or hydrophobic materials (for example, an emulsion in a suitable oil) or ion exchange resins, or as sparingly soluble derivatives, for example, as a sparingly soluble salt. Further, the pharmaceutical preparation of the present invention contains a delivery system such as liposome or emulsion. Certain delivery systems are useful for preparing certain pharmaceutical preparations including those containing hydrophobic compounds. In certain embodiments, organic solvents such as dimethyl sulfoxide are used. In another aspect of the present invention, the pharmaceutical preparation of the present invention contains one or more tissue-specific delivery molecules designed to deliver pharmaceutical agents to specific tissues or cell types. For example, in certain embodiments, the pharmaceutical preparation contains a liposome coated with a tissue-specific antibody.

Preferably, the pharmaceutical preparation of the present invention may be formulated into an oral solid dosage form. Solid dosage forms include tablets, capsules, pills, troches or pellets.

Also, liposomal or proteinoid encapsulation may be used to formulate the composition of the present invention. Liposomes may be prepared from phospholipids, such as phosphatidylcholine (PC), phosphatidylethanolamine (PE), phosphatidic acid (PA), phosphatidylinositol (PI) and sphingomyelin (SM); and hydrophilic polymers, such as polyvinylpyrrolidone, polyvinylmethyl ether, polymethyl oxazoline, polyethyl oxazoline, polyhydroxypropyl oxazoline, polyhydroxypropyl methacrylamide, polymethacrylamide, polydimethylacrylamide, polyhydroxypropyl methacrylate, polyhydroxyethyl acrylate, hydroxymethyl cellulose, hydroxyethyl cellulose, polyethylene glycol and polyaspartamide.

If necessary, the TNFRI polypeptide or a fragment thereof contained in the pharmaceutical preparation of the present invention may be chemically modified so that oral delivery is efficacious. Generally, the chemical modification contemplated is the attachment of at least one moiety to the TNFRI variant polypeptide, where the moiety may be a substance which confers resistance to protease or helps uptake into the blood stream from the stomach or intestine. Preferably, the moiety for chemical modification may be a moiety for chemical modification to increase an overall stability of the pharmaceutical preparation of the present invention and therefore increase its circulation time in the body. Examples of the moiety include polyethylene glycol, copolymers of ethylene glycol and propylene glycol, carboxymethyl cellulose, dextran, polyvinyl alcohol, polyvinylpyrrolidone and polyproline. Other polymers that can be used are poly-1,3-dioxane and poly-1,3,6-trioxocane. Most preferred is a polyethylene glycol moiety (PEGylation).

As a carrier to enhance absorption of the pharmaceutical preparation of the present invention in the oral dosage form, a salt of a modified aliphatic amino acid, such as sodium N-(8-[2-hydroxybenzoyl]amino)caprylate (SNAC), may be used.

The pharmaceutical preparation of the present invention may be formulated as fine multiparticulates in the form of granules or pellets of a particle size of about 1 mm. In this case, the pharmaceutical may be in the form of a capsule. The multiparticulate preparation may be in the form of a powder, lightly compressed plug or tablet. The preparation may be prepared by compression.

The pharmaceutical preparation of the present invention may also be formulated in the form of, for example, liposome or microsphere encapsulation with further incorporation of colorants and flavoring agents.

Further, in order to enhance uptake of the TNFRI polypeptide or a fragment thereof which is an active ingredient in the pharmaceutical preparation of the present invention, additives may be used including fatty acids such as oleic acid or linoleic acid.

The pharmaceutical preparation of the present invention may be a controlled-release formulation. The TNFRI polypeptide or a fragment thereof, which is an active ingredient in such a formulation, may be incorporated into an inert carrier which permits controlled release by either diffusion or dissolution mechanisms. Further, the controlled-release formulation may contain a slowly disintegrating matrix, e.g., alginate or polysaccharide. Another form of the controlled-release formulation may be based on an Osmotic Release Oral delivery System (OROS, Alza Corp.). In the controlled-release formulation, the TNFRI variant which is the active ingredient of the present invention is enclosed in a semipermeable membrane which allows water to enter and push the active ingredient out through a single small opening due to osmotic effects. The controlled-release formulation of the present invention may have an enteric coating to exhibit a delayed release effect of the drug.

The pharmaceutical preparation of the present invention may be in the form of a film-coated tablet. The materials used in film coating are divided into two groups. The first group is a nonenteric material and includes methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, povidone and polyethylene glycol. The second group consists of enteric materials such as esters of phthalic acid. In detail, an enteric polymer as the enteric material is selected from the group consisting of an enteric cellulose derivative, an enteric acrylic copolymer, an enteric maleic copolymer, an enteric polyvinyl derivative, and a combination thereof. The enteric cellulose derivative is at least one selected from the group consisting of hypromellose acetate succinate, hypromellose phthalate, hydroxymethylethyl cellulose phthalate, cellulose acetate phthalate, cellulose acetate succinate, cellulose acetate maleate, cellulose benzoate phthalate, cellulose propionate phthalate, methylcellulose phthalate, carboxymethylethyl cellulose and ethylhydroxyethyl cellulose phthalate. The enteric acrylic copolymer is at least one selected from the group consisting of a styrene-acrylic acid copolymer, a methyl acrylate-acrylic acid copolymer, an acrylic acid-methyl methacrylate copolymer, a butyl acrylate-styrene-acrylic acid copolymer, a methacrylic acid-methyl methacrylate copolymer (e.g., EUDRAGIT™L 100, EUDRAGIT™S, Degussa), a methacrylic acid-ethyl acrylate copolymer (e.g., EUDRAGIT™L 100-55, Degussa), and methyl acrylate-methacrylic acid-octyl acrylate copolymer. The enteric maleic copolymer is at least one selected from the group consisting of a vinyl acetate-maleic anhydride copolymer, a styrene-maleic anhydride copolymer, a styrene-maleic acid monoester copolymer, a vinylmethylether-maleic anhydride copolymer, an ethylene-maleic anhydride copolymer, a vinylbutylether-maleic anhydride copolymer, an acrylonitrile-methyl acrylate-maleic anhydride copolymer, and a butyl acrylate-styrene-maleic anhydride copolymer. The enteric polyvinyl derivative is at least one selected from the group consisting of polyvinylalcohol phthalate, polyvinylacetal phthalate, polyvinylbutyrate phthalate, and polyvinylacetacetal phthalate.

A mixture of the above-mentioned coating materials may be used to provide the optimum film coating. Film coating may be carried out in a pan coater or in a fluidized bed granulator or by a compression coater.

The controlled-release pharmaceutical preparation of the present invention may contain the TNFRI polypeptide of the present invention or a fragment thereof in a semi-permeable matrix of a solid hydrophobic polymer in the form of a shaped article, e.g., film or microcapsule, for the purpose of sustained release of the drug. Examples of the sustained-release matrix include polyesters, hydrogels [e.g., poly(2-hydroxyethyl-methacrylate) or poly(vinylalcohol) as described by Langer et al., J. Biomed. Mater. Res., 15:167-277, 1981 and Langer, Chem. Tech., 12:98-105, 1982], polylactides (U.S. Pat. No. 3,773,919, EP 58,481), copolymers of L-glutamic acid and gamma ethyl-L-glutamate (Sidman et al., Biopolymers 22:547-556, 1983), non-degradable ethylene-vinyl acetate (Langer et al., supra), degradable lactic acid-glycolic acid copolymers (e.g., LUPRON DEPOT™ (injectable microspheres composed of lactic acid-glycolic acid copolymer and leuprolide acetate), and poly-D-(−)-3-hydroxybutyric acid (EP 133,988).

When encapsulated proteins remain in the body for a long time, they may denature or aggregate as a result of being exposed to moisture at 37° C., resulting in a loss of biological activity and possible changes in immunogenicity. Rational strategies can be devised for protein stabilization depending on the mechanism involved. For example, if the aggregation mechanism is discovered to form intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Further, the present invention provides a TNFRI variant of the present invention, and use of a pharmaceutical preparation containing the same. Such a pharmaceutical preparation may be administered via injection, or by oral, nasal, transdermal or other forms of administration, including, e.g., by intravenous, intradermal, intramuscular, intramammary, intraperitoneal, intrathecal, intraocular, intrapulmonary or subcutaneous injection; by sublingual, anal, vaginal, or by surgical implantation. The treatment may consist of a single dose or a plurality of doses over a period of time.

Further, the pharmaceutical preparation of the present invention may be delivered by a pulmonary delivery method. The pharmaceutical preparation of the present invention is delivered to the lung of a mammal while inhaling and traverses across the pulmonary epithelial lining to the blood stream.

A wide range of mechanical devices designed for pulmonary delivery of the drug may be used for pulmonary delivery of the pharmaceutical preparation of the present invention. Examples of such devices include nebulizers, metered dose inhalers, and powder inhalers, all of which are commercially available in the art.

The pharmaceutical preparation of the present invention may be appropriately formulated for optimum use in the foregoing devices. Typically, each formulation is specific to the type of device employed and may involve the use of an appropriate propellant, in addition to diluents, adjuvants or carriers useful in therapy.

The pharmaceutical preparation of the present invention for pulmonary delivery is preferably provided as a particulate form with an average particle size of approximately 10 μm or less, most preferably about 0.5 to 5 μm for effective delivery to the distal lung.

The pharmaceutical preparation of the present invention for pulmonary delivery may also contain a carbohydrate such as trehalose, mannitol, xylitol, sucrose, lactose or sorbitol, as a carrier. The pharmaceutical preparation may further contain dipalmitoylphosphatidylcholine (DPPC), dioleoylphoshatidyl ethanolamine (DOPE), distearoylphosphatidylcholine (DSPC) and dioleoylphosphatidylcholine (DOPC). The pharmaceutical preparation may also contain natural or synthetic surfactants. The pharmaceutical preparation may further contain polyethylene glycol, dextran such as cyclodextran, bile acid and other related derivatives, and amino acids used in a buffer formulation.

Also, the use of liposomes, microcapsules or microspheres, inclusion complexes, or other types of carriers is contemplated for pulmonary delivery of the pharmaceutical preparation of the present invention.

Pulmonary delivery of the pharmaceutical preparation of the present invention may be carried out using a nebulizer with either jet or ultrasonic means. The pharmaceutical preparation of the present invention suitable for use of a nebulizer contains the TNFRI variant dissolved in water at a concentration of about 0.1 to 25 mg of biologically active protein per mL of solution. The nebulizer formulation may also include a buffer and monosaccharides, which, for example, contributes to protein stabilization and the regulation of osmotic pressure. The nebulizer formulation may also contain a surfactant to reduce or prevent surface inducing aggregation of the protein caused by atomization of the solution in forming the aerosol.

The pharmaceutical preparation of the present invention for use with a metered-dose inhaler device will generally contain a finely divided powder of the composition containing the TNFRI variant of the present invention suspended in a propellant with the aid of a surfactant. The propellant may be a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or a combination thereof. Examples of a suitable surfactant that can be used herein include sorbitan trioleate and soya lecithin. Oleic acid may also be used as a surfactant.

The pharmaceutical preparation of the present invention for dispensing from a powder inhaler device is composed of a finely divided dry powder of the composition containing the TNFRI variant of the present invention and may also contain a bulking agent such as lactose, sorbitol, sucrose, mannitol, trehalose or xylitol. These may facilitate dispersion of the powder from the device.

Nasal delivery of the pharmaceutical preparation of the present invention is also contemplated. Nasal delivery allows the passage of a protein therapeutic to the blood stream directly after administering the protein therapeutic to the nose, thus preventing pulmonary deposition of the therapeutic product. The pharmaceutical preparation of the present invention for nasal delivery contains dextran or cyclodextran, etc. Delivery via transport across other mucous membranes is also contemplated for the pharmaceutical preparation of the present invention.

The dosage regimen of the pharmaceutical preparation of the present invention involved in a method for treating the above-described diseases or conditions will be determined by the attending physician, in light of various factors which modify the action of drugs, e.g. the age, condition, body weight, sex and diet of the patient, the severity of any infection, the time of administration and other clinical factors.

The pharmaceutical preparation of the present invention may be administered via single dosing or continuous dosing, but is preferably administered by an initial bolus followed by a continuous infusion to maintain therapeutic levels of the drug in circulation. Typical techniques known in the art will readily optimize effective dosages and administration regimens. The frequency of dosing will depend on the pharmacokinetic parameters of the agents and the route of administration. The dosage regimen, administration regimen and frequency of dosing may also be optimized according to the physical state, stability, rate of in vivo release, and rate of in vivo clearance of the administered agents. For each route of administration, a suitable dose may be calculated according to body weight, body surface area or organ size. Appropriate dosages may be ascertained due to established assays used for determining blood level dosages in conjunction with appropriate dose-response data. The final dosage regimen will be determined by the attending physician, in light of various factors which modify the action of drugs, e.g. the drug's specific activity, the severity and the responsiveness of the patient, the age, condition, body weight, sex and diet of the patient and other clinical factors. As studies are conducted, further information will emerge regarding the appropriate dosage levels and duration of treatment for various diseases and conditions.

Advantageous Effects

The modified human tumor necrosis factor receptor-I (TNFRI) polypeptide or a fragment thereof in accordance with the present invention has increased protease resistance and therefore exhibits improved bioavailability and absorption rate upon injection or oral administration. Therefore, the TNFRI polypeptide or a fragment thereof may be advantageously used as long-acting injections and oral protein medications.

MODE FOR INVENTION

The above and other objects, features and other advantages of the present invention will be more clearly understood from the following Examples. However, the present invention is not limited to the examples disclosed below.

The TNFRI polypeptide or a fragment thereof in accordance with the present invention was prepared using information of a human TNFRI genome whose genome has been already publicly disclosed.

Figure 1:
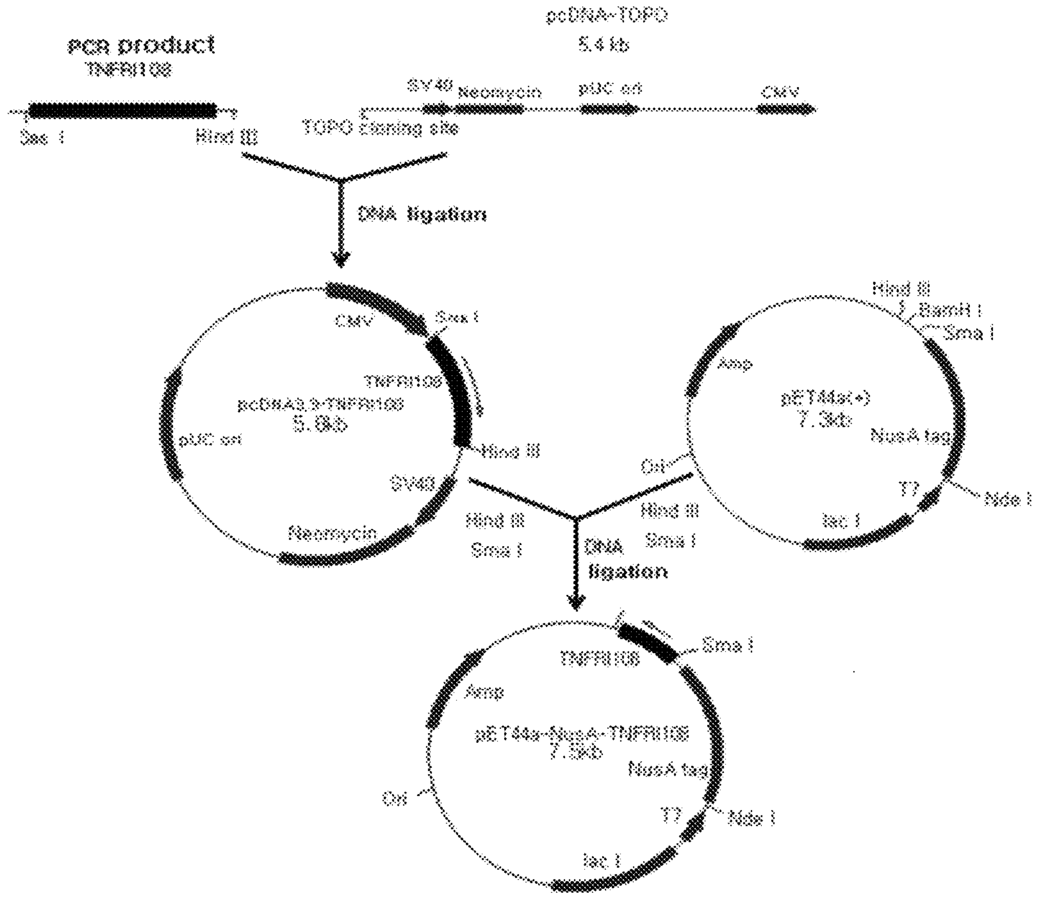
FIG. 1 is a schematic diagram showing the construction of an *E. coli* expression vector capable of expressing TNFRI108 to which NusA is fused by inserting a TNFRI108 gene into a pET44a vector having a gene encoding a NusA protein.

A TNFRI fragment gene was synthesized by a polymerase chain reaction (hereinafter, referred to as "PCR") and cloned into a vector PGEM T™ (Cat. No: A1380, Promega) which was then inserted into pET44a (Cat. No: 71122-3, Novagen) for expression in *E. coli*, thereby constructing a microbial expression vector (FIG. 1). This expression vector was transformed into BL21STAR™ (DE3) (Cat. No: C6010-03, Invitrogen), followed by confirming the production of a NusA-fused TNFRI fragment as an intracellular soluble protein. The expressed TNFRI was purified by chromatography using a 96-well plate.

Figure 5:
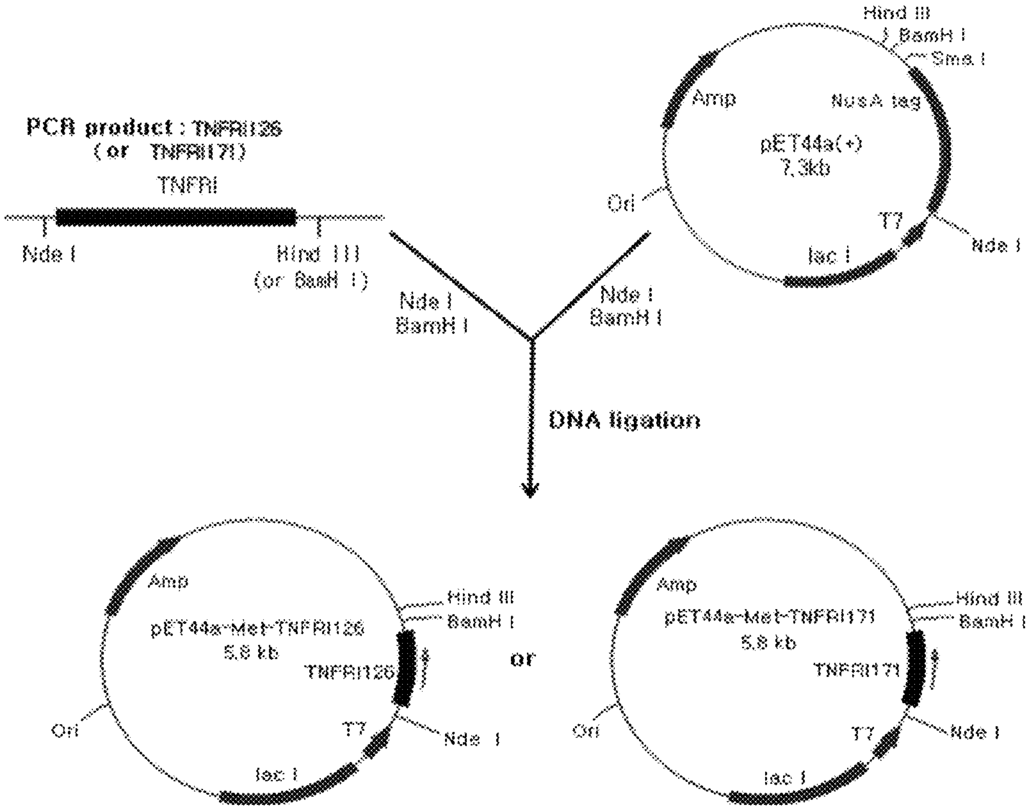
FIG. 5 is a schematic diagram showing the construction of an *E. coli* expression vector capable of expressing Met-TNFRI126 or Met-TNFRI171 through the insertion of a Met-TNFRI126 or Met-TNFRI171 gene into a pET44a vector.

In addition, an expression vector expressing only NusA-free TNFRI fragment was constructed using a pET44a expression vector (FIG. 5). At this time, the TNFRI fragment was expressed in the form of an inclusion body. The TNFRI fragment expressed in the form of an inclusion body was solubilized using a denaturing solution, converted into an active protein through a refolding process, and then purified by gel filtration chromatography.

In order to construct a protease-resistant variant, protease cleavage sites of the TNFRI fragment were inferred. In this regard, the amino acid sequence of the TNFRI fragment was screened for the cleavage sites of 10 representative different proteases located within the gastrointestinal tract, cells and blood using the peptide cutter program provided from Expasy (Expert Protein Analysis System).

To substitute the amino acids at the sites inferred to be cleaved by proteases with amino acids that do not undergo protease cleavage, without significant conformational change, a PAM250 matrix (W. A Pearson, *Rapid and Sensitive Sequence Comparison with FASTP and FASTA*, in Methods in Enzymology, ed. R. Doolittle (ISBN 0-12-182084-X, Academic Press, San Diego) 183: 63-98 (1990)) was used. A modified TNFRI polypeptide or a fragment thereof was prepared by substitution of the amino acids at the putative sites with the amino acids selected from among the amino acids to which zero or positive values are assigned by the PAM250 matrix and that are not recognized by proteases.

Using a vector expressing the TNFRI variant-encoding gene in the form of a NusA-fused soluble protein as a template, each variant vector was constructed according to site-directed mutagenesis. Each of the variant vectors thus constructed was transformed into BL21STAR™ (DE3) and the NusA-fused TNFRI fragment was produced as an intracellular soluble protein, followed by assay of activity and protease resistance. In order to confirm effects of the NusA fusion, a NusA-free TNFRI mutant was produced, and activity and protease resistance thereof were assayed and compared.

Hereinafter, preparation and confirmation of the modified TNFRI polypeptide or a fragment thereof in accordance with the present invention will be described in more detail.

Preparation Example

Preparation of TNFRI Gene Fragment: Construction of TNFRI171 Gene

It is reported that human TNFRI has 4 extracellular domains, binding of TNFRI to TNF-α is possible even with only three domains of TNFRI (TNFRI126), and more deficiency of the extracellular domains has no effect on the binding of TNFRI to TNF-α. Based on this fact, TNFRI171 (SEQ ID NO: 2) having 171 amino acid residues extending from amino acid residue 41 of the human TNFRI polypeptide as set forth in SEQ ID NO: 1, TNFRI126 (SEQ ID NO: 3) having 126 amino acid residues extending from amino acid residue 41 of human TNFRI, and TNFRI108 (SEQ ID NO: 4) having 108 amino acid residues extending from amino acid residue 41 of human TNFRI were selected as candidate peptides for constructing variants of the present invention. For producing such variants, the base sequence of TNFRI171 was modified to be convenient for expression in *E. coli*, using codons being matched with *E. coli* (SEQ ID NO: 5). This sequence was constructed by PCR-based gene synthesis method.

In order to insert the synthesized TNFRI171 gene sequence (SEQ ID NO: 5) for expression in *E. coli* into a PGEM™-T (Cat. No: A1380, Promega) vector, 3 μl of the synthetic gene was added to 1 μl of the PGEM™-T vector, and 1 μl of ligase (Cat. No: M2200S, NEB) and a ligation solution (2× ligation buffer) were added thereto, followed by reaction at room temperature for 5 minutes. 2 μl of the reaction solution was taken and added to an XL1-blue competent cell (Cat. No: RH119-J80, RBC) which was then transformed by applying heat shock at 47° C. for 1 minutes, followed by static culture in an LB solid medium containing ampicillin to obtain a colony. The colony was cultured in an LB liquid medium containing ampicillin, the plasmid was isolated therefrom and the gene sequence was confirmed by fluorescence-labeling of ddNTP using PCR (SolGent Inc., South Korea). This gene was designated as PGEM™-TNFRI171. Hereinafter, TNFRI126 and TNFRI108 genes other than TNFRI171 were obtained by PCR using the above-obtained PGEM™-TNFRI171 gene as a template.

Example 1

Design of TNFRI Single Variants

In order to construct a variant, first a variant having resistance to protease was designed. For determination of mutation sites, the TNFRI171 amino acid sequence was inferred for the cleavage sites of 10 representative different proteases given in Table 1 and located within the gastrointestinal tract, cells and blood using the peptide cutter program provided from Expasy (Expert Protein Analysis System). The amino acids at the putative cleavage sites were substituted with amino acids that do not undergo protease cleavage, without significant conformational change. Determination of amino acids to be substituted was carried out using a PAM250 matrix. With reference to the 19 corresponding amino acids having a positive value, 0, or a negative value for each amino acid in the PAM250 matrix, amino acids which do not undergo protease cleavage and have a positive value or 0 were determined as amino acids to be substituted.

TABLE 1

Protease-specific amino acid and resistance-inducing amino acid

| Protease | Amino acid cleaved by recognition | Resistance-inducing substitution amino acid |
|---|---|---|
| Arg-C proteinase | R | H or Q |
| Asp-N endopeptidase | -D | N or Q |
| Chymotrypsin | [FYWML], not before P | S or I, H |
| Enterokinase | K | N or Q |
| Glutamyl endopeptidase | E | N or Q |
| Lys-C | K | N or Q |
| Lys-N | K | N or Q |
| Proline endopeptidase | H, K or R, -P | A or S |
| Thrombin | R | N or Q |
| Trypsin | K | N or Q |

The list of TNFRI variants designed according to the foregoing method is given in Table 2.

TABLE 2

List of TNFRI single variants designed

| Variant No. | Mutation |
|---|---|
| TNFRIx-1 | K48Q |
| TNFRIx-2 | K48N |
| TNFRIx-3 | Y49I |
| TNFRIx-4 | Y49H |
| TNFRIx-5 | P52A |
| TNFRIx-6 | P52S |
| TNFRIx-7 | K61Q |
| TNFRIx-8 | K61N |
| TNFRIx-9 | K64Q |
| TNFRIx-10 | K64N |
| TNFRIx-11 | Y67I |
| TNFRIx-12 | Y67H |

TABLE 2-continued

List of TNFRI single variants designed

| Variant No. | Mutation |
|---|---|
| TNFRIx-13 | L68I |
| TNFRIx-14 | L68V |
| TNFRIx-15 | Y69I |
| TNFRIx-16 | Y69H |
| TNFRIx-17 | D71N |
| TNFRIx-18 | D71Q |
| TNFRIx-19 | D78N |
| TNFRIx-20 | D78Q |
| TNFRIx-21 | D80N |
| TNFRIx-22 | D80Q |
| TNFRIx-23 | R82H |
| TNFRIx-24 | R82Q |
| TNFRIx-25 | E83Q |
| TNFRIx-26 | E83N |
| TNFRIx-27 | E85Q |
| TNFRIx-28 | E85N |
| TNFRIx-29 | F89I |
| TNFRIx-30 | F89V |
| TNFRIx-31 | E93Q |
| TNFRIx-32 | E93N |
| TNFRIx-33 | L96I |
| TNFRIx-34 | L96V |
| TNFRIx-35 | R97H |
| TNFRIx-36 | R97Q |
| TNFRIx-37 | L100I |
| TNFRIx-38 | L100V |
| TNFRIx-39 | K104Q |
| TNFRIx-40 | K104N |
| TNFRIx-41 | R106H |
| TNFRIx-42 | R106Q |
| TNFRIx-43 | K107Q |
| TNFRIx-44 | K107N |
| TNFRIx-45 | E108Q |
| TNFRIx-46 | E108N |
| TNFRIx-47 | M109I |
| TNFRIx-48 | M109V |
| TNFRIx-49 | E113Q |
| TNFRIx-50 | E113N |
| TNFRIx-51 | D120N |
| TNFRIx-52 | D120Q |
| TNFRIx-53 | R121H |
| TNFRIx-54 | R121Q |
| TNFRIx-55 | D122N |
| TNFRIx-56 | D122Q |
| TNFRIx-57 | R128H |
| TNFRIx-58 | R128Q |
| TNFRIx-59 | K129Q |
| TNFRIx-60 | K129N |
| TNFRIx-61 | Y132I |
| TNFRIx-62 | Y132H |
| TNFRIx-63 | R133H |
| TNFRIx-64 | R133Q |
| TNFRIx-65 | Y135I |
| TNFRIx-66 | Y135H |
| TNFRIx-67 | W136H |
| TNFRIx-68 | W136S |
| TNFRIx-69 | E138Q |
| TNFRIx-70 | E138N |
| TNFRIx-71 | L140I |
| TNFRIx-72 | L140V |
| TNFRIx-73 | F141I |
| TNFRIx-74 | F141V |
| TNFRIx-75 | F144I |
| TNFRIx-76 | F144V |
| TNFRIx-77 | L150I |
| TNFRIx-78 | L150V |
| TNFRIx-79 | L156I |
| TNFRIx-80 | L156V |
| TNFRIx-81 | E160Q |
| TNFRIx-82 | E160N |
| TNFRIx-83 | K161Q |
| TNFRIx-84 | K161N |
| TNFRIx-85 | E200Q |
| TNFRIx-86 | E200N |
| TNFRIx-87 | K203Q |
| TNFRIx-88 | K203N |
| TNFRIx-89 | E206Q |
| TNFRIx-90 | E206N |
| TNFRIx-91 | D207Q |
| TNFRIx-92 | D207N |

*With regard to the following Examples, x in the above Table represents 108, 126 or 171 for variants 1 to 76, 126 or 171 for variants 77 to 84, and 171 for variants 85 to 92.

Example 2

Construction of TNFRI108 variants

(1) Construction of TNFRI108 Gene and Expression Vector

For the expression of a soluble TNFRI108 protein in *E. coli*, an expression vector was constructed using a commercially available pET44a vector (Cat. No: 71122-3, Novagen) containing a NusA gene.

Specifically, a TNFRI108 gene was obtained by PCR using the PGEM™-TNFRI171 plasmid constructed in Preparation Example above, as a template. For cloning of the TNFRI108 gene into a pET44a vector, restriction enzyme SmaI and HindIII recognition sites were added to the 5' end and 3' end of the gene, respectively.

```
Forward primer:
5'-ccccggggcgatgacgatgacaaagatagcgtgtgcccg-3'

Reverse primer:
5'-taagcttattacagggagcaattaaaacactgg-3'
```

PCR was carried out under the following conditions: primary denaturation at 95° C. for 5 minutes, 25 cycles of secondary denaturation at 95° C. for 1 minute, primer annealing at 60° C. for 40 seconds and elongation at 72° C. for 1 minute, followed by final enzymatic reaction at 72° C. for 10 minutes. 2 μl of the amplified gene was inserted into a pcDNA3.3 TOPO TA vector (Cat. No: K8300-01, Invitrogen) according to the manufacture's protocol. 2 μl of the reaction solution was taken and added to an XL1-blue competent cell (Cat. No: RH119-J80, RBC) which was then transformed by applying heat shock at 42° C. for 1 minute, followed by static culture in an LB solid medium containing ampicillin to obtain a colony. The colony was cultured in an LB liquid medium containing ampicillin, the plasmid was isolated therefrom and the gene sequence was confirmed by labeling of ddNTP with a fluorescent substance (SolGent Inc., South Korea). This construct was designated as pcDNA3.3-TNFRI108.

Restriction enzymes (SmaI and HindIII) were added to the constructed pcDNA3.3-TNFRI108 vector and a pET44a vector, respectively, followed by reaction at 37° C. for 3 hours. After treatment with the restriction enzymes, the reaction product was subjected to electrophoresis on 1% agarose gel, and the DNA band at the corresponding size position was excised from the agarose gel with a razor and extracted using a DNA isolation kit (Cat. No: 102-102, GeneAll). The extracted pET44a vector and the TNFRI108 gene DNA were subjected to ligation using ligase (Cat. No: M2200S, NEB). 2 μl of the reaction solution was taken and added to an XL1-blue competent cell (Cat. No: RH119-J80, RBC) which was then transformed by applying heat shock at 47° C. for 1 minutes, followed by static culture in an LB solid medium containing ampicillin to obtain a colony. The colony was cultured in an LB liquid medium containing ampicillin, and the plasmid was isolated to construct a TNFRI108 *E. coli* expression vector (FIG. 1). The thus-constructed TNFRI108 *E. coli* expression vector was designated as a pET44a-NusA-TNFRI108 plasmid.

(2) Construction of DNA Encoding TNFRI108 Single Variant

For the construction of a site-specific TNFRI108 single variant, a TNFRI108 single variant was constructed by site-directed mutagenesis. Primers used for the construction of TNFRI108 single variant are given in Table 3 below.

Specifically, using the pET44a-NusA-TNFRI108 plasmid as a template, each pair of primers corresponding to variants 1 to 76 listed in Table 3 below was dissolved to a concentration of 20 pmol in distilled water, followed by PCR using Pfu polymerase to construct each of site-directed variants. The composition of the solution used in the amplification reaction is as follows.

1.0 μl of pET44a-NusA-TNFRI108 plasmid DNA, 1.0 μl of each of 20 pmol forward primers, 1.0 μl of each of 20 pmol reverse primers, 25.0 μl of 2× PRIMESTAR™ PCR buffer, 4.0 μl of each of 200 μM dNTPs, 0.5 μl of PRIMESTAR™ HS DNA polymerase (Cat. No: R044A, Takara) and 17.5 μl of distilled water were added to make 50 μl of a reaction solution.

PCR was carried out under the following conditions: primary denaturation at 98° C. for 5 minutes, 17 cycles of secondary denaturation at 98° C. for 30 seconds, primer annealing at 55° C. for 30 seconds and elongation at 72° C. for 9 minutes, followed by final enzymatic reaction at 72° C. for 10 minutes.

The PCR product was treated with a DpnI enzyme at 37° C. for 2 hours to degrade the *E. coli*-derived DNA and obtain the PCR-amplified DNA. 2 μl of the DNA solution was taken and added to an XL1-blue competent cell (Cat. No: RH119-J80, RBC) which was then transformed by applying heat shock at 42° C. for 1 minute, followed by static culture in an LB solid medium containing ampicillin to obtain a colony. The colony was cultured in an LB liquid medium containing ampicillin, and the plasmid was isolated and subjected to nucleotide sequencing analysis to confirm the completion of site-specific mutation.

TABLE 3

Primers for site-directed mutagenesis

| Variant No. | Variation | Primer direction | Primer sequence |
|---|---|---|---|
| TNFRI-1 | K48Q | Forward | 5'-atagcgtgtgcccgcagggtcagtatattcatcc-3' |
| | | Reverse | 5'-ggatgaatatactgaccctgcgggcacacgctat-3' |
| TNFRI-2 | K48N | Forward | 5'-gtgtgcccgcagggtaactatattcatccgcaaa-3' |
| | | Reverse | 5'-tttgcggatgaatatagttaccctgcgggcacac-3' |
| TNFRI-3 | Y49I | Forward | 5'-gcccgcagggtaagattattcatccgcaaaat-3' |
| | | Reverse | 5'-attttgcggatgaataatcttaccctgcgggc-3' |
| TNFRI-4 | Y49H | Forward | 5'-gtgcccgcagggtaagcatattcatccgcaaaat-3' |
| | | Reverse | 5'-attttgcggatgaatatgcttaccctgcgggcac-3' |
| TNFRI-5 | P52A | Forward | 5'-cgcagggtaagtatattcatgcgcaaaataactc-3' |
| | | Reverse | 5'-gagttattttgcgcatgaatatacttaccctgcg-3' |
| TNFRI-6 | P52S | Forward | 5'-gggtaagtatattcatagccaaaataactctatc-3' |
| | | Reverse | 5'-gatagagttattttggctatgaatatacttaccc-3' |
| TNFRI-7 | K61Q | Forward | 5'-taactctatctgttgcacacagtgtcacaaaggg-3' |
| | | Reverse | 5'-ccctttgtgacactgtgtgcaacagatagagtta-3' |
| TNFRI-8 | K61N | Forward | 5'-ctctatctgttgcacaaactgtcacaaagggac-3' |
| | | Reverse | 5'-gtccctftgtgacagtttgtgcaacagatagag-3' |
| TNFRI-9 | K64Q | Forward | 5'-gcacaaagtgtcaccaggggacgtacctgtat-3' |
| | | Reverse | 5'-atacaggtacgtcccctggtgacactttgtgc-3' |
| TNFRI-10 | K64N | Forward | 5'-gcacaaagtgtcacaacgggacgtacctgtata-3' |
| | | Reverse | 5'-tatacaggtacgtcccgttgtgacactttgtgc-3' |
| TNFRI-11 | Y67I | Forward | 5'-gtcacaaagggacgattctgtataatgactgtc-3' |
| | | Reverse | 5'-gacagtcattatacagaatcgtccctttgtgac-3' |
| TNFRI-12 | Y67H | Forward | 5'-gtgtcacaaagggacgcatctgtataatgactg-3' |
| | | Reverse | 5'-cagtcattatacagatgcgtccctttgtgacac-3' |
| TNFRI-13 | L68I | Forward | 5'-cacaaagggacgtacatttataatgactgtccgg-3' |
| | | Reverse | 5'-ccggacagtcattataaatgtacgtccctttgtg-3' |
| TNFRI-14 | L68V | Forward | 5'-gtgtcacaaagggacgcatctgtataatgactg-3' |
| | | Reverse | 5'-cagtcattatacagatgcgtccctttgtgacac-3' |
| TNFRI-15 | Y69I | Forward | 5'-caaagggacgtacctgattaatgactgtccgggg-3' |
| | | Reverse | 5'-ccccggacagtcattaatcaggtacgtccctttg-3' |

TABLE 3-continued

| Primers for site-directed mutagenesis | | | |
|---|---|---|---|
| Variant No. | Variation | Primer direction | Primer sequence |
| TNFRI-16 | Y69H | Forward | 5'-caaagggacgtacctgcataatgactgtccggg-3' |
| | | Reverse | 5'-cccggacagtcattatgcaggtacgtccctttg-3' |
| TNFRI-17 | D71N | Forward | 5'-gggacgtacctgtataataactgtccggggc-3' |
| | | Reverse | 5'-gccccggacagttattatacaggtacgtccc-3' |
| TNFRI-18 | D71Q | Forward | 5'-gggacgtacctgtataatcagtgtccggggcc-3' |
| | | Reverse | 5'-ggccccggacactgattatacaggtacgtccc-3' |
| TNFRI-19 | D78N | Forward | 5'-ggggccgggtcagaacaccgactgccgcg-3' |
| | | Reverse | 5'-cgcggcagtcggtgttctgacccggcccc-3' |
| TNFRI-20 | D78Q | Forward | 5'-gggccgggtcagcagaccgactgccgc-3' |
| | | Reverse | 5'-gcggcagtcggtctgctgacccggccc-3' |
| TNFRI-21 | D80N | Forward | 5'-gggtcaggataccaactgccgcgagtg-3' |
| | | Reverse | 5'-cactcgcggcagttggtatcctgaccc-3' |
| TNFRI-22 | D80Q | Forward | 5'-gggtcaggatacccagtgccgcgagtgcg-3' |
| | | Reverse | 5'-cgcactcgcggcactgggtatcctgaccc-3' |
| TNFRI-23 | R82H | Forward | 5'-ggataccgactgccatgagtgcgagagtggg-3' |
| | | Reverse | 5'-cccactctcgcactcatggcagtcggtatcc-3' |
| TNFRI-24 | R82Q | Forward | 5'-ggataccgactgccaggagtgcgagagtgg-3' |
| | | Reverse | 5'-ccactctcgcactcctggcagtcggtatcc-3' |
| TNFRI-25 | E83Q | Forward | 5'-accgactgccgccagtgcgagagtg-3' |
| | | Reverse | 5'-cactctcgcactggcggcagtcggt-3' |
| TNFRI-26 | E83N | Forward | 5'-ataccgactgccgcaactgcgagagtgggtc-3' |
| | | Reverse | 5'-gacccactctcgcagttgcggcagtcggtat-3' |
| TNFRI-27 | E85Q | Forward | 5'-ctgccgcgagtgccagagtgggtcatt-3' |
| | | Reverse | 5'-aatgacccactctggcactcgcggcag-3' |
| TNFRI-28 | E85N | Forward | 5'-gactgccgcgagtgcaacagtgggtcatttacag-3' |
| | | Reverse | 5'-ctgtaaatgacccactgttgcactcgcggcagtcg-3' |
| TNFRI-29 | F89I | Forward | 5'-gtgcgagagtgggtcaattacagcgagtgag-3' |
| | | Reverse | 5'-ctcactcgctgtaattgacccactctcgcac-3' |
| TNFRI-30 | F89V | Forward | 5'-cgagtgcgagagtgggtcagtgacagcgagtg-3' |
| | | Reverse | 5'-cactcgctgtcactgacccactctcgcactcg-3' |
| TNFRI-31 | E93Q | Forward | 5'-gtgggtcatttacagcgagtcagaatcatctgcg-3' |
| | | Reverse | 5'-cgcagatgattctgactcgctgtaaatgacccac-3' |
| TNFRI-32 | E93N | Forward | 5'-gtcatttacagcgagtaacaatcatctgcgccac-3' |
| | | Reverse | 5'-gtggcgcagatgattgttactcgctgtaaatgac-3' |
| TNFRI-33 | L96I | Forward | 5'-gcgagtgagaatcatattcgccactgcctgagc-3' |
| | | Reverse | 5'-gctcaggcagtggcgaatatgattctcactcgc-3' |
| TNFRI-34 | L96V | Forward | 5'-tacagcgagtgagaatcatgtgcgccactgc-3' |
| | | Reverse | 5'-gcagtggcgcacatgattctcactcgctgta-3' |
| TNFRI-35 | R97H | Forward | 5'-gagtgagaatcatctgcatcactgcctgagctg-3' |
| | | Reverse | 5'-cagctcaggcagtgatgcagatgattctcactc-3' |
| TNFRI-36 | R97Q | Forward | 5'-gagtgagaatcatctgcagcactgcctgagctg-3' |
| | | Reverse | 5'-cagctcaggcagtgctgcagatgattctcactc-3' |
| TNFRI-37 | L100I | Forward | 5'-catctgcgccactgcattagctgttctaagtgtc-3' |
| | | Reverse | 5'-gacacttagaacagctaatgcagtggcgcagatg-3' |
| TNFRI-38 | L100V | Forward | 5'-catctgcgccactgcgtgagctgttctaag-3' |
| | | Reverse | 5'-cttagaacagctcacgcagtggcgcagatg-3' |
| TNFRI-39 | K104Q | Forward | 5'-cgccactgcctgagctgttctcagtgtcgtaaa-3' |
| | | Reverse | 5'-tttacgacactgagaacagctcaggcagtggcg-3' |

TABLE 3-continued

Primers for site-directed mutagenesis

| Variant No. | Variation | Primer direction | Primer sequence |
|---|---|---|---|
| TNFRI-40 | K104N | Forward | 5'-cactgcctgagctgttctaactgtcgtaaagag-3' |
| | | Reverse | 5'-ctctttacgacagttagaacagctcaggcagtg-3' |
| TNFRI-41 | R106H | Forward | 5'-gctgttctaagtgtcataaagagatgggccaag-3' |
| | | Reverse | 5'-cttggcccatctctttatgacacttagaacagc-3' |
| TNFRI-42 | R106Q | Forward | 5'-gctgttctaagtgtcagaaagagatgggccaag-3' |
| | | Reverse | 5'-cttggcccatctctttctgacacttagaacagc-3' |
| TNFRI-43 | K107Q | Forward | 5'-gttctaagtgtcgtcaggagatgggccaagttg-3' |
| | | Reverse | 5'-caacttggcccatctcctgacgacacttagaac-3' |
| TNFRI-44 | K107N | Forward | 5'-gttctaagtgtcgtaacgagatgggccaagttg-3' |
| | | Reverse | 5'-caacttggcccatctcgttacgacacttagaac-3' |
| TNFRI-45 | E108Q | Forward | 5'-gctgttctaagtgtcgtaaacagatgggccaag-3' |
| | | Reverse | 5'-cttggcccatctgtttacgacacttagaacagc-3' |
| TNFRI-46 | E108N | Forward | 5'-gttctaagtgtcgtaaaaacatgggccaagttg-3' |
| | | Reverse | 5'-caacttggcccatgtttttacgacacttagaac-3' |
| TNFRI-47 | M109I | Forward | 5'-ctaagtgtcgtaaagagattggccaagttgaaat-3' |
| | | Reverse | 5'-atttcaacttggccaatctctttacgacacttag-3' |
| TNFRI-48 | M109V | Forward | 5'-ctaagtgtcgtaaagaggtgggccaagttgaaat-3' |
| | | Reverse | 5'-atttcaacttggcccacctctttacgacacttag-3' |
| TNFRI-49 | E113Q | Forward | 5'-gagatgggccaagttcagatttcttcatgtacgg-3' |
| | | Reverse | 5'-ccgtacatgaagaaatctgaacttggcccatctc-3' |
| TNFRI-50 | E113N | Forward | 5'-gagatgggccaagttaacatttcttcatgtacgg-3' |
| | | Reverse | 5'-ccgtacatgaagaaatgttaacttggcccatctc-3' |
| TNFRI-51 | D120N | Forward | 5'-tttcttcatgtacggtaaaccgcgatacggtatg-3' |
| | | Reverse | 5'-cataccgtatcgcggtttaccgtacatgaagaaa-3' |
| TNFRI-52 | D120Q | Forward | 5'-tttcttcatgtacggtacagcgcgatacggtatg-3' |
| | | Reverse | 5'-cataccgtatcgcgctgtaccgtacatgaagaaa-3' |
| TNFRI-53 | R121H | Forward | 5'-catgtacggtagaccatgatacggtatgtggttg-3' |
| | | Reverse | 5'-caaccacataccgtatcatggtctaccgtacatg-3' |
| TNFRI-54 | R121Q | Forward | 5'-catgtacggtagaccaggatacggtatgtggttg-3' |
| | | Reverse | 5'-caaccacataccgtatcctggtctaccgtacatg-3' |
| TNFRI-55 | D122N | Forward | 5'-gtacggtagaccgcaacacggtatgtggttgcc-3' |
| | | Reverse | 5'-ggcaaccacataccgtgttgcggtctaccgtac-3' |
| TNFRI-56 | D122Q | Forward | 5'-gtacggtagaccgccagacggtatgtggttgcc-3' |
| | | Reverse | 5'-ggcaaccacataccgtctggcggtctaccgtac-3' |
| TNFRI-57 | R128H | Forward | 5'-cggtatgtggttgccataaaaaccagtatcgcc-3' |
| | | Reverse | 5'-ggcgatactggtttttatggcaaccacataccg-3' |
| TNFRI-58 | R128Q | Forward | 5'-cggtatgtggttgccagaaaaaccagtatcgcc-3' |
| | | Reverse | 5'-ggcgatactggtttttctggcaaccacataccg-3' |
| TNFRI-59 | K129Q | Forward | 5'-ggtatgtggttgccgtcagaaccagtatcgcc-3' |
| | | Reverse | 5'-ggcgatactggttctgacggcaaccacatacc-3' |
| TNFRI-60 | K129N | Forward | 5'-ggtatgtggttgccgtaacaaccagtatcgcc-3' |
| | | Reverse | 5'-ggcgatactggttgttacggcaaccacatacc-3' |
| TNFRI-61 | Y132I | Forward | 5'-gttgccgtaaaaaccagattcgccattattggtc-3' |
| | | Reverse | 5'-gaccaataatggcgaatctggtttttacggcaac-3' |
| TNFRI-62 | Y132H | Forward | 5'-gttgccgtaaaaaccagcatcgccattattggtc-3' |
| | | Reverse | 5'-gaccaataatggcgatgctggtttttacggcaac-3' |
| TNFRI-63 | R133H | Forward | 5'-gccgtaaaaaccagtatcatcattattggtcag-3' |
| | | Reverse | 5'-ctgaccaataatgatgatactggtttttacggc-3' |
| TNFRI-64 | R133Q | Forward | 5'-gccgtaaaaaccagtatcagcattattggtcag-3' |
| | | Reverse | 5'-ctgaccaataatgctgatactggtttttacggc-3' |

TABLE 3-continued

Primers for site-directed mutagenesis

| Variant No. | Variation | Primer direction | Primer sequence |
|---|---|---|---|
| TNFRI-65 | Y135I | Forward | 5'-ccagtatcgccatatttggtcagaaaacctgttc-3' |
| | | Reverse | 5'-gaacaggttttctgaccaaatatggcgatactgg-3' |
| TNFRI-66 | Y135H | Forward | 5'-ccagtatcgccatcattggtcagaaaacctgttc-3' |
| | | Reverse | 5'-gaacaggttttctgaccaatgatggcgatactgg-3' |
| TNFRI-67 | W136H | Forward | 5'-cagtatcgccattatcattcagaaaacctgttcc-3' |
| | | Reverse | 5'-ggaacaggttttctgaatgataatggcgatactg-3' |
| TNFRI-68 | W136S | Forward | 5'-cagtatcgccattatagctcagaaaacctgttcc-3' |
| | | Reverse | 5'-ggaacaggttttctgagctataatggcgatactg-3' |
| TNFRI-69 | E138Q | Forward | 5'-cgccattattggtcacagaacctgttccagtg-3' |
| | | Reverse | 5'-cactggaacaggttctgtgaccaataatggcg-3' |
| TNFRI-70 | E138N | Forward | 5'-cgccattattggtcaaacaacctgttccagtg-3' |
| | | Reverse | 5'-cactggaacaggttgtttgaccaataatggcg-3' |
| TNFRI-71 | L140I | Forward | 5'-attggtcagaaaacatttccagtgttttaattg-3' |
| | | Reverse | 5'-caattaaaacactggaaatgttttctgaccaat-3' |
| TNFRI-72 | L140V | Forward | 5'-attggtcagaaaacgtgttccagtgttttaattg-3' |
| | | Reverse | 5'-caattaaaacactggaacacgttttctgaccaat-3' |
| TNFRI-73 | F141I | Forward | 5'-ggtcagaaaacctgattcagtgttttaattgctc-3' |
| | | Reverse | 5'-gagcaattaaaacactgaatcaggttttctgacc-3' |
| TNFRI-74 | F141V | Forward | 5'-ggtcagaaaacctggtgcagtgttttaattgctc-3' |
| | | Reverse | 5'-gagcaattaaaacactgcaccaggttttctgacc-3' |
| TNFRI-75 | F144I | Forward | 5'-gaaaacctgttccagtgtattaattgctccctg-3' |
| | | Reverse | 5'-cagggagcaattaatacactggaacaggttttc-3' |
| TNFRI-76 | F144V | Forward | 5'-gaaaacctgttccagtgtgtgaattgctccctg-3' |
| | | Reverse | 5'-cagggagcaattcacacactggaacaggttttc-3' |

(3) Expression of TNFRI108 and TNFRI108 Variants pl of the plasmid solution prepared above was taken and added to a BL21STAR™ (DE3) (Cat. No: C6010-03, Invitrogen) competent cell which was then transformed by applying heat shock at 42° C. for 1 minute, followed by static culture in an LB solid medium containing ampicillin to obtain a colony. *E. coli* (BL21STAR™ (DE3)) containing the pET44a-NusA-TNFRI108 or the TNFRI108 variant vector, which was inoculated onto 5 ml of an LB liquid medium (Cat. No: 244620, BD) containing 100 μg/ml of ampicillin, followed by aeration culture at 37° C. for 16 hours. The culture fluid was inoculated onto 50 ml of a medium containing 100 μg/ml of ampicillin and the cells were cultured to absorbance of 0.6 to 0.8 at 600 nm. Isopropyl-beta-D-thiogalactopyranoside (IPTG) (Cat. No: 19003, Sigma) was added at a final concentration of 1.0 mM to induce expression. After induction of expression, aeration culture was continued at 37° C. for 3 hours. The cultured cells were centrifuged at 5,000 rpm for 20 minutes to collect cells.

(4) Purification of TNFRI108 and TNFRI108 Variants

After the collected cells were subjected to cell lysis, the supernatant was recovered, subjected to primary purification by immobilized metal affinity chromatography, and subjected to secondary purification by hydrophobic chromatography to obtain a sample with purity of more than 90%.

Specifically, the collected cells were resuspended to absorbance of 10 at 600 nm in a resuspension solution (25 mM Tris solution, pH 8.5). The resuspended sample was subjected to cell lysis using a Sonicator (Cat. No: VCX750, Sonics) and centrifuged at 12,000 rpm for 20 minutes to recover the supernatant. 300 μl of HYPERCEL™ resin (Pall, Cat No: 20093-010) was loaded onto a 96-well filter plate (Pall, Cat No: PN5065) and washed with a 4 column volume of distilled water, and a 2 column volume of 0.1 M $NiCl_2$ was added thereto whereby nickel ions were bound to the resin. A 2 column volume of distilled water was flushed and the plate was washed with a 6 column volume of an equilibration solution (25 mM Tris, 0.1 M NaCl, pH 8.5). After a 2 column volume of a sample was added, the unbound sample was removed by using a 4 column volume of an equilibration solution. The plate was washed with a 10 column volume of a wash solution (25 mM Tris, 0.1 M NaCl, 50 mM imidazole, pH 8.5), followed by elution with a 2 column volume of an eluent solution (25 mM Tris, 0.1 M NaCl, 250 mM imidazole, pH 8.5) to recover TNFRI108 bound to the column.

Figure 2:
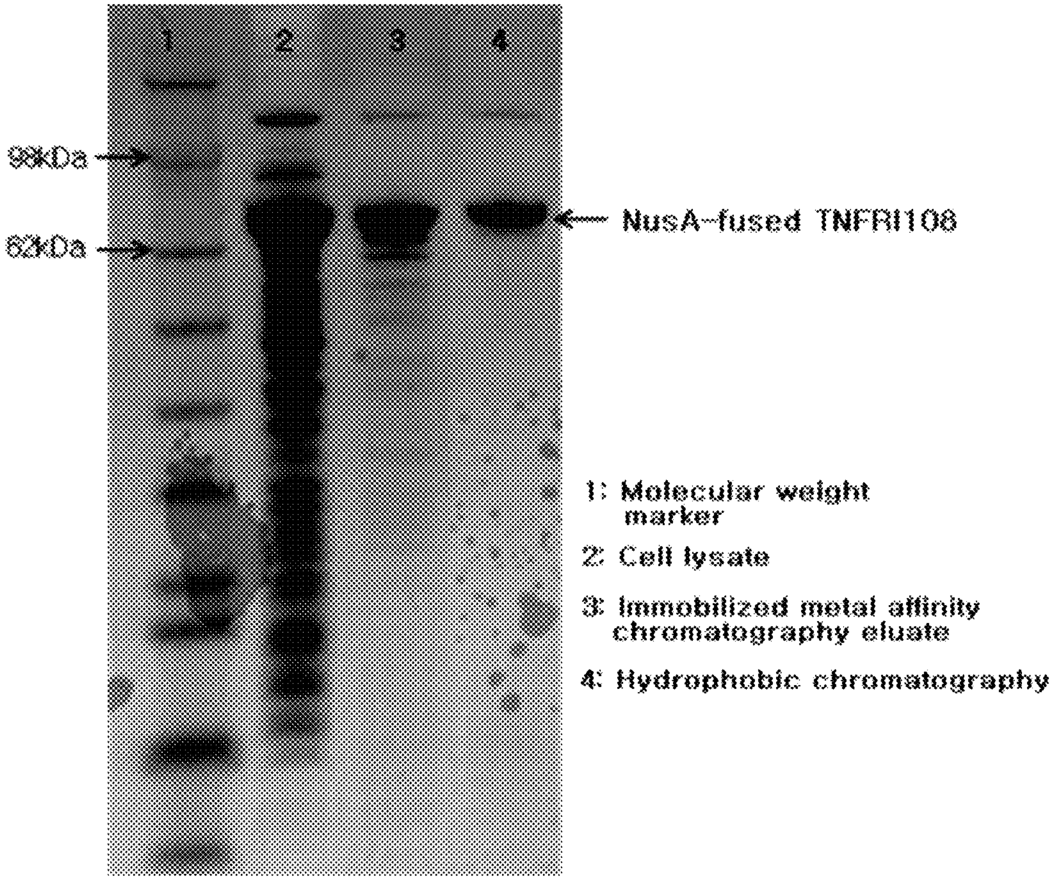
FIG. 2 is a photograph of NusA-fused TNFRI108 purified by immobilized metal affinity chromatography and hydrophobic interaction chromatography after expression of NusA-fused TNFRI108 in *E. coli* transformed with a pET44a-NusA-TNFRI108 expression vector.

A 1.0 M ammonium sulfate ($(NH_4)_2SO_4$) solution at a concentration of 400 mM was added to the protein solution eluted by immobilized metal affinity chromatography. 300 μl of a phenyl SEPHAROSE™ resin (Cat. No: 17-108201, GE) was loaded onto a 96-well filter plate, and a 6 column volume of an equilibration solution (20 mM sodium phosphate ($Na_2PO_4$), 400 mM ammonium sulfate, pH 7.0) was flowed thereto. An immobilized metal affinity chromatography eluant was added to the column, and a 2 column volume of an equilibration solution was flushed to remove the unbound protein. The plate was washed with a 10 column volume of a wash solution (20 mM sodium phosphate ($Na_2PO_4$), 160 mM ammonium sulfate, pH 7.0), followed by elution with a 6 column volume of an eluent solution (20 mM sodium phosphate, pH 7.0). The eluted sample was concentrated to 100 μg/mL or higher and quantified by Bradford assay. All of the purified samples were subjected to confirmation of purity by SDS-PAGE analysis (FIG. 2).

Experimental Example 1

Determination of Binding Ability Between Ligand (TNF-α) and TNFRI108

Figure 3:
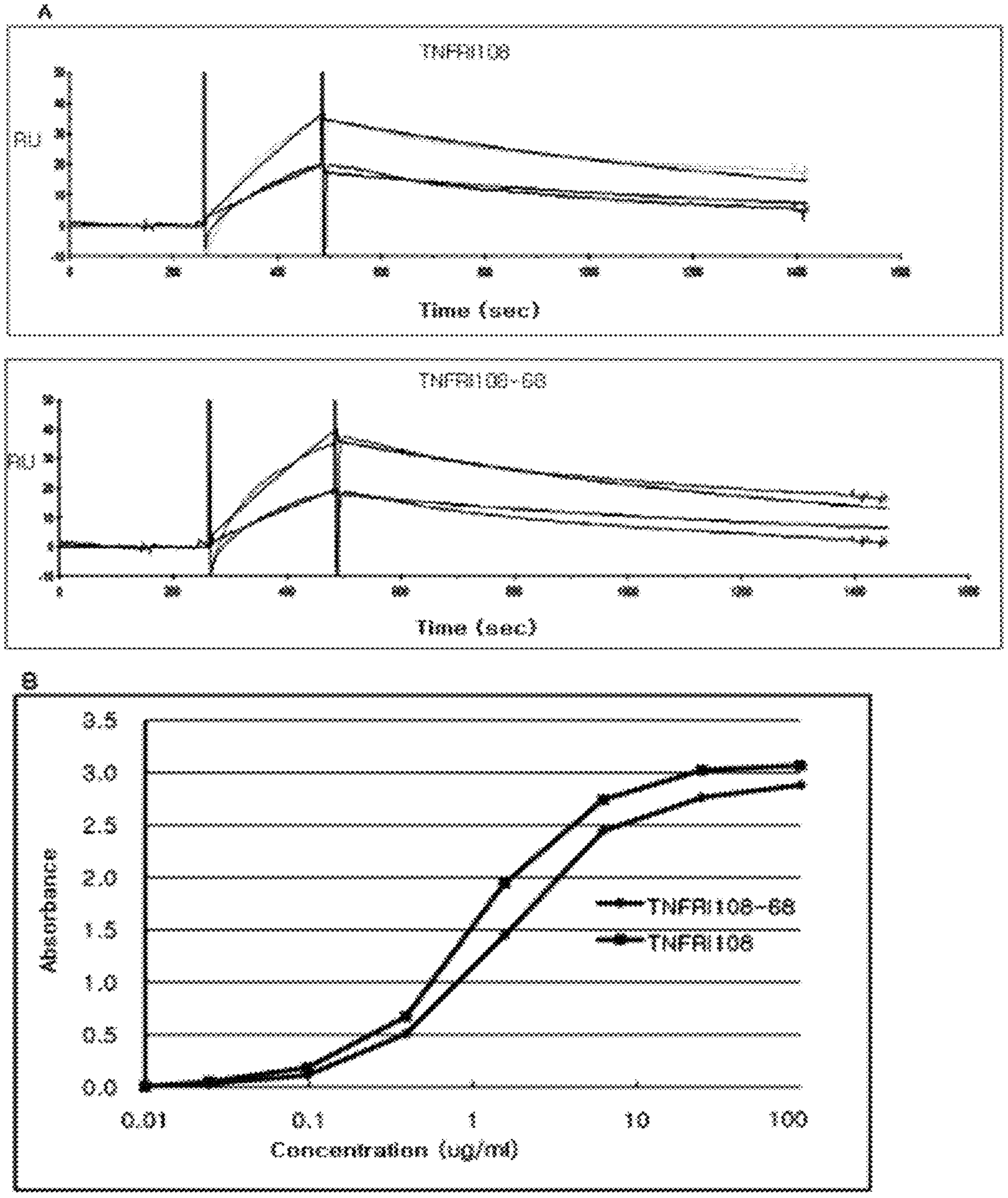
FIG. 3 is a graph confirming the results of BIACORE™ assay (3A) and ELISA (3B) for ability of a TNFRI108 fragment (control) and a TNFRI108 fragment single variant TNFRI108-68 to bind to TNF-α.

The TNFRI108 fragment and TNFRI108 single variant (TNFRI108-68) produced as an intracellular soluble protein were purified and separated by immobilized metal affinity chromatography and hydrophobic chromatography. The purified TNFRI108 fragment (control) and TNFRI108 fragment variant were quantified by means of Bradford assay, and ability thereof to bind with TNF-α was measured by means of ELISA and BIACORE™ assay (FIG. 3).

Specifically, the BIACORE™ assay was carried out in a BIACORE™ 3000 system using a CM5 chip. For the first cell of the chip, assay was carried out with no immobilization of TNF-α, activation with a 0.05 M NHS/0.2M EDC solution, and inactivation with 1.0 M ethanolamine hydrochloride (pH 8.5). For the second cell of the chip, TNF-α was immobilized to 800 RU for kinetic analysis. A CM5 chip was activated using a 0.05 M NHS/0.2M EDC solution, and TNF-α was immobilized to 800 RU. After 800 RU of TNF-α was immobilized, followed by reaction with 1.0 M ethanolamine hydrochloride (pH 8.5) to inactivate the chip. Analysis of each sample was carried out by deducting the first cell RU value of the chip from the second cell RU value of the chip while flowing a 25 mM Tris (pH 8.5) solution containing 100 mM NaCl at a flow rate of 15 μL/min. The sample was injected at a rate of 100 μg/mL and 50 μg/mL for 240 seconds in a kinetic mode, and the dissociation time was set to 900 seconds. For re-analysis, a wash solution (5 mM NaOH, 10 mM NaCl) was injected for 20 seconds in a Quickinject mode. The bindability was determined by processing the sensorgram results for two concentrations using the BIACORE™ results program (FIG. 3A). As confirmed in FIG. 3, the TNFRI108 single variant (TNFRI108-68) of the present invention exhibited binding ability comparable to that of TNFRI108.

Specifically, for performing ELISA, 100 μl of TNF-α was injected at a concentration of 1.0 μg/ml to a 96-well plate (Cat. No: 2592, Costar), followed by immobilization at 4° C. for 16 hours. The plate was washed three times with a wash solution (0.05% TWEEN™-20, 10 mM PBS, pH 7.4), followed by reaction in a PBS (pH 7.4) solution containing 1% BSA for 2 hours at room temperature. 100 μl of a sample was injected to each well at a concentration of about 1.5 μg/ml to 100 μg/mL, followed by reaction at room temperature for 2 hours. The plate was washed three times with a wash solution (0.05% TWEEN™-20, 10 mM PBS, pH 7.4), and 100 μl of mouse-derived TNFR complex antibodies (Cat. No: DY225, RnD) was injected thereto at a concentration of 200 ng/ml, followed by reaction at room temperature for 2 hours. The plate was washed three times with a wash solution, and 100 μl of a 200-fold dilution of HRP-conjugated secondary antibodies (Cat. No: DY225, RnD) was injected thereto, followed by reaction at room temperature for 15 minutes. The plate was washed three times with a wash solution, 100 μl of 3,3',5,5'-tetramethylbenzidine (Cat. No: DY999, RnD) which is a substrate solution was injected thereto, followed by reaction at room temperature for 15 minutes, and 50 μl of a 1.0 M sulfuric acid solution (Cat. No: S2129, Samchun Chemical) was injected to stop the reaction. Absorbance at 450 and 540 nm was read using a ELISA microplate reader (Model: VersaMax, MD). Ability of TNFRI108 to bind with TNF-α was confirmed by dose-dependent changes of absorbance (FIG. 3B).

Experimental Example 2

Determination of Protease Resistance of TNFRI108 and TNFRI108 Variants

Protease resistance of TNFRI108 fragment and TNFRI108 fragment variant was confirmed as follows. The total protein concentration of the purified liquid was measured, porcine pancreatin was treated to 24% of the quantity of the total protein (a value of the total protein of the purified TNFRI108 liquid quantified by Bradford assay), and the half-life of TNFRI108 fragment and TNFRI108 fragment variant was investigated to thereby confirm a TNFRI108 fragment variant having protease resistance as compared to the TNFRI108 polypeptide fragment.

Figure 4:
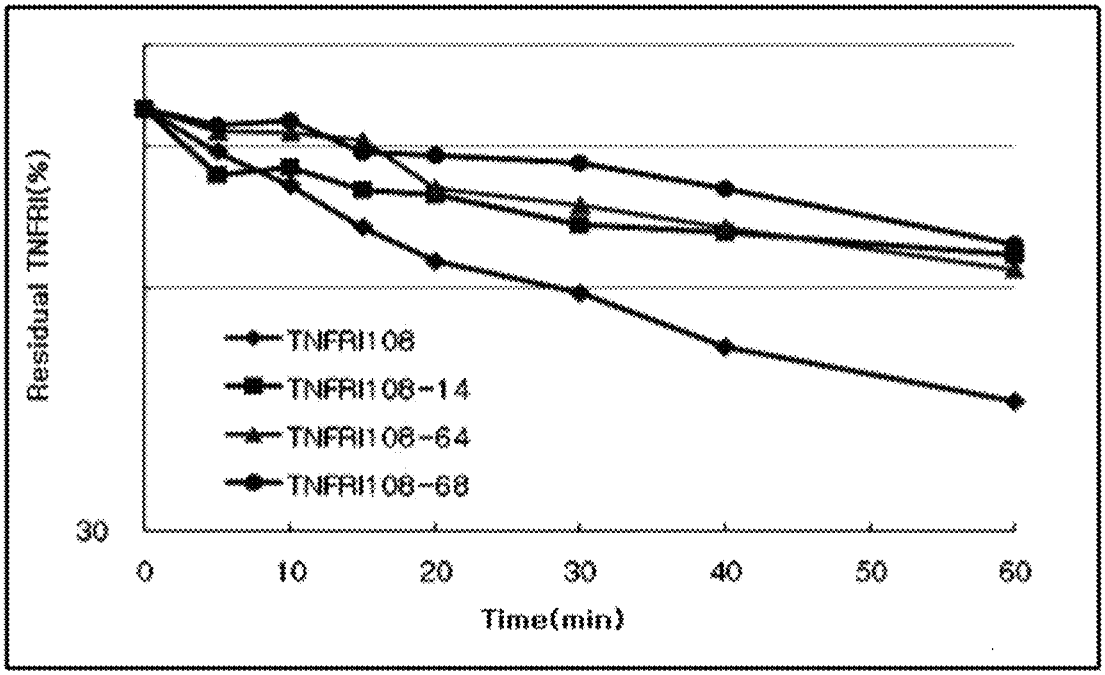
FIG. 4 is a graph confirming an increase in protease resistance of TNFRI108 fragment single variant TNFRI108-14, TNFRI108-64, and TNFRI108-68 vs. TNFRI108 fragment.

In order to identify a protease-resistant variant TNFRI108, a half-life of each variant after the treatment with pancreatin (Cat. No: P7545; Sigma) was determined and a variant having an increased half-life as compared to TNFRI108 was selected. The results of increased resistance of the representative variants TNFRI108-14, TNFRI108-64 and TNFRI108-68 against a treatment of pancreatin are shown in FIG. 4.

Specifically, TNFRI108 (control) and individual variants quantified by Bradford assay were adjusted to a concentration of 100 μg/ml using a PBS solution, and 250 μl of a protein sample was prepared in a 500 μl centrifugation tube. 30 μl of 0.1 M sodium phosphate containing 6 μg of pancreatin was added to the sample, followed by reaction at 37° C. After 0, 5, 10, 15, 20, 30, 40 and 60 minutes, 30 μl of the sample was taken and added to 270 μl of a 5% BSA solution containing 5 μl of a protease inhibitor (Cat. No: 11836170001, Roche), followed by mixing. The mixture was stored in liquid nitrogen. For the samples for which the experiment had finished, an uncleaved amount of each variant was analyzed by ELISA quantification (Cat. No: DY225, RnD) to calculate a half-life of TNFRI108 variants. By taking a half-life of TNFRI108 as a reference, a relative half-life of each variant was expressed in terms of percentage (Table 4).

TABLE 4

Protease resistance of TNFRI108 variants (reaction at 37° C.)

| Variant No. | Resistance of TNFRI108 variants vs. TNFRI108 |
|---|---|
| TNFRI108-1 | 73% |
| TNFRI108-2 | 48% |
| TNFRI108-3 | 5% |
| TNFRI108-4 | 6% |
| TNFRI108-5 | 26% |
| TNFRI108-6 | 57% |
| TNFRI108-7 | 108% |
| TNFRI108-8 | 111% |
| TNFRI108-9 | 43% |
| TNFRI108-10 | 14% |
| TNFRI108-11 | 24% |
| TNFRI108-12 | 30% |
| TNFRI108-13 | 166% |
| TNFRI108-14 | 168% |
| TNFRI108-15 | 14% |
| TNFRI108-16 | 13% |

TABLE 4-continued

Protease resistance of TNFRI108 variants (reaction at 37° C.)

| Variant No. | Resistance of TNFRI108 variants vs. TNFRI108 |
|---|---|
| TNFRI108-17 | 17% |
| TNFRI108-18 | 81% |
| TNFRI108-19 | 89% |
| TNFRI108-20 | 106% |
| TNFRI108-21 | ND |
| TNFRI108-22 | ND |
| TNFRI108-23 | ND |
| TNFRI108-24 | ND |
| TNFRI108-25 | 75% |
| TNFRI108-26 | 75% |
| TNFRI108-27 | 93% |
| TNFRI108-28 | 149% |
| TNFRI108-29 | ND |
| TNFRI108-30 | ND |
| TNFRI108-31 | 70% |
| TNFRI108-32 | 50% |
| TNFRI108-33 | 70% |
| TNFRI108-34 | 55% |
| TNFRI108-35 | 80% |
| TNFRI108-36 | 50% |
| TNFRI108-37 | 84% |
| TNFRI108-38 | 89% |
| TNFRI108-39 | 89% |
| TNFRI108-40 | 90% |
| TNFRI108-41 | 125% |
| TNFRI108-42 | 113% |
| TNFRI108-43 | 110% |
| TNFRI108-44 | 96% |
| TNFRI108-45 | 37% |
| TNFRI108-46 | 57% |
| TNFRI108-47 | 158% |
| TNFRI108-48 | 103% |
| TNFRI108-49 | 51% |
| TNFRI108-50 | 23% |
| TNFRI108-51 | 67% |
| TNFRI108-52 | 71% |
| TNFRI108-53 | 116% |
| TNFRI108-54 | 119% |
| TNFRI108-55 | 83% |
| TNFRI108-56 | 28% |
| TNFRI108-57 | 141% |
| TNFRI108-58 | 116% |
| TNFRI108-59 | 86% |
| TNFRI108-60 | 84% |
| TNFRI108-61 | 96% |
| TNFRI108-62 | 89% |
| TNFRI108-63 | 91% |
| TNFRI108-64 | 213% |
| TNFRI108-65 | 171% |
| TNFRI108-66 | 111% |
| TNFRI108-67 | 109% |
| TNFRI108-68 | 288% |
| TNFRI108-69 | 107% |
| TNFRI108-70 | 105% |
| TNFRI108-71 | 74% |
| TNFRI108-72 | 103% |
| TNFRI108-73 | 176% |
| TNFRI108-74 | 158% |
| TNFRI108-75 | 83% |
| TNFRI108-76 | 97% |

(ND: Not Detected)

Example 3

Construction of TNFRI126 Variants

(1) Construction of an Expression Vector Capable of Expressing Met-TNFRI126 or Met-TNFRI126 variants The selection of single variants using TNFRI108 was confirmed through Met-TNFRI126 and Met-TNFRI126 variants. For this purpose, variants 7, 8, 9, 10, 14, 64, 65, 68, 73, and 74 were produced in the form of Met-TNFRI126 and protease resistance thereof was confirmed.

Specifically, the construction of an *E. coli* expression vector for the expression of Met-TNFRI126 was completed by inserting a TNFRI126 gene into a pET44a vector. The TNFRI126 gene was obtained by PCR using PGEM™-TNFRI171 constructed in Preparation Example as a template, in combination with the following primers. NdeI and BamHI restriction enzyme sites were respectively added to 5' end and 3' end of the primer sequence, such that the TNFRI126 gene was expressed in the form of Met-TNFRI126 which is free from a NusA protein of a pET44a vector.

```
Forward primer:
5'-acatatggatagcgtgtgcccgc-3'

Reverse primer:
5'-cggatccttaacaaactgtattctgcttc-3'
```

PCR was carried out under the following conditions: primary denaturation at 98° C. for 5 minutes, 25 cycles of secondary denaturation at 98° C. for 30 seconds, primer annealing at 55° C. for 30 seconds and elongation at 72° C. for 1 minute, followed by final enzymatic reaction at 72° C. for 10 minutes. Restriction enzymes (NdeI and BamHI) were added to the amplified gene and the pET44a vector, followed by reaction at 37° C. for 3 hours. After treatment with the restriction enzymes, the reaction product was subjected to electrophoresis on 1% agarose gel, and the DNA band at the corresponding size position was excised from the agarose gel with a razor and extracted using a DNA isolation kit. 50 ng of the pET44a vector and 200 ng of the Met-TNFRI126 gene were added to the extract, 10 µl of 2× ligation premix was added thereto, finally sterile distilled water was added to make a volume of 20 µl, and reactants were reacted at room temperature for 5 minutes. 2 µl of the reaction liquid was taken and added to a BL21STAR™ (DE3) cell which was then transformed by applying heat shock at 47° C. 2 minutes, followed by static culture in an LB solid medium containing ampicillin to obtain a colony. The colony was cultured in an LB liquid medium containing ampicillin, and the plasmid was isolated. The gene sequence thereof was confirmed through gene sequence analysis. The thus-obtained plasmid was designated as a pET44a-Met-TNFRI126 plasmid (FIG. 5).

(2) Expression of Met-TNFRI126 and Met-TNFRI126 Variants

1 µl of the plasmid solution prepared as above was taken and added to a BL21STAR™ (DE3) (Cat. No: C6010-03, Invitrogen) competent cell which was then transformed by applying heat shock at 42° C. for 1 minute, followed by static culture in an LB solid medium containing ampicillin to obtain a colony. *E. coli* BL21STAR™ (DE3) containing the expression vector was inoculated onto 50 ml of a YP medium (yeast extract: Cat. No: 103753, Merck; peptone: Cat. No: 243620, BD; NaCl: Cat. No: 1064049025, Merck) containing 100 µg/ml of ampicillin, followed by aeration culture at 37° C. for 16 hours. The cultured medium was inoculated into a 1 L flask filled with 250 ml of a YP medium containing 100 µg/ml of ampicillin such that absorbance of 0.1 at 600 nm was achieved. When cultured at 37° C. to absorbance of 3 to 4 at 600 nm, IPTG was added at a final concentration of 1.0 mM to induce expression. After induction of expression, aeration culture was further continued at 37° C. for 3 hours, and the cultured cells were centrifuged at 6,000 rpm for 20 minutes to collect cells.

(3) Purification of Met-TNFRI126 and Met-TNFRI126 Variants

The collected cells were resuspended in a resuspension solution (50 mM Tris, 0.5 mM EDTA, pH 8.5). Lysis of the suspended cells was carried out by using a sonicator (Cat. No: VCX 750, Sonics). Cell lysis was followed by centrifugation at 8000×g and 10° C. for 30 minutes, the supernatant was discarded, and the precipitated pellet was suspended in a 35 mL pellet wash solution (50 mM Tris, 10 mM EDTA, 0.5% TRITON™ X-100, pH 8.0), followed by centrifugation at 8000×g and 10° C. for 20 minutes. The supernatant was discarded, and the pellet was resuspended in 35 mL of a resuspension solution, followed by centrifugation at 8000×g and 10° C. for 20 minutes. The washed pellet was used immediately or freeze-stored at −80° C.

6 mL of a denaturing solution (6 to 8 M urea or 6 to 8 M guanidine-HCl, 10 mM dithiothreitol (DTT), 2.0 mM EDTA, 0.2 M NaCl) was added to completely dissolve the pellet obtained above. Thereafter, the undissolved pellet was removed using a 0.45 μm syringe filter. The solubilized pellet solution was 20-fold diluted in a refolding solution (50 mM Tris, 1.0 mM EDTA, 0.5 M L-arginine, pH 7.5) and gently stirred at 4° C. for 12 to 24 hours to induce refolding.

For purification of the refolded Met-TNFRI126 and Met-TNFRI126 variants, the refolding solution was 20-fold concentrated using a 3 kD AMICON™ Ultra (Cat. No: UFC900324, Millipore). Then, purification was carried out by gel filtration chromatography with an XK25/70 (Cat. No: 19-0146-01, GE) column which was packed with a SUPERDEX™ 75 prep grade (GE) resin.

Figure 6:
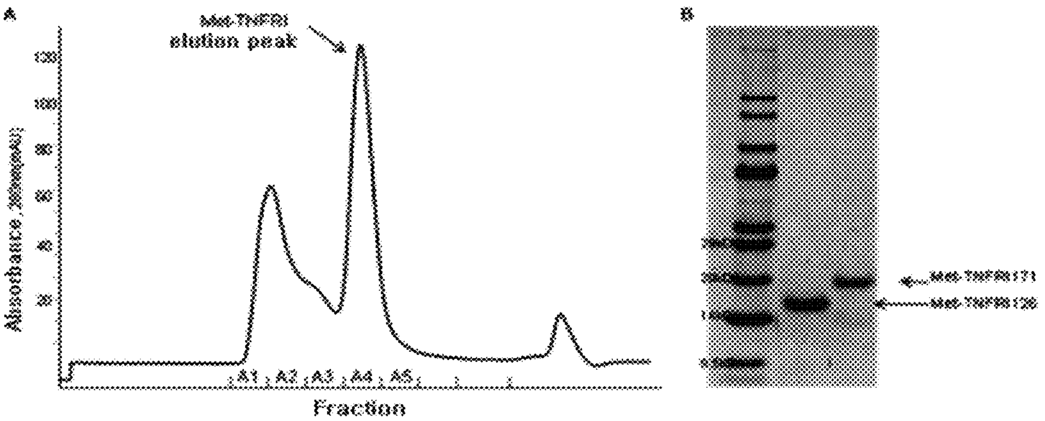
FIG. 6A is a view confirming elution of Met-TNFRI126 and Met-TNFRI171 protein by gel filtration chromatogram (fraction A4)
FIG. 6B is a photograph showing the SDS-PAGE analysis results of purified Met-TNFRI126 and Met-TNFRI171 under the reduced state.

Specifically, prior to loading of the refolded sample into a column, the column was equilibrated using 4 to 5 column volume of an equilibration solution (50 mM sodium phosphate, 100 mM NaCl, pH 7.0). After 2 mL of the sample was loaded into the column, samples were aliquoted at a volume of 5 mL/fractionation while flowing the equilibration solution at a flow rate of 5.0 mL/min. The collected samples were analyzed by SDS-PAGE, and only the fractions having a purity of more than 90% were taken (FIG. 6). Met-TNFRI126 and Met-TNFRI126 variants were purified in the same manner as above.

Experimental Example 3

Determination of Ability of Met-TNFRI126 and Met-TNFRI126 variant to bind to Ligand (TNF-α)

The concentration of the purified Met-TNFRI126 (control) and Met-TNFRI126 variants having a purity of more than 90% was quantified by Bradford assay, and the ability thereof to bind to TNF-α was confirmed by ELISA.

100 μl of TNFRI190 (a protein consisting of 190 amino acids extending from amino acid residue 22 to amino acid residue 211 of TNFRI as set forth in SEQ ID NO: 1, Cat No: 636-R1-025-CF, R&D) was loaded at a concentration of 1 μg/ml onto a 96-well plate, followed by immobilization at 4° C. for 16 hours. Each well was washed three times with 300 μl of a wash solution (0.05% TWEEN™-20, PBS, pH 7.4), and 300 μl of a blocking solution (5% skim milk, PBS, pH 7.4) was added to each well, followed by reaction at room temperature for 2 hours. Washing was then carried out in the same manner as described hereinbefore. Assay samples were prepared at different concentrations of 500 nM, 125 nM, 31 nM, 7.8 nM, 1.9 nM, 0.48 nM, 0.12 nM and 0.03 nM and then loaded at a dose of 100 μl/well in duplicate. 100 μl of TNF-α was added to each of the sample-loaded wells at a dose of 50 ng/ml, followed by reaction at room temperature for 2 hours. After being washed with a wash solution, 100 μg/mL of the TNF-α antibody solution was diluted to 1/1000 and then added at a dose of 100 μl/well, followed by reaction at room temperature for 2 hours. After being washed with a wash solution, a substrate solution was added thereto at a dose of 100 μl/well, followed by reaction at room temperature for 15 minutes, 100 μl of 3,3',5,5'-tetramethylbenzidine (Cat. No: DY999, RnD) which is a substrate solution was injected thereto, followed by reaction at room temperature for 15 minutes, and 50 μl of a 1.0M sulfuric acid solution (Cat. No: 52129, Samchun Chemical) was injected to stop the reaction. Absorbance at 450 and 540 nm was read using a ELISA microplate reader (Model: VersaMax, MD).

Figure 7:
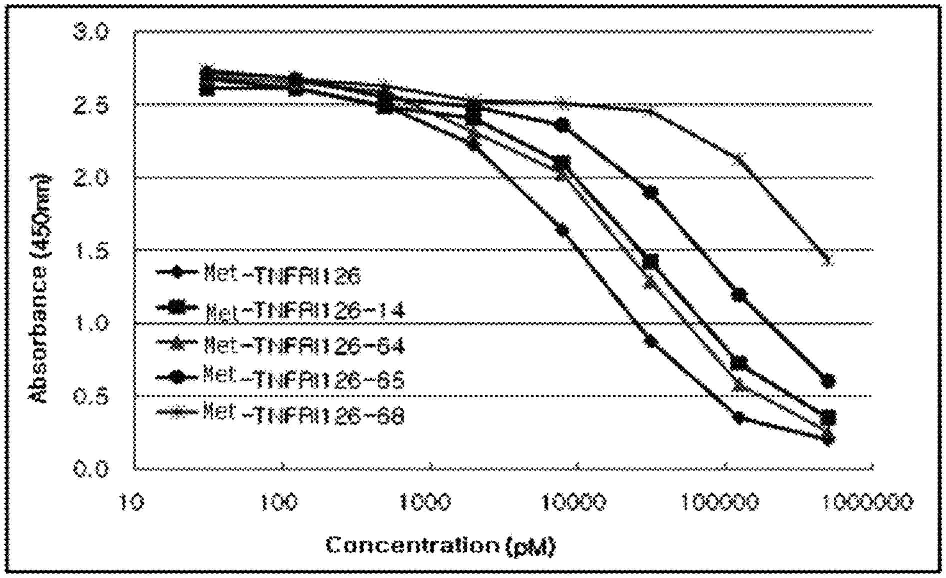
FIG. 7 is a graph confirming the ELISA results for ability of Met-TNFRI126 fragment (control), Met-TNFRI126 fragment variants Met-TNFRI126-14, Met-TNFRI126-64, Met-TNFRI126-65, and Met-TNFRI126-68 to bind to TNF-α.

Binding ability of Met-TNFRI126 and Met-TNFRI126 variant was confirmed by dose-dependent changes of absorbance (FIG. 7).

Experimental Example 4

Determination of Protease Resistance of Met-TNFRI126 and Met-TNFRI126 Variants

The protease resistance was evaluated in the same manner as in Experimental Example 2, except that Met-TNFRI126 or Met-TNFRI126 variant was used in place of TNFRI108 (Table 5). Variants 14, 64, 68, 73 and 74 which had measured to have high protease resistance in TNFRI108 exhibited the same high protease resistance, whereas variants 9 and 10 which had measured to have low protease resistance in TNFR108 exhibited low protease resistance.

TABLE 5

Protease resistance of Met-TNFRI126 variants vs. Met-TNFRI126

| Variant No. | Resistance (%) of Met-TNFRI126 variants vs. Met-TNFRI126 |
|---|---|
| TNFRI126-7 | 87% |
| TNFRI126-8 | 95% |
| TNFRI126-9 | 65% |
| TNFRI126-10 | 30% |
| TNFRI126-14 | 143% |
| TNFRI126-64 | 152% |
| TNFRI126-65 | 99% |
| TNFRI126-68 | 120% |
| TNFRI126-73 | 159% |
| TNFRI126-74 | 169% |

Example 4

Construction of TNFRI171 Variants (1) Construction of an Expression Vector Capable of Expressing Met-TNFRI171 or Met-TNFRI171 Variants Among single variants designed in Example 1, single variants present in the fourth domain of TNFRI were produced as Met-TNFRI171 and evaluated.

For this purpose, an expression vector capable of expressing Met-TNFRI171 or Met-TNFRI171 variants in *E. coli* was constructed.

Specifically, the Met-TNFRI171 gene (SEQ ID NO: 267) was obtained by PCR using the PGEM™-TNFRI171 plasmid constructed in Preparation Example as a template. At this time, for cloning into a pET44a vector, NdeI and BamHI restriction enzyme recognition sites were respectively added to 5' end and 3' end of the gene.

Primers used for PCR amplification are as follows.

Forward primer:
5'-acatatggatagcgtgtgcccgc-3'

Reverse primer:
5'-cggatccttatgtggtgcctgagtcctc-3'

PCR was carried out under the following conditions: primary denaturation at 98° C. for 5 minutes, 25 cycles of secondary denaturation at 98° C. for 30 seconds, primer annealing at 55° C. for 30 seconds and elongation at 72° C. for 1 minute, followed by final enzymatic reaction at 72° C. for 10 minutes. Restriction enzymes (NdeI and BamHI) were added to the amplified gene and the pET44a vector, followed by reaction at 37° C. for 3 hours. After treatment with the restriction enzymes, the reaction product was subjected to electrophoresis on 1% agarose gel, and the DNA band at the corresponding size position was excised from the agarose gel with a razor and extracted using a DNA isolation kit. 50 ng of the pET44a vector and 200 ng of the Met-TNFRI171 gene were added to the extract, 10 μl of 2× ligation premix was added thereto, finally sterile distilled water was added to make a volume of 20 μl, and reactants were reacted at room temperature for 5 minutes. 2 μl of the reaction liquid was taken and added to a BL21STAR™ (DE3) cell which was then transformed by applying heat shock at 47° C. 1 minutes, followed by static culture in an LB solid medium containing ampicillin to obtain a colony. The colony was cultured in an LB liquid medium containing ampicillin, and the plasmid was isolated. The gene sequence thereof was confirmed through gene sequence analysis. The thus-obtained plasmid was designated as a pET44a-Met-TNFRI171 plasmid.

Met-TNFRI171 variants were constructed by PCR using the pET44a-Met-TNFRI171 plasmid as a template, in combination with primers corresponding to each of variants listed in Table 6.

TABLE 6

Primers for site-directed mutagenesis

| Variant No. | Variation | Primer direction | Primer sequence |
|---|---|---|---|
| TNFRI-77 | L150I | Forward | 5'-aattgctccctgtgtattaacggcactgtgcatc-3' |
| | | Reverse | 5'-gatgcacagtgccgttaatacacagggagcaatt-3' |
| TNFRI-78 | L150V | Forward | 5'-ttaattgctccctgtgtgtgaacggcactgtgca-3' |
| | | Reverse | 5'-tgcacagtgccgttcacacacagggagcaattaa-3' |
| TNFRI-79 | L156I | Forward | 5'-gaacggcactgtgcatatttcctgtcaggagaag-3' |
| | | Reverse | 5'-cttctcctgacaggaaatatgcacagtgccgttc-3' |
| TNFRI-80 | L156V | Forward | 5'-tgaacggcactgtgcatgtgtcctgtcaggagaa-3' |
| | | Reverse | 5'-ttctcctgacaggacacatgcacagtgccgttca-3' |
| TNFRI-81 | E160Q | Forward | 5'-gcatctgtcctgtcagcagaagcagaatacagtt-3' |
| | | Reverse | 5'-aactgtattctgcttctgctgacaggacagatgc-3' |
| TNFRI-82 | E160N | Forward | 5'-gcatctgtcctgtcagaacaagcagaatacagtt-3' |
| | | Reverse | 5'-aactgtattctgcttgttctgacaggacagatgc-3' |
| TNFRI-83 | K161Q | Forward | 5'-atctgtcctgtcaggagcagcagaatacagtttg-3' |
| | | Reverse | 5'-caaactgtattctgctgctcctgacaggacagat-3' |
| TNFRI-84 | K161N | Forward | 5'-ctgtcctgtcaggagaaccagaatacagtttgta-3' |
| | | Reverse | 5'-tacaaactgtattctggttctcctgacaggacag-3' |
| TNFRI-85 | E200Q | Forward | 5'-ttgtgcctaccccagattcagaatgttaagggca-3' |
| | | Reverse | 5'-tgcccttaacattctgaatctggggtaggcacaa-3' |
| TNFRI-86 | E200N | Forward | 5'-gtgcctaccccagattaacaatgttaagggcact-3' |
| | | Reverse | 5'-agtgcccttaacattgttaatctggggtaggcac-3' |
| TNFRI-87 | K203Q | Forward | 5'-ccccagattgagaatgttcagggcactgaggac-3' |
| | | Reverse | 5'-gtcctcagtgccctgaacattctcaatctgggg-3' |
| TNFRI-88 | K203N | Forward | 5'-cccagattgagaatgttaacggcactgaggactc-3' |
| | | Reverse | 5'-gagtcctcagtgccgttaacattctcaatctggg-3' |
| TNFRI-89 | E206Q | Forward | 5'-ttgagaatgttaagggcactcaggactcaggcac-3' |
| | | Reverse | 5'-gtgcctgagtcctgagtgcccttaacattctcaa-3' |
| TNFRI-90 | E206N | Forward | 5'-aatgttaagggcactaacgactcaggcaccacat-3' |
| | | Reverse | 5'-atgtggtgcctgagtcgttagtgcccttaacatt-3' |
| TNFRI-91 | D207Q | Forward | 5'-gttaagggcactgagcagtcaggcaccacataag-3' |
| | | Reverse | 5'-cttatgtggtgcctgactgctcagtgcccttaac-3' |
| TNFRI-92 | D207N | Forward | 5'-atgttaagggcactgagaactcaggcaccacata-3' |
| | | Reverse | 5'-tatgtggtgcctgagttctcagtgcccttaacat-3' |

The composition of the solution used in the amplification reaction is as follows. 1.0 μl of pET44a-Met-TNFRI171 template plasmid DNA, 1.0 μl of each of 20 pmol forward primers, 1.0 μl of each of 20 pmol reverse primers, 25.0 μl of 2× PRIMESTAR™ PCR buffer, 4.0 μl of each of 200 μM dNTPs, 0.5 μl of PrimeSTAR HS DNA polymerase (Cat. No: R044A, Takara) and 17.5 μl of distilled water were added to make 50.0 μl of a reaction solution.

PCR was carried out under the following conditions: primary denaturation at 98° C. for 5 minutes, 17 cycles of secondary denaturation at 98° C. for 30 seconds, primer annealing at 55° C. for 30 seconds and elongation at 72° C. for 9 minutes, followed by final enzymatic reaction at 72 r for 10 minutes.

The PCR product was treated with a DpnI enzyme at 37° C. for 2 hours to degrade the *E. coli*-derived DNA and obtain the PCR-amplified DNA. 2 μl of the DNA solution was taken and added to an XL1-blue competent cell (Cat. No: RH119-J80, RBC) which was then transformed by applying heat shock at 42° C. for 1 minute, followed by static culture in an LB solid medium containing ampicillin to obtain a colony. The colony was cultured in an LB liquid medium containing ampicillin, and the plasmid was isolated and subjected to nucleotide sequencing analysis to confirm the completion of site-specific mutation.

(2) Expression of Met-TNFRI171 and Met-TNFRI171 Variants

The constructed Met-TNFRI171 and Met-TNFRI171 variant plasmids were extracted and then subjected to induction of expression according to the method of Example 3-(2). The expression was carried out in the same manner as in Example 3-(2), except that Met-TNFRI171 was used in place of Met-TNFRI126.

(3) Purification of Met-TNFRI171 and Met-TNFRI171 Variants

The expressed Met-TNFRI171 and Met-TNFRI171 variants were purified according to the method of Example 3-(3). The purification was carried out in the same manner as in Example 3-(3), except that Met-TNFRI171 was used in place of Met-TNFRI126 (FIG. 6).

Experimental Example 5

Determination of Ability of Met-TNFRI171 and Met-TNFRI171 Variants to Bind to Ligand (TNF-α)

Figure 8:
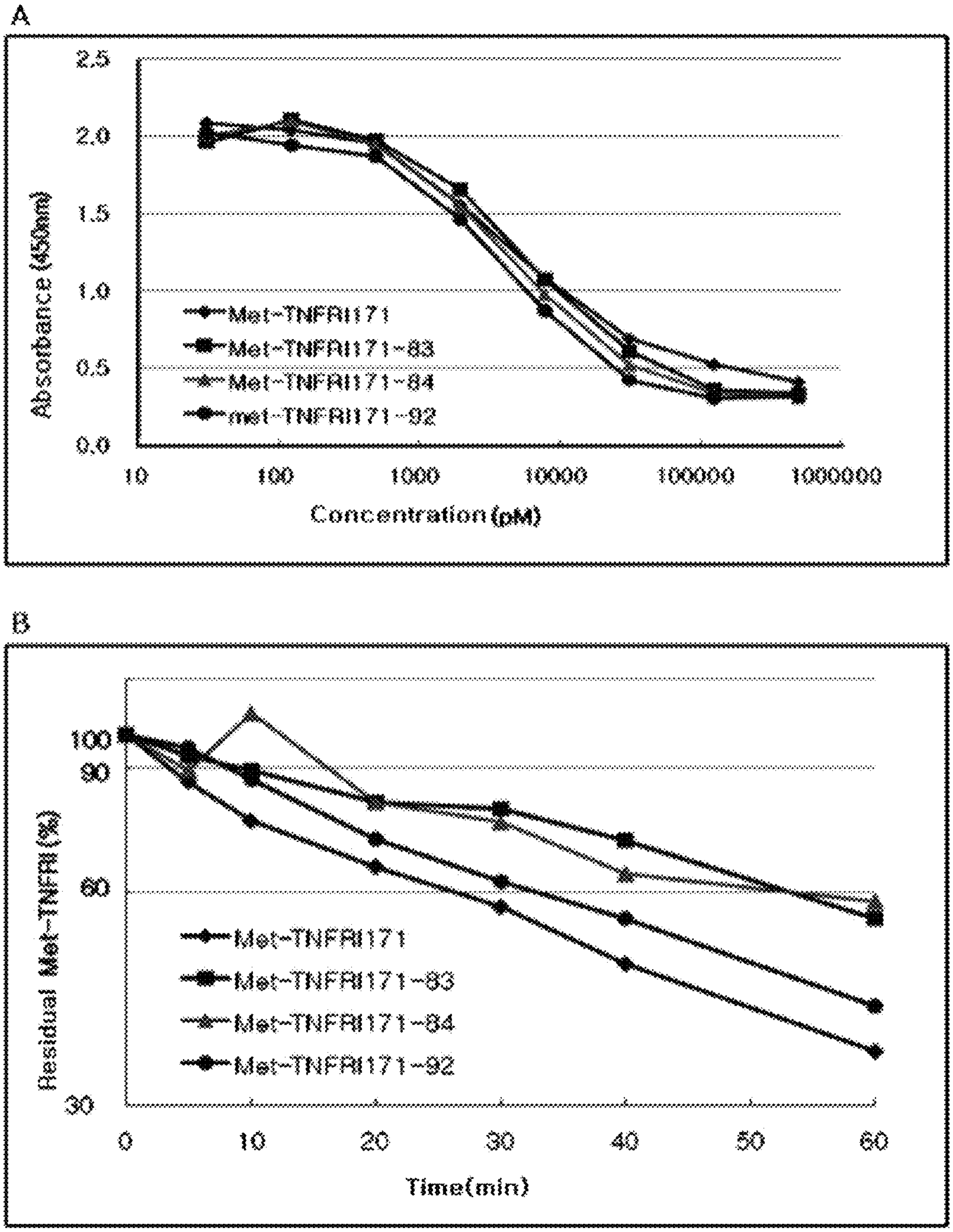
FIG. 8A is a view showing the assay results for ability of Met-TNFRI171 fragment (control), Met-TNFRI171 fragment variants Met-TNFRI171-83, Met-TNFRI171-84, and Met-TNFRI171-92 to bind to TNF-α.
FIG. 8B is a graph confirming an increase in protease resistance of Met-TNFRI171 fragment single variants Met-TNFRI171-83, Met-TNFRI171-84, and Met-TNFRI171-92 vs. Met-TNFRI171 fragment.

Activity evaluation was carried out in the same manner as in Experimental Example 3, except that Met-TNFRI171 was used in place of Met-TNFRI126. The measurement results of the bindability of the representative variants Met-TNFRI171-83, Met-TNFRI171-84 and Met-TNFRI171-92 are shown in FIG. 8A.

Experimental Example 6

Determination of Protease Resistance of Met-TNFRI171 and Met-TNFRI171 Variants The protease resistance was evaluated in the same manner as in Experimental Example 2, except that Met-TNFRI171 or Met-TNFRI171 variant was used in place of TNFRI108 (Table 7). The measurement results of increased resistance of the representative variants Met-TNFRI171-83, Met-TNFRI171-84 and Met-TNFRI171-92 against a treatment of pancreatin are shown in FIG. 8B.

TABLE 7

Protease resistance of Met-TNFRI171 variants vs. Met-TNFRI171

| Variant No. | Resistance of Met-TNFRI171 variants vs. Met-TNFRI171 |
|---|---|
| TNFRI171-77 | 120% |
| TNFRI171-78 | 87% |
| TNFRI171-79 | 113% |
| TNFRI171-80 | 103% |
| TNFRI171-81 | 57% |
| TNFRI171-82 | 68% |
| TNFRI171-83 | 187% |
| TNFRI171-84 | 187% |
| TNFRI171-85 | 116% |
| TNFRI171-86 | 90% |
| TNFRI171-87 | 111% |
| TNFRI171-88 | 99% |
| TNFRI171-89 | 114% |
| TNFRI171-90 | 102% |
| TNFRI171-91 | 117% |
| TNFRI171-92 | 127% |

Example 5

Design of TNFRI Double Variants

Further, the present inventors have designed double variants having substitution of two amino acids by combination of mutations having improved stability among single variants. The double variants were designed by combining variants 14, 64, 74, 83, 84, 85 and 92 exhibiting remarkable increased protease resistance among single variants. The design list of double variants is given in Table 8.

TABLE 8

Design list of double variants

| Variant No. | Variation |
|---|---|
| TNFRI171-201 | L68V/R133Q |
| TNFRI171-202 | L68V/F141V |
| TNFRI171-203 | R133Q/F141V |
| TNFRI171-204 | L68V/K161Q |
| TNFRI171-205 | L68V/K161N |
| TNFRI171-206 | L68V/D207N |
| TNFRI171-207 | K161Q/D207N |
| TNFRI171-208 | L68V/E200Q |
| TNFRI171-209 | E200Q/D207N |

Example 6

Construction of Met-TNFRI171 Double Variants

(1) Construction of an Expression Vector Capable of Expressing Met-TNFRI171 Double Variant The double variants designed in Example 5 were produced as Met-TNFRI171 and evaluated. For this purpose, an expression vector capable of expressing Met-TNFRI171 double variants in *E. coli* was constructed.

Specifically, with respect to variants 201, 202, 204, 205, 206 and 208 among the double variants listed in Table 8, DNA encoding a double variant was constructed by PCR using the plasmid of the Met-TNFRI171-14 single variant as a template, in combination with primers given in Table 9. Among the double variants, DNA encoding a double variant was constructed by PCR using the plasmid of the Met-TNFRI171-64 single variant as a template for variant 203, the plasmid of the Met-TNFRI171-83 single variant as a template for variant 207, and the plasmid of the Met-TNFRI171-85 single variant as a template for variant 209, in combination with primers given in Table 9.

The composition of the solution used in the amplification reaction is as follows. 1.0 μl of each of the template plasmid DNAs described above, 1.0 μl of each of 20 pmol forward primers, 1.0 μl of each of 20 pmol reverse primers, 25.0 μl of 2× PRIMESTAR™ PCR buffer, 4.0 μl of each of 200 μM dNTPs, 0.5 μl of PRIMESTAR™ HS DNA polymerase (Cat. No: R044A, Takara) and 17.5 μl of distilled water were added to make 50.0 μl of a reaction solution.

PCR was carried out under the following conditions: primary denaturation at 98° C. for 5 minutes, 17 cycles of secondary denaturation at 98° C. for 30 seconds, primer annealing at 55° C. for 30 seconds and elongation at 72° C. for 9 minutes, followed by final enzymatic reaction at 72° C. for 10 minutes.

TABLE 9

Primers for double mutagenesis

| Variant No. | Variation | Primer direction | Primer sequence |
|---|---|---|---|
| TNFRI17 1-201 | L68V/R133Q | Forward | 5'-gccgtaaaaaccagtatcagcattattggtcag-3' |
| | | Reverse | 5'-ctgaccaataatgctgatactggtttttacggc-3' |
| TNFRI17 1-202 | L68V/F141V | Forward | 5'-ggtcagaaaacctggtgcagtgttttaattgctc-3' |
| | | Reverse | 5'-gagcaattaaaacactgcaccaggttttctgacc-3' |
| TNFRI17 1-203 | R133Q/F141V | Forward | 5'-ggtcagaaaacctggtgcagtgttttaattgctc-3' |
| | | Reverse | 5'-gagcaattaaaacactgcaccaggttttctgacc-3' |
| TNFRI17 1-204 | L68V/K161Q | Forward | 5'-atctgtcctgtcaggagcagcagaatacagtttg-3' |
| | | Reverse | 5'-caaactgtattctgctgctcctgacaggacagat-3' |
| TNFRI17 1-205 | L68V/K161N | Forward | 5'-ctgtcctgtcaggagaaccagaatacagtttgta-3' |
| | | Reverse | 5'-tacaaactgtattctggttctcctgacaggacag-3' |
| TNFRI17 1-206 | L68V/D207N | Forward | 5'-atgttaagggcactgagaactcaggcaccacata-3' |
| | | Reverse | 5'-tatgtggtgcctgagttctcagtgcccttaacat-3' |
| TNFRI17 1-207 | K161Q/D207N | Forward | 5'-atgttaagggcactgagaactcaggcaccacata-3' |
| | | Reverse | 5'-tatgtggtgcctgagttctcagtgcccttaacat-3' |
| TNFRI17 1-208 | L68V/E200Q | Forward | 5'-ttgtgcctaccccagattcagaatgttaagggca-3' |
| | | Reverse | 5'-tgcccttaacattctgaatctggggtaggcacaa-3' |
| TNFRI17 1-209 | E200Q/D207N | Forward | 5'-atgttaagggcactgagaactcaggcaccacata-3' |
| | | Reverse | 5'-tatgtggtgcctgagttctcagtgcccttaacat-3' |

The PCR product was treated with a DpnI enzyme at 37° C. for 2 hours to degrade the *E. coli*-derived DNA and obtain the PCR-amplified DNA. 1 μl of the DNA solution was taken and added to an XL1-blue competent cell which was then transformed by applying heat shock at 42° C. for 1 minute, followed by static culture in an LB solid medium containing ampicillin to obtain a colony. The colony was cultured in an LB liquid medium containing ampicillin, and the plasmid was isolated and subjected to nucleotide sequencing analysis to confirm the completion of site-specific mutation.

(2) Expression of Met-TNFRI171 Double Variants

The constructed Met-TNFRI171 double variant plasmids were extracted and then subjected to induction of expression according to the method of Example 3-(2). The expression was carried out in the same manner as in Example 3-(2), except that a Met-TNFRI171 double variant was used in place of Met-TNFRI126.

(3) Purification of Met-TNFRI171 Double Variants

The expressed Met-TNFRI171 double variants were purified according to the method of Example 3-(3). The purification was carried out in the same manner as in Example 3-(3), except that a Met-TNFRI171 double variant was used in place of Met-TNFRI126.

Experimental Example 7

Determination of Ability of Met-TNFRI171 Double Variants to Bind to Ligand (TNF-α)

Figure 9:
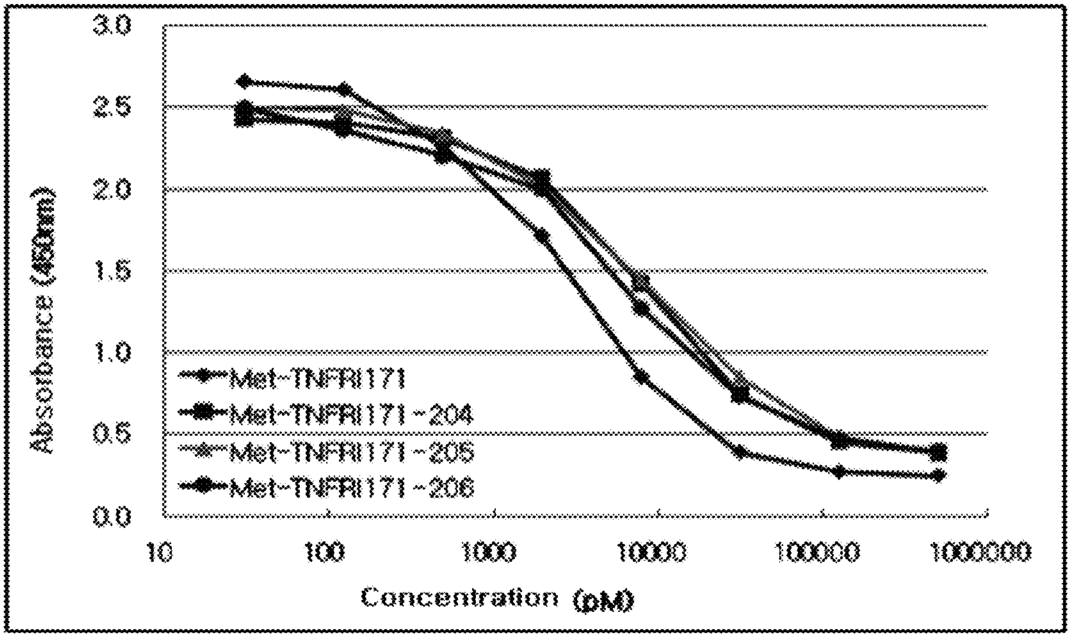
FIG. 9 is a graph confirming the ELISA results for ability of Met-TNFRI171 fragment (control), Met-TNFRI171 fragment double variants Met-TNFRI171-204, Met-TNFRI171-205, and Met-TNFRI171-206 to bind to TNF-α.

Activity evaluation was carried out in the same manner as in Experimental Example 3, except that a Met-TNFRI171 double variant was used in place of Met-TNFRI126. The measurement results of the bindability of the representative double variants Met-TNFRI171-204, Met-TNFRI171-205 and Met-TNFRI171-206 are shown in FIG. 9.

Experimental Example 8

Protease Resistance of Met-TNFRI171 Double Variants

Figure 10:
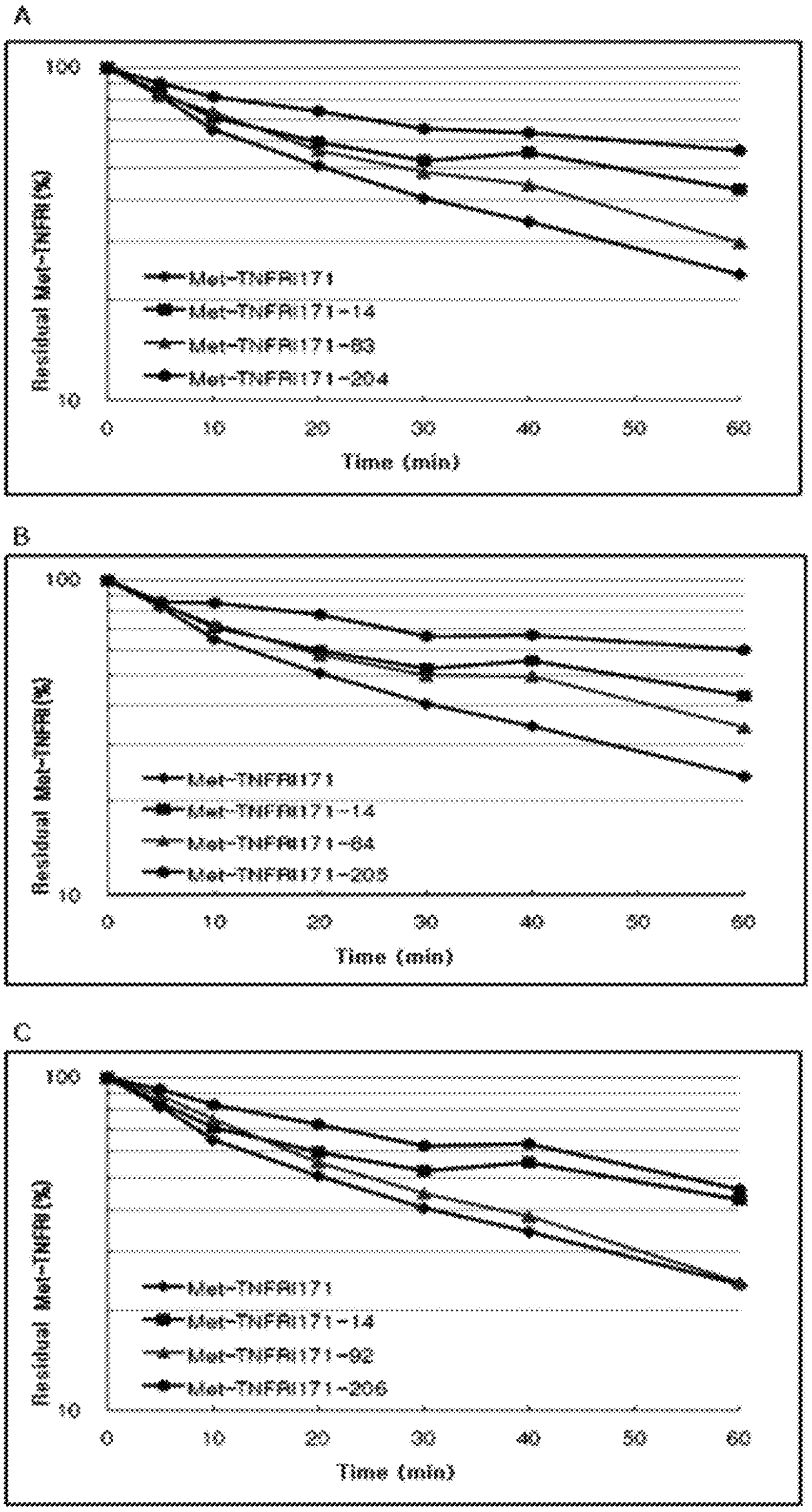
FIG. 10 is a graph confirming an increase in protease resistance of Met-TNFRI171 fragment double variants Met-TNFRI171-204 (10A), Met-TNFRI171-205 (10B), and Met-TNFRI171-206 (10C) vs. Met-TNFRI171 fragment.

The protease resistance was evaluated in the same manner as in Experimental Example 2, except that a Met-TNFRI171 double variant was used in place of TNFRI108 (Table 10). The measurement results of increased resistance of the representative double variants Met-TNFRI171-204, Met-TNFRI171-205 and Met-TNFRI171-206 against a treatment of pancreatin are shown in FIG. 10.

TABLE 10

| Protease resistance of Met-TNFRI171 double variants vs. Met-TNFRI171 | |
|---|---|
| Variant No. | Resistance of Met-TNFRI171 variants vs. Met-TNFRI171 |
| TNFRI171-201 | 101% |
| TNFRI171-202 | 51% |
| TNFRI171-203 | 50% |
| TNFRI171-204 | 224% |
| TNFRI171-205 | 251% |

TABLE 10-continued

| Protease resistance of Met-TNFRI171 double variants vs. Met-TNFRI171 | |
|---|---|
| Variant No. | Resistance of Met-TNFRI171 variants vs. Met-TNFRI171 |
| TNFRI171-206 | 212% |
| TNFRI171-207 | 100% |
| TNFRI171-208 | 115% |
| TNFRI171-209 | 94% |

What is claimed is:

1. A modified human tumor necrosis factor receptor-1 polypeptide, comprising an amino acid sequence selected from the group consisting of:

an amino acid sequence having one or more amino acid modifications selected from the group consisting of L150I, K161Q, K161N, D207N, L68V/K161Q, L68V/K161N and L68V/D207N in the amino acid sequence consisting of amino acid residues 41-211 of the amino acid sequence of a native human tumor necrosis factor receptor-I as set forth in SEQ ID NO: 1;

an amino acid sequence having one or more amino acid modifications selected from the group consisting of L68V, R133Q, W136S, F141I and F141V in the amino acid sequence consisting of amino acid residues 41-166 of the amino acid sequence of a native human tumor necrosis factor receptor-I as set forth in SEQ ID NO: 1; and an amino acid sequence having one or more amino acid modifications selected from the group consisting of positions L68I, L68V, E85N, R106H, R128H, R133Q, Y135I, W136S, F141I and F141V in the amino acid sequence consisting of amino acid residues 41-148 of the amino acid sequence of a native human tumor necrosis factor receptor-I as set forth in SEQ ID NO: 1.

2. The modified human tumor necrosis factor receptor-I polypeptide of claim 1, which comprises the amino acid sequence selected from the group consisting of SEQ ID NOS: 18, 19, 33, 46, 62, 69, 70, 73, 78, 79, 95, 145, 149, 154, 155, 242, 248, 249, 257, 261, 262 and 263.

3. The modified human tumor necrosis factor receptor-I polypeptide of claim 1, which comprises the amino acid sequence selected from the group consisting of SEQ ID NOS: 18, 19, 69, 70, 78, 95, 145, 154, 248, 249, 261, 262 and 263.

4. The modified human tumor necrosis factor receptor-I polypeptide of claim 1, 2 or 3, which has improved resistance to protease compared to the native human tumor necrosis factor receptor-I, when measured under the same conditions.

5. A complex of a human tumor necrosis factor receptor-I polypeptide formed by covalently linking two or three or more of the human tumor necrosis factor receptor-I polypeptides of claim 1, 2 or 3.

6. The modified human tumor necrosis factor receptor-I polypeptide of claim 1, 2 or 3 wherein the human tumor necrosis factor receptor-I polypeptide contains an additional modification of glycosylation, acylation, methylation, phosphorylation, hesylation, carbamylation, sulfation, prenylation, oxidation, guanidination, amidination, carbamylation, trinitrophenylation, nitration or pegylation.

7. A pharmaceutical preparation comprising the human tumor necrosis factor receptor-I polypeptide of claim 1, 2 or 3.

8. A pharmaceutical composition comprising the human tumor necrosis factor receptor-I polypeptide of claim 1, 2 or 3 and a pharmaceutically acceptable carrier.

* * * * *

SEQUENCE LISTING

```
<160> NUMBER OF SEQ ID NOS: 269

<210> SEQ ID NO 1
<211> LENGTH: 455
<212> TYPE: PRT
<213> ORGANISM: Homo sapiens
<220> FEATURE:
<221> NAME/KEY: PEPTIDE
<222> LOCATION: (1)..(445)

<400> SEQUENCE: 1

Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
             20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270
```

```
Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 2
<211> LENGTH: 171
<212> TYPE: PRT
<213> ORGANISM: Homo sapiens
<220> FEATURE:
<221> NAME/KEY: PEPTIDE
<222> LOCATION: (1)..(171)

<400> SEQUENCE: 2

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
```

165 170

<210> SEQ ID NO 3
<211> LENGTH: 126
<212> TYPE: PRT
<213> ORGANISM: Homo sapiens
<220> FEATURE:
<221> NAME/KEY: PEPTIDE
<222> LOCATION: (1)..(126)

<400> SEQUENCE: 3

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 4
<211> LENGTH: 108
<212> TYPE: PRT
<213> ORGANISM: Homo sapiens
<220> FEATURE:
<221> NAME/KEY: PEPTIDE
<222> LOCATION: (1)..(108)

<400> SEQUENCE: 4

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 5
<211> LENGTH: 516
<212> TYPE: DNA
<213> ORGANISM: Artificial Sequence
<220> FEATURE:
<223> OTHER INFORMATION: Synthetic construct of TNFRI171 for bacterial expression

<400> SEQUENCE: 5

-continued

```
gatagcgtgt gcccgcaggg taagtatatt catccgcaaa ataactctat ctgttgcaca     60

aagtgtcaca aagggacgta cctgtataat gactgtccgg ggccgggtca ggataccgac    120

tgccgcgagt gcgagagtgg gtcatttaca gcgagtgaga atcatctgcg ccactgcctg    180

agctgttcta agtgtcgtaa agagatgggc caagttgaaa tttcttcatg tacggtagac    240

cgcgatacgg tatgtggttg ccgtaaaaac cagtatcgcc attattggtc agaaaacctg    300

ttccagtgtt ttaattgctc cctgtgtctg aacggcactg tgcatctgtc ctgtcaggag    360

aagcagaata cagtttgtac ctgccatgca ggtttctttc taagagaaaa cgagtgtgtc    420

tcctgtagta actgtaagaa aagcctggag tgcacgaagt tgtgcctacc ccagattgag    480

aatgttaagg gcactgagga ctcaggcacc acataa                              516


<210> SEQ ID NO 6
<211> LENGTH: 108
<212> TYPE: PRT
<213> ORGANISM: Artificial Sequence
<220> FEATURE:
<223> OTHER INFORMATION: Synthetic construct of TNFRI108-1 (K48Q)

<400> SEQUENCE: 6

Asp Ser Val Cys Pro Gln Gly Gln Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 7
<211> LENGTH: 108
<212> TYPE: PRT
<213> ORGANISM: Artificial Sequence
<220> FEATURE:
<223> OTHER INFORMATION: Synthetic construct of TNFRI108-2 (K48N)

<400> SEQUENCE: 7

Asp Ser Val Cys Pro Gln Gly Asn Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
```

100 105

<210> SEQ ID NO 8
<211> LENGTH: 108
<212> TYPE: PRT
<213> ORGANISM: Artificial Sequence
<220> FEATURE:
<223> OTHER INFORMATION: Synthetic construct of TNFRI108-3 (Y49I)

<400> SEQUENCE: 8

Asp Ser Val Cys Pro Gln Gly Lys Ile Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 9
<211> LENGTH: 108
<212> TYPE: PRT
<213> ORGANISM: Artificial Sequence
<220> FEATURE:
<223> OTHER INFORMATION: Synthetic construct of TNFRI108-4 (Y49H)

<400> SEQUENCE: 9

Asp Ser Val Cys Pro Gln Gly Lys His Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 10
<211> LENGTH: 108
<212> TYPE: PRT
<213> ORGANISM: Artificial Sequence
<220> FEATURE:
<223> OTHER INFORMATION: Synthetic construct of TNFRI108-5 (P52A)

<400> SEQUENCE: 10

Asp Ser Val Cys Pro Gln Gly Lys Tyr Ile His Ala Gln Asn Asn Ser
1 5 10 15

Ile Cys Cys Thr Lys Cys His Lys Gly Thr Tyr Leu Tyr Asn Asp Cys
20 25 30

-continued

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 11
<211> LENGTH: 108
<212> TYPE: PRT
<213> ORGANISM: Artificial Sequence
<220> FEATURE:
<223> OTHER INFORMATION: Synthetic construct of TNFRI108-6 (P52S)

<400> SEQUENCE: 11

Asp Ser Val Cys Pro Gln Gly Lys Tyr Ile His Ser Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 12
<211> LENGTH: 108
<212> TYPE: PRT
<213> ORGANISM: Artificial Sequence
<220> FEATURE:
<223> OTHER INFORMATION: Synthetic construct of TNFRI108-7 (K61Q)

<400> SEQUENCE: 12

Asp Ser Val Cys Pro Gln Gly Lys Tyr Ile His Pro Gln Asn Asn Ser
1 5 10 15

Ile Cys Cys Thr Gln Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 13
<211> LENGTH: 108
<212> TYPE: PRT
<213> ORGANISM: Artificial Sequence
<220> FEATURE:
<223> OTHER INFORMATION: Synthetic construct of TNFRI108-8 (K61N)

<400> SEQUENCE: 13

```
Asp Ser Val Cys Pro Gln Gly Lys Tyr Ile His Pro Gln Asn Asn Ser
  1               5                  10                  15

Ile Cys Cys Thr Asn Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 14
<211> LENGTH: 108
<212> TYPE: PRT
<213> ORGANISM: Artificial Sequence
<220> FEATURE:
<223> OTHER INFORMATION: Synthetic construct of TNFRI108-9 (K64Q)

<400> SEQUENCE: 14

```
Asp Ser Val Cys Pro Gln Gly Lys Tyr Ile His Pro Gln Asn Asn Ser
  1               5                  10                  15

Ile Cys Cys Thr Lys Cys His Gln Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 15
<211> LENGTH: 108
<212> TYPE: PRT
<213> ORGANISM: Artificial Sequence
<220> FEATURE:
<223> OTHER INFORMATION: Synthetic construct of TNFRI108-10 (K64N)

<400> SEQUENCE: 15

```
Asp Ser Val Cys Pro Gln Gly Lys Tyr Ile His Pro Gln Asn Asn Ser
  1               5                  10                  15

Ile Cys Cys Thr Lys Cys His Asn Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45
```

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 16
<211> LENGTH: 108
<212> TYPE: PRT
<213> ORGANISM: Artificial Sequence
<220> FEATURE:
<223> OTHER INFORMATION: Synthetic construct of TNFRI108-11 (Y67I)

<400> SEQUENCE: 16

Asp Ser Val Cys Pro Gln Gly Lys Tyr Ile His Pro Gln Asn Asn Ser
1 5 10 15

Ile Cys Cys Thr Lys Cys His Lys Gly Thr Ile Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 17
<211> LENGTH: 108
<212> TYPE: PRT
<213> ORGANISM: Artificial Sequence
<220> FEATURE:
<223> OTHER INFORMATION: Synthetic construct of TNFRI108-12 (Y67H)

<400> SEQUENCE: 17

Asp Ser Val Cys Pro Gln Gly Lys Tyr Ile His Pro Gln Asn Asn Ser
1 5 10 15

Ile Cys Cys Thr Lys Cys His Lys Gly Thr His Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 18
<211> LENGTH: 108
<212> TYPE: PRT

<213> ORGANISM: Artificial Sequence
<220> FEATURE:
<223> OTHER INFORMATION: Synthetic construct of TNFRI108-13 (L68I)

<400> SEQUENCE: 18

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Ile Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 19
<211> LENGTH: 108
<212> TYPE: PRT
<213> ORGANISM: Artificial Sequence
<220> FEATURE:
<223> OTHER INFORMATION: Synthetic construct of TNFRI108-14 (L68V)

<400> SEQUENCE: 19

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 20
<211> LENGTH: 108
<212> TYPE: PRT
<213> ORGANISM: Artificial Sequence
<220> FEATURE:
<223> OTHER INFORMATION: Synthetic construct of TNFRI108-15 (Y69I)

<400> SEQUENCE: 20

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Ile Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60
```

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 21
<211> LENGTH: 108
<212> TYPE: PRT
<213> ORGANISM: Artificial Sequence
<220> FEATURE:
<223> OTHER INFORMATION: Synthetic construct of TNFRI108-16 (Y69H)

<400> SEQUENCE: 21

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu His Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 22
<211> LENGTH: 108
<212> TYPE: PRT
<213> ORGANISM: Artificial Sequence
<220> FEATURE:
<223> OTHER INFORMATION: Synthetic construct of TNFRI108-17 (D71N)

<400> SEQUENCE: 22

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asn Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 23
<211> LENGTH: 108
<212> TYPE: PRT
<213> ORGANISM: Artificial Sequence
<220> FEATURE:
<223> OTHER INFORMATION: Synthetic construct of TNFRI108-18 (D71Q)

<400> SEQUENCE: 23

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Gln Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 24
<211> LENGTH: 108
<212> TYPE: PRT
<213> ORGANISM: Artificial Sequence
<220> FEATURE:
<223> OTHER INFORMATION: Synthetic construct of TNFRI108-19 (D78N)

<400> SEQUENCE: 24

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asn Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 25
<211> LENGTH: 108
<212> TYPE: PRT
<213> ORGANISM: Artificial Sequence
<220> FEATURE:
<223> OTHER INFORMATION: Synthetic construct of TNFRI108-20 (D78Q)

<400> SEQUENCE: 25

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Gln Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

```
Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 26
<211> LENGTH: 108
<212> TYPE: PRT
<213> ORGANISM: Artificial Sequence
<220> FEATURE:
<223> OTHER INFORMATION: Synthetic construct of TNFRI108-21 (D80N)

<400> SEQUENCE: 26

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asn Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 27
<211> LENGTH: 108
<212> TYPE: PRT
<213> ORGANISM: Artificial Sequence
<220> FEATURE:
<223> OTHER INFORMATION: Synthetic construct of TNFRI108-22 (D80Q)

<400> SEQUENCE: 27

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Gln Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 28
<211> LENGTH: 108
<212> TYPE: PRT
<213> ORGANISM: Artificial Sequence
<220> FEATURE:
<223> OTHER INFORMATION: Synthetic construct of TNFRI108-23 (R82H)

<400> SEQUENCE: 28
```

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys His Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 29
<211> LENGTH: 108
<212> TYPE: PRT
<213> ORGANISM: Artificial Sequence
<220> FEATURE:
<223> OTHER INFORMATION: Synthetic construct of TNFRI108-24 (R82Q)

<400> SEQUENCE: 29

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Gln Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 30
<211> LENGTH: 108
<212> TYPE: PRT
<213> ORGANISM: Artificial Sequence
<220> FEATURE:
<223> OTHER INFORMATION: Synthetic construct of TNFRI108-25 (E83Q)

<400> SEQUENCE: 30

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Gln Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95
```

```
Ser Glu Asn Leu Phe Gln Cys Phe Asn Cys Ser Leu
            100                 105


<210> SEQ ID NO 31
<211> LENGTH: 108
<212> TYPE: PRT
<213> ORGANISM: Artificial Sequence
<220> FEATURE:
<223> OTHER INFORMATION: Synthetic construct of TNFRI108-26 (E83N)

<400> SEQUENCE: 31

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Asn Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 32
<211> LENGTH: 108
<212> TYPE: PRT
<213> ORGANISM: Artificial Sequence
<220> FEATURE:
<223> OTHER INFORMATION: Synthetic construct of TNFRI108-27 (E85Q)

<400> SEQUENCE: 32

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Gln Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 33
<211> LENGTH: 108
<212> TYPE: PRT
<213> ORGANISM: Artificial Sequence
<220> FEATURE:
<223> OTHER INFORMATION: Synthetic construct of TNFRI108-28 (E85N)

<400> SEQUENCE: 33

Asp Ser Val Cys Pro Gln Gly Lys Tyr Ile His Pro Gln Asn Asn Ser
  1               5                  10                  15
```

-continued

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Asn Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105
```

<210> SEQ ID NO 34
<211> LENGTH: 108
<212> TYPE: PRT
<213> ORGANISM: Artificial Sequence
<220> FEATURE:
<223> OTHER INFORMATION: Synthetic construct of TNFRI108-29 (F89I)

<400> SEQUENCE: 34

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Ile Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105
```

<210> SEQ ID NO 35
<211> LENGTH: 108
<212> TYPE: PRT
<213> ORGANISM: Artificial Sequence
<220> FEATURE:
<223> OTHER INFORMATION: Synthetic construct of TNFRI108-30 (F89V)

<400> SEQUENCE: 35

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Val Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105
```

-continued

<210> SEQ ID NO 36
<211> LENGTH: 108
<212> TYPE: PRT
<213> ORGANISM: Artificial Sequence
<220> FEATURE:
<223> OTHER INFORMATION: Synthetic construct of TNFRI108-31 (E93Q)

<400> SEQUENCE: 36

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Gln Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 37
<211> LENGTH: 108
<212> TYPE: PRT
<213> ORGANISM: Artificial Sequence
<220> FEATURE:
<223> OTHER INFORMATION: Synthetic construct of TNFRI108-32 (E93N)

<400> SEQUENCE: 37

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Asn Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 38
<211> LENGTH: 108
<212> TYPE: PRT
<213> ORGANISM: Artificial Sequence
<220> FEATURE:
<223> OTHER INFORMATION: Synthetic construct of TNFRI108-33 (L96I)

<400> SEQUENCE: 38

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30
```

```
Pro Gly Pro Gly Gln Asp Thr Asp Cys Arg Glu Cys Glu Ser Gly Ser
        35                  40                  45

Phe Thr Ala Ser Glu Asn His Ile Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 39
<211> LENGTH: 108
<212> TYPE: PRT
<213> ORGANISM: Artificial Sequence
<220> FEATURE:
<223> OTHER INFORMATION: Synthetic construct of TNFRI108-34 (L96V)

<400> SEQUENCE: 39

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Val Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 40
<211> LENGTH: 108
<212> TYPE: PRT
<213> ORGANISM: Artificial Sequence
<220> FEATURE:
<223> OTHER INFORMATION: Synthetic construct of TNFRI108-35 (R97H)

<400> SEQUENCE: 40

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu His His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 41
```

<211> LENGTH: 107
<212> TYPE: PRT
<213> ORGANISM: Artificial Sequence
<220> FEATURE:
<223> OTHER INFORMATION: Synthetic construct of TNFRI108-36 (R97Q)

<400> SEQUENCE: 41

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Gln His Cys Leu Cys Ser Lys Cys
     50                  55                  60

Arg Lys Glu Met Gly Gln Val Glu Ile Ser Ser Cys Thr Val Asp Arg
 65                  70                  75                  80

Asp Thr Val Cys Gly Cys Arg Lys Asn Gln Tyr Arg His Tyr Trp Ser
                 85                  90                  95

Glu Asn Leu Phe Gln Cys Phe Asn Cys Ser Leu
            100                 105
```

<210> SEQ ID NO 42
<211> LENGTH: 108
<212> TYPE: PRT
<213> ORGANISM: Artificial Sequence
<220> FEATURE:
<223> OTHER INFORMATION: Synthetic construct of TNFRI108-37 (L100I)

<400> SEQUENCE: 42

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Ile Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105
```

<210> SEQ ID NO 43
<211> LENGTH: 108
<212> TYPE: PRT
<213> ORGANISM: Artificial Sequence
<220> FEATURE:
<223> OTHER INFORMATION: Synthetic construct of TNFRI108-38 (L100V)

<400> SEQUENCE: 43

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45
```

```
Phe Thr Ala Ser Glu Asn His Leu Arg His Cys Val Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 44
<211> LENGTH: 108
<212> TYPE: PRT
<213> ORGANISM: Artificial Sequence
<220> FEATURE:
<223> OTHER INFORMATION: Synthetic construct of TNFRI108-39 (K104Q)

<400> SEQUENCE: 44

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Gln
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 45
<211> LENGTH: 108
<212> TYPE: PRT
<213> ORGANISM: Artificial Sequence
<220> FEATURE:
<223> OTHER INFORMATION: Synthetic construct of TNFRI108-40 (K104N)

<400> SEQUENCE: 45

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Asn
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 46
<211> LENGTH: 108
<212> TYPE: PRT
<213> ORGANISM: Artificial Sequence
```

<220> FEATURE:
<223> OTHER INFORMATION: Synthetic construct of TNFRI108-41 (R106H)

<400> SEQUENCE: 46

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys His Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 47
<211> LENGTH: 108
<212> TYPE: PRT
<213> ORGANISM: Artificial Sequence
<220> FEATURE:
<223> OTHER INFORMATION: Synthetic construct of TNFRI108-42 (R106Q)

<400> SEQUENCE: 47

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Gln Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu
100 105

<210> SEQ ID NO 48
<211> LENGTH: 108
<212> TYPE: PRT
<213> ORGANISM: Artificial Sequence
<220> FEATURE:
<223> OTHER INFORMATION: Synthetic construct of TNFRI108-43 (K107Q)

<400> SEQUENCE: 48

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

```
Cys Arg Gln Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 49
<211> LENGTH: 108
<212> TYPE: PRT
<213> ORGANISM: Artificial Sequence
<220> FEATURE:
<223> OTHER INFORMATION: Synthetic construct of TNFRI108-44 (K107N)

<400> SEQUENCE: 49

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Asn Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 50
<211> LENGTH: 108
<212> TYPE: PRT
<213> ORGANISM: Artificial Sequence
<220> FEATURE:
<223> OTHER INFORMATION: Synthetic construct of TNFRI108-45 (E108Q)

<400> SEQUENCE: 50

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Gln Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 51
<211> LENGTH: 108
<212> TYPE: PRT
<213> ORGANISM: Artificial Sequence
<220> FEATURE:
<223> OTHER INFORMATION: Synthetic construct of TNFRI108-46 (E108N)
```

<400> SEQUENCE: 51

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Asn Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105
```

<210> SEQ ID NO 52
<211> LENGTH: 108
<212> TYPE: PRT
<213> ORGANISM: Artificial Sequence
<220> FEATURE:
<223> OTHER INFORMATION: Synthetic construct of TNFRI108-47 (M109I)

<400> SEQUENCE: 52

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Ile Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105
```

<210> SEQ ID NO 53
<211> LENGTH: 108
<212> TYPE: PRT
<213> ORGANISM: Artificial Sequence
<220> FEATURE:
<223> OTHER INFORMATION: Synthetic construct of TNFRI108-48 (M109V)

<400> SEQUENCE: 53

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Val Gly Gln Val Glu Ile Ser Ser Cys Thr Val Asp
65                  70                  75                  80
```

```
Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 54
<211> LENGTH: 108
<212> TYPE: PRT
<213> ORGANISM: Artificial Sequence
<220> FEATURE:
<223> OTHER INFORMATION: Synthetic construct of TNFRI108-49 (E113Q)

<400> SEQUENCE: 54

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Gln Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 55
<211> LENGTH: 108
<212> TYPE: PRT
<213> ORGANISM: Artificial Sequence
<220> FEATURE:
<223> OTHER INFORMATION: Synthetic construct of TNFRI108-50 (E113N)

<400> SEQUENCE: 55

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Asn Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 56
<211> LENGTH: 108
<212> TYPE: PRT
<213> ORGANISM: Artificial Sequence
<220> FEATURE:
<223> OTHER INFORMATION: Synthetic construct of TNFRI108-51 (D120N)

<400> SEQUENCE: 56

Asp Ser Val Cys Pro Gln Gly Lys Tyr Ile His Pro Gln Asn Asn Ser
```

-continued

```
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asn
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
             100                 105


<210> SEQ ID NO 57
<211> LENGTH: 108
<212> TYPE: PRT
<213> ORGANISM: Artificial Sequence
<220> FEATURE:
<223> OTHER INFORMATION: Synthetic construct of TNFRI108-52 (D120Q)

<400> SEQUENCE: 57

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Gln
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
             100                 105


<210> SEQ ID NO 58
<211> LENGTH: 108
<212> TYPE: PRT
<213> ORGANISM: Artificial Sequence
<220> FEATURE:
<223> OTHER INFORMATION: Synthetic construct of TNFRI108-53 (R121H)

<400> SEQUENCE: 58

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

His Asp Thr Val Cys Gly Cys Arg Lys Asn Gln Tyr Arg His Tyr Trp
                 85                  90                  95
```

```
Ser Glu Asn Leu Phe Gln Cys Phe Asn Cys Ser Leu
            100                 105


<210> SEQ ID NO 59
<211> LENGTH: 108
<212> TYPE: PRT
<213> ORGANISM: Artificial Sequence
<220> FEATURE:
<223> OTHER INFORMATION: Synthetic construct of TNFRI108-54 (R121Q)

<400> SEQUENCE: 59

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Gln Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 60
<211> LENGTH: 108
<212> TYPE: PRT
<213> ORGANISM: Artificial Sequence
<220> FEATURE:
<223> OTHER INFORMATION: Synthetic construct of TNFRI108-55 (D122N)

<400> SEQUENCE: 60

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asn Thr Val Cys Gly Cys Arg Lys Asn Gln Tyr Arg His Tyr Trp
                 85                  90                  95

Ser Glu Asn Leu Phe Gln Cys Phe Asn Cys Ser Leu
            100                 105


<210> SEQ ID NO 61
<211> LENGTH: 108
<212> TYPE: PRT
<213> ORGANISM: Artificial Sequence
<220> FEATURE:
<223> OTHER INFORMATION: Synthetic construct of TNFRI108-56 (D122Q)

<400> SEQUENCE: 61

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
```

```
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Gln Thr Val Cys Gly Cys Arg Lys Asn Gln Tyr Arg His Tyr Trp
                85                  90                  95

Ser Glu Asn Leu Phe Gln Cys Phe Asn Cys Ser Leu
            100                 105


<210> SEQ ID NO 62
<211> LENGTH: 108
<212> TYPE: PRT
<213> ORGANISM: Artificial Sequence
<220> FEATURE:
<223> OTHER INFORMATION: Synthetic construct of TNFRI108-57 (R128H)

<400> SEQUENCE: 62

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys His Lys Asn Gln Tyr Arg His Tyr Trp
                85                  90                  95

Ser Glu Asn Leu Phe Gln Cys Phe Asn Cys Ser Leu
            100                 105


<210> SEQ ID NO 63
<211> LENGTH: 108
<212> TYPE: PRT
<213> ORGANISM: Artificial Sequence
<220> FEATURE:
<223> OTHER INFORMATION: Synthetic construct of TNFRI108-58 (R128Q)

<400> SEQUENCE: 63

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Gln Lys Asn Gln Tyr Arg His Tyr Trp
                85                  90                  95

Ser Glu Asn Leu Phe Gln Cys Phe Asn Cys Ser Leu
            100                 105
```

<210> SEQ ID NO 64
<211> LENGTH: 108
<212> TYPE: PRT
<213> ORGANISM: Artificial Sequence
<220> FEATURE:
<223> OTHER INFORMATION: Synthetic construct of TNFRI108-59 (K129Q)

<400> SEQUENCE: 64

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Gln Asn Gln Tyr Arg His Tyr Trp
                 85                  90                  95

Ser Glu Asn Leu Phe Gln Cys Phe Asn Cys Ser Leu
            100                 105
```

<210> SEQ ID NO 65
<211> LENGTH: 108
<212> TYPE: PRT
<213> ORGANISM: Artificial Sequence
<220> FEATURE:
<223> OTHER INFORMATION: Synthetic construct of TNFRI108-60 (K129N)

<400> SEQUENCE: 65

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Asn Asn Gln Tyr Arg His Tyr Trp
                 85                  90                  95

Ser Glu Asn Leu Phe Gln Cys Phe Asn Cys Ser Leu
            100                 105
```

<210> SEQ ID NO 66
<211> LENGTH: 108
<212> TYPE: PRT
<213> ORGANISM: Artificial Sequence
<220> FEATURE:
<223> OTHER INFORMATION: Synthetic construct of TNFRI108-61 (Y132I)

<400> SEQUENCE: 66

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
```

```
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Ile Arg His Tyr Trp
                 85                  90                  95

Ser Glu Asn Leu Phe Gln Cys Phe Asn Cys Ser Leu
            100                 105


<210> SEQ ID NO 67
<211> LENGTH: 108
<212> TYPE: PRT
<213> ORGANISM: Artificial Sequence
<220> FEATURE:
<223> OTHER INFORMATION: Synthetic construct of TNFRI108-62 (Y132H)

<400> SEQUENCE: 67

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln His Arg His Tyr Trp
                 85                  90                  95

Ser Glu Asn Leu Phe Gln Cys Phe Asn Cys Ser Leu
            100                 105


<210> SEQ ID NO 68
<211> LENGTH: 108
<212> TYPE: PRT
<213> ORGANISM: Artificial Sequence
<220> FEATURE:
<223> OTHER INFORMATION: Synthetic construct of TNFRI108-63 (R133H)

<400> SEQUENCE: 68

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr His His Tyr Trp
                 85                  90                  95

Ser Glu Asn Leu Phe Gln Cys Phe Asn Cys Ser Leu
            100                 105


<210> SEQ ID NO 69
<211> LENGTH: 108
```

<212> TYPE: PRT
<213> ORGANISM: Artificial Sequence
<220> FEATURE:
<223> OTHER INFORMATION: Synthetic construct of TNFRI108-64 (R133Q)

<400> SEQUENCE: 69

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Gln His Tyr Trp
                 85                  90                  95

Ser Glu Asn Leu Phe Gln Cys Phe Asn Cys Ser Leu
            100                 105
```

<210> SEQ ID NO 70
<211> LENGTH: 108
<212> TYPE: PRT
<213> ORGANISM: Artificial Sequence
<220> FEATURE:
<223> OTHER INFORMATION: Synthetic construct of TNFRI108-65 (Y135I)

<400> SEQUENCE: 70

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Ile Trp
                 85                  90                  95

Ser Glu Asn Leu Phe Gln Cys Phe Asn Cys Ser Leu
            100                 105
```

<210> SEQ ID NO 71
<211> LENGTH: 108
<212> TYPE: PRT
<213> ORGANISM: Artificial Sequence
<220> FEATURE:
<223> OTHER INFORMATION: Synthetic construct of TNFRI108-66 (Y135H)

<400> SEQUENCE: 71

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
```

```
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His His Trp
                 85                  90                  95

Ser Glu Asn Leu Phe Gln Cys Phe Asn Cys Ser Leu
            100                 105


<210> SEQ ID NO 72
<211> LENGTH: 108
<212> TYPE: PRT
<213> ORGANISM: Artificial Sequence
<220> FEATURE:
<223> OTHER INFORMATION: Synthetic construct of TNFRI108-67 (W136H)

<400> SEQUENCE: 72

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr His
                 85                  90                  95

Ser Glu Asn Leu Phe Gln Cys Phe Asn Cys Ser Leu
            100                 105


<210> SEQ ID NO 73
<211> LENGTH: 108
<212> TYPE: PRT
<213> ORGANISM: Artificial Sequence
<220> FEATURE:
<223> OTHER INFORMATION: Synthetic construct of TNFRI108-68 (W136S)

<400> SEQUENCE: 73

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Ser
                 85                  90                  95

Ser Glu Asn Leu Phe Gln Cys Phe Asn Cys Ser Leu
            100                 105


<210> SEQ ID NO 74
<211> LENGTH: 108
<212> TYPE: PRT
<213> ORGANISM: Artificial Sequence
<220> FEATURE:
```

<223> OTHER INFORMATION: Synthetic construct of TNFRI108-69 (E138Q)

<400> SEQUENCE: 74

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Gln Asn Leu Phe Gln Cys Phe Asn Cys Ser Leu
100 105

<210> SEQ ID NO 75
<211> LENGTH: 108
<212> TYPE: PRT
<213> ORGANISM: Artificial Sequence
<220> FEATURE:
<223> OTHER INFORMATION: Synthetic construct of TNFRI108-70 (E138N)

<400> SEQUENCE: 75

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Asn Asn Leu Phe Gln Cys Phe Asn Cys Ser Leu
100 105

<210> SEQ ID NO 76
<211> LENGTH: 108
<212> TYPE: PRT
<213> ORGANISM: Artificial Sequence
<220> FEATURE:
<223> OTHER INFORMATION: Synthetic construct of TNFRI108-71 (L140I)

<400> SEQUENCE: 76

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp

-continued

```
65                  70                  75                  80

Arg Asp Thr Val Cys Gly Cys Arg Lys Asn Gln Tyr Arg His Tyr Trp
                85                  90                  95

Ser Glu Asn Ile Phe Gln Cys Phe Asn Cys Ser Leu
            100                 105


<210> SEQ ID NO 77
<211> LENGTH: 108
<212> TYPE: PRT
<213> ORGANISM: Artificial Sequence
<220> FEATURE:
<223> OTHER INFORMATION: Synthetic construct of TNFRI108-72 (L140V)

<400> SEQUENCE: 77

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Val Phe Gln Cys Phe Asn Cys Ser Leu
            100                 105


<210> SEQ ID NO 78
<211> LENGTH: 108
<212> TYPE: PRT
<213> ORGANISM: Artificial Sequence
<220> FEATURE:
<223> OTHER INFORMATION: Synthetic construct of TNFRI108-73 (F141I)

<400> SEQUENCE: 78

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Ile Gln Cys Phe Asn Cys Ser Leu
            100                 105


<210> SEQ ID NO 79
<211> LENGTH: 108
<212> TYPE: PRT
<213> ORGANISM: Artificial Sequence
<220> FEATURE:
<223> OTHER INFORMATION: Synthetic construct of TNFRI108-74 (F141V)

<400> SEQUENCE: 79
```

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Val Gln Cys Phe Asn Cys Ser Leu
            100                 105
```

<210> SEQ ID NO 80
<211> LENGTH: 108
<212> TYPE: PRT
<213> ORGANISM: Artificial Sequence
<220> FEATURE:
<223> OTHER INFORMATION: Synthetic construct of TNFRI108-75 (F144I)

<400> SEQUENCE: 80

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu
            100                 105
```

<210> SEQ ID NO 81
<211> LENGTH: 108
<212> TYPE: PRT
<213> ORGANISM: Artificial Sequence
<220> FEATURE:
<223> OTHER INFORMATION: Synthetic construct of TNFRI108-76 (F144V)

<400> SEQUENCE: 81

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
```

```
                85                  90                  95

Ser Glu Asn Leu Phe Gln Cys Val Asn Cys Ser Leu
            100                 105


<210> SEQ ID NO 82
<211> LENGTH: 126
<212> TYPE: PRT
<213> ORGANISM: Artificial Sequence
<220> FEATURE:
<223> OTHER INFORMATION: Synthetic construct of TNFRI126-1 (K48Q)

<400> SEQUENCE: 82

Asp Ser Val Cys Pro Gln Gly Gln Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 83
<211> LENGTH: 126
<212> TYPE: PRT
<213> ORGANISM: Artificial Sequence
<220> FEATURE:
<223> OTHER INFORMATION: Synthetic construct of TNFRI126-2 (K48N)

<400> SEQUENCE: 83

Asp Ser Val Cys Pro Gln Gly Asn Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 84
<211> LENGTH: 126
<212> TYPE: PRT
<213> ORGANISM: Artificial Sequence
<220> FEATURE:
```

<223> OTHER INFORMATION: Synthetic construct of TNFRI126-3 (Y49I)

<400> SEQUENCE: 84

Asp Ser Val Cys Pro Gln Gly Lys Ile Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 85
<211> LENGTH: 126
<212> TYPE: PRT
<213> ORGANISM: Artificial Sequence
<220> FEATURE:
<223> OTHER INFORMATION: Synthetic construct of TNFRI126-4 (Y49H)

<400> SEQUENCE: 85

Asp Ser Val Cys Pro Gln Gly Lys His Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 86
<211> LENGTH: 126
<212> TYPE: PRT
<213> ORGANISM: Artificial Sequence
<220> FEATURE:
<223> OTHER INFORMATION: Synthetic construct of TNFRI126-5 (P52A)

<400> SEQUENCE: 86

Asp Ser Val Cys Pro Gln Gly Lys Tyr Ile His Ala Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser

-continued

```
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 87
<211> LENGTH: 126
<212> TYPE: PRT
<213> ORGANISM: Artificial Sequence
<220> FEATURE:
<223> OTHER INFORMATION: Synthetic construct of TNFRI126-6 (P52S)

<400> SEQUENCE: 87

Asp Ser Val Cys Pro Gln Gly Lys Tyr Ile His Ser Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 88
<211> LENGTH: 126
<212> TYPE: PRT
<213> ORGANISM: Artificial Sequence
<220> FEATURE:
<223> OTHER INFORMATION: Synthetic construct of TNFRI126-7 (K61Q)

<400> SEQUENCE: 88

Asp Ser Val Cys Pro Gln Gly Lys Tyr Ile His Pro Gln Asn Asn Ser
  1               5                  10                  15

Ile Cys Cys Thr Gln Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95
```

-continued

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 89
<211> LENGTH: 126
<212> TYPE: PRT
<213> ORGANISM: Artificial Sequence
<220> FEATURE:
<223> OTHER INFORMATION: Synthetic construct of TNFRI126-8 (K61N)

<400> SEQUENCE: 89

Asp Ser Val Cys Pro Gln Gly Lys Tyr Ile His Pro Gln Asn Asn Ser
  1               5                  10                  15

Ile Cys Cys Thr Asn Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 90
<211> LENGTH: 126
<212> TYPE: PRT
<213> ORGANISM: Artificial Sequence
<220> FEATURE:
<223> OTHER INFORMATION: Synthetic construct of TNFRI126-9 (K64Q)

<400> SEQUENCE: 90

Asp Ser Val Cys Pro Gln Gly Lys Tyr Ile His Pro Gln Asn Asn Ser
  1               5                  10                  15

Ile Cys Cys Thr Lys Cys His Gln Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 91
<211> LENGTH: 126
<212> TYPE: PRT
<213> ORGANISM: Artificial Sequence
```

```
<220> FEATURE:
<223> OTHER INFORMATION: Synthetic construct of TNFRI126-10 (K64N)

<400> SEQUENCE: 91

Asp Ser Val Cys Pro Gln Gly Lys Tyr Ile His Pro Gln Asn Asn Ser
  1               5                  10                  15

Ile Cys Cys Thr Lys Cys His Asn Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 92
<211> LENGTH: 126
<212> TYPE: PRT
<213> ORGANISM: Artificial Sequence
<220> FEATURE:
<223> OTHER INFORMATION: Synthetic construct of TNFRI126-11 (Y67I)

<400> SEQUENCE: 92

Asp Ser Val Cys Pro Gln Gly Lys Tyr Ile His Pro Gln Asn Asn Ser
  1               5                  10                  15

Ile Cys Cys Thr Lys Cys His Lys Gly Thr Ile Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 93
<211> LENGTH: 126
<212> TYPE: PRT
<213> ORGANISM: Artificial Sequence
<220> FEATURE:
<223> OTHER INFORMATION: Synthetic construct of TNFRI126-12 (Y67H)

<400> SEQUENCE: 93

Asp Ser Val Cys Pro Gln Gly Lys Tyr Ile His Pro Gln Asn Asn Ser
  1               5                  10                  15

Ile Cys Cys Thr Lys Cys His Lys Gly Thr His Leu Tyr Asn Asp Cys
             20                  25                  30
```

```
Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 94
<211> LENGTH: 126
<212> TYPE: PRT
<213> ORGANISM: Artificial Sequence
<220> FEATURE:
<223> OTHER INFORMATION: Synthetic construct of TNFRI126-13 (L68I)

<400> SEQUENCE: 94

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Ile Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 95
<211> LENGTH: 126
<212> TYPE: PRT
<213> ORGANISM: Artificial Sequence
<220> FEATURE:
<223> OTHER INFORMATION: Synthetic construct of TNFRI126-14 (L68V)

<400> SEQUENCE: 95

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95
```

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 96
<211> LENGTH: 126
<212> TYPE: PRT
<213> ORGANISM: Artificial Sequence
<220> FEATURE:
<223> OTHER INFORMATION: Synthetic construct of TNFRI126-15 (Y69I)

<400> SEQUENCE: 96

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Ile Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 97
<211> LENGTH: 126
<212> TYPE: PRT
<213> ORGANISM: Artificial Sequence
<220> FEATURE:
<223> OTHER INFORMATION: Synthetic construct of TNFRI126-16 (Y69H)

<400> SEQUENCE: 97

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu His Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 98
<211> LENGTH: 126
<212> TYPE: PRT
```

<213> ORGANISM: Artificial Sequence
<220> FEATURE:
<223> OTHER INFORMATION: Synthetic construct of TNFRI126-17 (D71N)

<400> SEQUENCE: 98

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asn Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 99
<211> LENGTH: 126
<212> TYPE: PRT
<213> ORGANISM: Artificial Sequence
<220> FEATURE:
<223> OTHER INFORMATION: Synthetic construct of TNFRI126-18 (D71Q)

<400> SEQUENCE: 99

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Gln Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 100
<211> LENGTH: 126
<212> TYPE: PRT
<213> ORGANISM: Artificial Sequence
<220> FEATURE:
<223> OTHER INFORMATION: Synthetic construct of TNFRI126-19 (D78N)

<400> SEQUENCE: 100

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30
```

```
Pro Gly Pro Gly Gln Asn Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 101
<211> LENGTH: 126
<212> TYPE: PRT
<213> ORGANISM: Artificial Sequence
<220> FEATURE:
<223> OTHER INFORMATION: Synthetic construct of TNFRI126-20 (D78Q)

<400> SEQUENCE: 101

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Gln Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 102
<211> LENGTH: 126
<212> TYPE: PRT
<213> ORGANISM: Artificial Sequence
<220> FEATURE:
<223> OTHER INFORMATION: Synthetic construct of TNFRI126-21 (D80N)

<400> SEQUENCE: 102

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asn Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
```

```
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 103
<211> LENGTH: 126
<212> TYPE: PRT
<213> ORGANISM: Artificial Sequence
<220> FEATURE:
<223> OTHER INFORMATION: Synthetic construct of TNFRI126-22 (D80Q)

<400> SEQUENCE: 103

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Gln Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 104
<211> LENGTH: 126
<212> TYPE: PRT
<213> ORGANISM: Artificial Sequence
<220> FEATURE:
<223> OTHER INFORMATION: Synthetic construct of TNFRI126-23 (R82H)

<400> SEQUENCE: 104

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys His Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 105
<211> LENGTH: 126
```

<212> TYPE: PRT
<213> ORGANISM: Artificial Sequence
<220> FEATURE:
<223> OTHER INFORMATION: Synthetic construct of TNFRI126-24 (R82Q)

<400> SEQUENCE: 105

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Gln Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 106
<211> LENGTH: 126
<212> TYPE: PRT
<213> ORGANISM: Artificial Sequence
<220> FEATURE:
<223> OTHER INFORMATION: Synthetic construct of TNFRI126-25 (E83Q)

<400> SEQUENCE: 106

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Gln Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 107
<211> LENGTH: 126
<212> TYPE: PRT
<213> ORGANISM: Artificial Sequence
<220> FEATURE:
<223> OTHER INFORMATION: Synthetic construct of TNFRI126-26 (E83N)

<400> SEQUENCE: 107

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
```

20 25 30

Pro Gly Pro Gly Gln Asp Thr Asp Cys Arg Asn Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 108
<211> LENGTH: 126
<212> TYPE: PRT
<213> ORGANISM: Artificial Sequence
<220> FEATURE:
<223> OTHER INFORMATION: Synthetic construct of TNFRI126-27 (E85Q)

<400> SEQUENCE: 108

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Gln Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 109
<211> LENGTH: 126
<212> TYPE: PRT
<213> ORGANISM: Artificial Sequence
<220> FEATURE:
<223> OTHER INFORMATION: Synthetic construct of TNFRI126-28 (E85N)

<400> SEQUENCE: 109

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Asn Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

```
Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 110
<211> LENGTH: 126
<212> TYPE: PRT
<213> ORGANISM: Artificial Sequence
<220> FEATURE:
<223> OTHER INFORMATION: Synthetic construct of TNFRI126-29 (F89I)

<400> SEQUENCE: 110

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Ile Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 111
<211> LENGTH: 126
<212> TYPE: PRT
<213> ORGANISM: Artificial Sequence
<220> FEATURE:
<223> OTHER INFORMATION: Synthetic construct of TNFRI126-30 (F89V)

<400> SEQUENCE: 111

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Val Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 112
```

<211> LENGTH: 126
<212> TYPE: PRT
<213> ORGANISM: Artificial Sequence
<220> FEATURE:
<223> OTHER INFORMATION: Synthetic construct of TNFRI126-31 (E93Q)

<400> SEQUENCE: 112

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Gln Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 113
<211> LENGTH: 126
<212> TYPE: PRT
<213> ORGANISM: Artificial Sequence
<220> FEATURE:
<223> OTHER INFORMATION: Synthetic construct of TNFRI126-32 (E93N)

<400> SEQUENCE: 113

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Asn Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 114
<211> LENGTH: 126
<212> TYPE: PRT
<213> ORGANISM: Artificial Sequence
<220> FEATURE:
<223> OTHER INFORMATION: Synthetic construct of TNFRI126-33 (L96I)

<400> SEQUENCE: 114

Asp Ser Val Cys Pro Gln Gly Lys Tyr Ile His Pro Gln Asn Asn Ser
1 5 10 15

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Ile Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 115
<211> LENGTH: 126
<212> TYPE: PRT
<213> ORGANISM: Artificial Sequence
<220> FEATURE:
<223> OTHER INFORMATION: Synthetic construct of TNFRI126-34 (L96V)

<400> SEQUENCE: 115

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Val Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 116
<211> LENGTH: 126
<212> TYPE: PRT
<213> ORGANISM: Artificial Sequence
<220> FEATURE:
<223> OTHER INFORMATION: Synthetic construct of TNFRI126-35 (R97H)

<400> SEQUENCE: 116

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu His His Cys Leu Ser Cys Ser Lys
    50                  55                  60

Cys Arg Lys Glu Met Gly Gln Val Glu Ile Ser Ser Cys Thr Val Asp
65                  70                  75                  80
```

```
Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 117
<211> LENGTH: 125
<212> TYPE: PRT
<213> ORGANISM: Artificial Sequence
<220> FEATURE:
<223> OTHER INFORMATION: Synthetic construct of TNFRI126-36 (R97Q)

<400> SEQUENCE: 117

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Gln His Cys Leu Cys Ser Lys Cys
     50                  55                  60

Arg Lys Glu Met Gly Gln Val Glu Ile Ser Ser Cys Thr Val Asp Arg
 65                  70                  75                  80

Asp Thr Val Cys Gly Cys Arg Lys Asn Gln Tyr Arg His Tyr Trp Ser
                 85                  90                  95

Glu Asn Leu Phe Gln Cys Phe Asn Cys Ser Leu Cys Leu Asn Gly Thr
            100                 105                 110

Val His Leu Ser Cys Gln Glu Lys Gln Asn Thr Val Cys
        115                 120                 125


<210> SEQ ID NO 118
<211> LENGTH: 126
<212> TYPE: PRT
<213> ORGANISM: Artificial Sequence
<220> FEATURE:
<223> OTHER INFORMATION: Synthetic construct of TNFRI126-37 (L100I)

<400> SEQUENCE: 118

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Ile Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 119
<211> LENGTH: 126
<212> TYPE: PRT
<213> ORGANISM: Artificial Sequence
<220> FEATURE:
<223> OTHER INFORMATION: Synthetic construct of TNFRI126-38 (L100V)

<400> SEQUENCE: 119

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Val Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 120
<211> LENGTH: 126
<212> TYPE: PRT
<213> ORGANISM: Artificial Sequence
<220> FEATURE:
<223> OTHER INFORMATION: Synthetic construct of TNFRI126-39 (K104Q)

<400> SEQUENCE: 120

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Gln
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 121
<211> LENGTH: 126
<212> TYPE: PRT
<213> ORGANISM: Artificial Sequence
<220> FEATURE:
<223> OTHER INFORMATION: Synthetic construct of TNFRI126-40 (K104N)

<400> SEQUENCE: 121

```
Asp Ser Val Cys Pro Gln Gly Lys Tyr Ile His Pro Gln Asn Asn Ser
  1               5                  10                  15
```

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Asn
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 122
<211> LENGTH: 126
<212> TYPE: PRT
<213> ORGANISM: Artificial Sequence
<220> FEATURE:
<223> OTHER INFORMATION: Synthetic construct of TNFRI126-41 (R106H)

<400> SEQUENCE: 122

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys His Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 123
<211> LENGTH: 126
<212> TYPE: PRT
<213> ORGANISM: Artificial Sequence
<220> FEATURE:
<223> OTHER INFORMATION: Synthetic construct of TNFRI126-42 (R106Q)

<400> SEQUENCE: 123

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Gln Lys Glu Met Gly Gln Val Glu Ile Ser Ser Cys Thr Val Asp
```

```
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 124
<211> LENGTH: 126
<212> TYPE: PRT
<213> ORGANISM: Artificial Sequence
<220> FEATURE:
<223> OTHER INFORMATION: Synthetic construct of TNFRI126-43 (K107Q)

<400> SEQUENCE: 124

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Gln Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 125
<211> LENGTH: 126
<212> TYPE: PRT
<213> ORGANISM: Artificial Sequence
<220> FEATURE:
<223> OTHER INFORMATION: Synthetic construct of TNFRI126-44 (K107N)

<400> SEQUENCE: 125

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Asn Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

```
<210> SEQ ID NO 126
<211> LENGTH: 126
<212> TYPE: PRT
<213> ORGANISM: Artificial Sequence
<220> FEATURE:
<223> OTHER INFORMATION: Synthetic construct of TNFRI126-45 (E108Q)

<400> SEQUENCE: 126

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Gln Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 127
<211> LENGTH: 126
<212> TYPE: PRT
<213> ORGANISM: Artificial Sequence
<220> FEATURE:
<223> OTHER INFORMATION: Synthetic construct of TNFRI126-46 (E108N)

<400> SEQUENCE: 127

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Asn Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 128
<211> LENGTH: 126
<212> TYPE: PRT
<213> ORGANISM: Artificial Sequence
<220> FEATURE:
<223> OTHER INFORMATION: Synthetic construct of TNFRI126-47 (M109I)

<400> SEQUENCE: 128

Asp Ser Val Cys Pro Gln Gly Lys Tyr Ile His Pro Gln Asn Asn Ser
```

```
  1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Ile Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 129
<211> LENGTH: 126
<212> TYPE: PRT
<213> ORGANISM: Artificial Sequence
<220> FEATURE:
<223> OTHER INFORMATION: Synthetic construct of TNFRI126-48 (M109V)

<400> SEQUENCE: 129

Asp Ser Val Cys Pro Gln Gly Lys Tyr Ile His Pro Gln Asn Asn Ser
  1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Val Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 130
<211> LENGTH: 126
<212> TYPE: PRT
<213> ORGANISM: Artificial Sequence
<220> FEATURE:
<223> OTHER INFORMATION: Synthetic construct of TNFRI126-49 (E113Q)

<400> SEQUENCE: 130

Asp Ser Val Cys Pro Gln Gly Lys Tyr Ile His Pro Gln Asn Asn Ser
  1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60
```

```
Cys Arg Lys Glu Met Gly Gln Val Gln Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 131
<211> LENGTH: 126
<212> TYPE: PRT
<213> ORGANISM: Artificial Sequence
<220> FEATURE:
<223> OTHER INFORMATION: Synthetic construct of TNFRI126-50 (E113N)

<400> SEQUENCE: 131

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Asn Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 132
<211> LENGTH: 126
<212> TYPE: PRT
<213> ORGANISM: Artificial Sequence
<220> FEATURE:
<223> OTHER INFORMATION: Synthetic construct of TNFRI126-51 (D120N)

<400> SEQUENCE: 132

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asn
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 133
<211> LENGTH: 126
<212> TYPE: PRT
<213> ORGANISM: Artificial Sequence
<220> FEATURE:
<223> OTHER INFORMATION: Synthetic construct of TNFRI126-52 (D120Q)

<400> SEQUENCE: 133

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Gln
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 134
<211> LENGTH: 126
<212> TYPE: PRT
<213> ORGANISM: Artificial Sequence
<220> FEATURE:
<223> OTHER INFORMATION: Synthetic construct of TNFRI126-53 (R121H)

<400> SEQUENCE: 134

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

His Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 135
<211> LENGTH: 126
<212> TYPE: PRT
<213> ORGANISM: Artificial Sequence
<220> FEATURE:
<223> OTHER INFORMATION: Synthetic construct of TNFRI126-54 (R121Q)

<400> SEQUENCE: 135

-continued

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Gln Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 136
<211> LENGTH: 126
<212> TYPE: PRT
<213> ORGANISM: Artificial Sequence
<220> FEATURE:
<223> OTHER INFORMATION: Synthetic construct of TNFRI126-55 (D122N)

<400> SEQUENCE: 136

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asn Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 137
<211> LENGTH: 126
<212> TYPE: PRT
<213> ORGANISM: Artificial Sequence
<220> FEATURE:
<223> OTHER INFORMATION: Synthetic construct of TNFRI126-56 (D122Q)

<400> SEQUENCE: 137

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60
```

```
Cys Arg Lys Glu Met Gly Gln Val Glu Ile Ser Ser Cys Thr Val Asp
 65                  70                  75                  80

Arg Gln Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 138
<211> LENGTH: 126
<212> TYPE: PRT
<213> ORGANISM: Artificial Sequence
<220> FEATURE:
<223> OTHER INFORMATION: Synthetic construct of TNFRI126-57 (R128H)

<400> SEQUENCE: 138

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys His Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 139
<211> LENGTH: 126
<212> TYPE: PRT
<213> ORGANISM: Artificial Sequence
<220> FEATURE:
<223> OTHER INFORMATION: Synthetic construct of TNFRI126-58 (R128Q)

<400> SEQUENCE: 139

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Gln Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
```

115 120 125

<210> SEQ ID NO 140
<211> LENGTH: 126
<212> TYPE: PRT
<213> ORGANISM: Artificial Sequence
<220> FEATURE:
<223> OTHER INFORMATION: Synthetic construct of TNFRI126-59 (K129Q)

<400> SEQUENCE: 140

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Gln Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 141
<211> LENGTH: 126
<212> TYPE: PRT
<213> ORGANISM: Artificial Sequence
<220> FEATURE:
<223> OTHER INFORMATION: Synthetic construct of TNFRI126-60 (K129N)

<400> SEQUENCE: 141

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Asn Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 142
<211> LENGTH: 126
<212> TYPE: PRT
<213> ORGANISM: Artificial Sequence
<220> FEATURE:
<223> OTHER INFORMATION: Synthetic construct of TNFRI126-61 (Y132I)

<400> SEQUENCE: 142

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Ile Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 143
<211> LENGTH: 126
<212> TYPE: PRT
<213> ORGANISM: Artificial Sequence
<220> FEATURE:
<223> OTHER INFORMATION: Synthetic construct of TNFRI126-62 (Y132H)

<400> SEQUENCE: 143

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln His Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 144
<211> LENGTH: 126
<212> TYPE: PRT
<213> ORGANISM: Artificial Sequence
<220> FEATURE:
<223> OTHER INFORMATION: Synthetic construct of TNFRI126-63 (R133H)

<400> SEQUENCE: 144

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
```

```
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr His His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 145
<211> LENGTH: 126
<212> TYPE: PRT
<213> ORGANISM: Artificial Sequence
<220> FEATURE:
<223> OTHER INFORMATION: Synthetic construct of TNFRI126-64 (R133Q)

<400> SEQUENCE: 145

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Gln His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 146
<211> LENGTH: 126
<212> TYPE: PRT
<213> ORGANISM: Artificial Sequence
<220> FEATURE:
<223> OTHER INFORMATION: Synthetic construct of TNFRI126-65 (Y135I)

<400> SEQUENCE: 146

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Ile Trp
                 85                  90                  95

Ser Glu Asn Leu Phe Gln Cys Phe Asn Cys Ser Leu Cys Leu Asn Gly
            100                 105                 110
```

Thr Val His Leu Ser Cys Gln Glu Lys Gln Asn Thr Val Cys
115 120 125

<210> SEQ ID NO 147
<211> LENGTH: 126
<212> TYPE: PRT
<213> ORGANISM: Artificial Sequence
<220> FEATURE:
<223> OTHER INFORMATION: Synthetic construct of TNFRI126-66 (Y135H)

<400> SEQUENCE: 147

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His His Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 148
<211> LENGTH: 126
<212> TYPE: PRT
<213> ORGANISM: Artificial Sequence
<220> FEATURE:
<223> OTHER INFORMATION: Synthetic construct of TNFRI126-67 (W136H)

<400> SEQUENCE: 148

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr His
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 149
<211> LENGTH: 126
<212> TYPE: PRT
<213> ORGANISM: Artificial Sequence
<220> FEATURE:
<223> OTHER INFORMATION: Synthetic construct of TNFRI126-68 (W136S)

<400> SEQUENCE: 149

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Ser
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 150
<211> LENGTH: 126
<212> TYPE: PRT
<213> ORGANISM: Artificial Sequence
<220> FEATURE:
<223> OTHER INFORMATION: Synthetic construct of TNFRI126-69 (E138Q)

<400> SEQUENCE: 150

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Gln Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 151
<211> LENGTH: 126
<212> TYPE: PRT
<213> ORGANISM: Artificial Sequence
<220> FEATURE:
<223> OTHER INFORMATION: Synthetic construct of TNFRI126-70 (E138N)

<400> SEQUENCE: 151

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Asn Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 152
<211> LENGTH: 126
<212> TYPE: PRT
<213> ORGANISM: Artificial Sequence
<220> FEATURE:
<223> OTHER INFORMATION: Synthetic construct of TNFRI126-71 (L140I)

<400> SEQUENCE: 152

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Ile Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 153
<211> LENGTH: 126
<212> TYPE: PRT
<213> ORGANISM: Artificial Sequence
<220> FEATURE:
<223> OTHER INFORMATION: Synthetic construct of TNFRI126-72 (L140V)

<400> SEQUENCE: 153

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Val Phe Gln Cys Phe Asn Cys Ser Leu Cys Leu Asn Gly
            100                 105                 110
```

Thr Val His Leu Ser Cys Gln Glu Lys Gln Asn Thr Val Cys
        115                 120                 125

<210> SEQ ID NO 154
<211> LENGTH: 126
<212> TYPE: PRT
<213> ORGANISM: Artificial Sequence
<220> FEATURE:
<223> OTHER INFORMATION: Synthetic construct of TNFRI126-73 (F141I)

<400> SEQUENCE: 154

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Ile Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 155
<211> LENGTH: 126
<212> TYPE: PRT
<213> ORGANISM: Artificial Sequence
<220> FEATURE:
<223> OTHER INFORMATION: Synthetic construct of TNFRI126-74 (F141V)

<400> SEQUENCE: 155

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Val Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 156
<211> LENGTH: 126
<212> TYPE: PRT
<213> ORGANISM: Artificial Sequence
<220> FEATURE:
<223> OTHER INFORMATION: Synthetic construct of TNFRI126-75 (F144I)

-continued

<400> SEQUENCE: 156

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Ile Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 157
<211> LENGTH: 126
<212> TYPE: PRT
<213> ORGANISM: Artificial Sequence
<220> FEATURE:
<223> OTHER INFORMATION: Synthetic construct of TNFRI126-76 (F144V)

<400> SEQUENCE: 157

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 158
<211> LENGTH: 126
<212> TYPE: PRT
<213> ORGANISM: Artificial Sequence
<220> FEATURE:
<223> OTHER INFORMATION: Synthetic construct of TNFRI126-77 (L150I)

<400> SEQUENCE: 158

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Ile Asn Gly
            100                 105                 110

Thr Val His Leu Ser Cys Gln Glu Lys Gln Asn Thr Val Cys
        115                 120                 125
```

<210> SEQ ID NO 159
<211> LENGTH: 126
<212> TYPE: PRT
<213> ORGANISM: Artificial Sequence
<220> FEATURE:
<223> OTHER INFORMATION: Synthetic construct of TNFRI126-78 (L150V)

<400> SEQUENCE: 159

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Val Asn Gly
            100                 105                 110

Thr Val His Leu Ser Cys Gln Glu Lys Gln Asn Thr Val Cys
        115                 120                 125
```

<210> SEQ ID NO 160
<211> LENGTH: 126
<212> TYPE: PRT
<213> ORGANISM: Artificial Sequence
<220> FEATURE:
<223> OTHER INFORMATION: Synthetic construct of TNFRI126-79 (L156I)

<400> SEQUENCE: 160

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
```

100 105 110

Thr Val His Ile Ser Cys Gln Glu Lys Gln Asn Thr Val Cys
115 120 125

<210> SEQ ID NO 161
<211> LENGTH: 126
<212> TYPE: PRT
<213> ORGANISM: Artificial Sequence
<220> FEATURE:
<223> OTHER INFORMATION: Synthetic construct of TNFRI126-80 (L156V)

<400> SEQUENCE: 161

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Val Asn Cys Ser Leu Cys Leu Asn Gly
100 105 110

Thr Val His Val Ser Cys Gln Glu Lys Gln Asn Thr Val Cys
115 120 125

<210> SEQ ID NO 162
<211> LENGTH: 126
<212> TYPE: PRT
<213> ORGANISM: Artificial Sequence
<220> FEATURE:
<223> OTHER INFORMATION: Synthetic construct of TNFRI126-81 (E160Q)

<400> SEQUENCE: 162

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Ile Asn Cys Ser Leu Cys Leu Asn Gly
100 105 110

Thr Val His Leu Ser Cys Gln Gln Lys Gln Asn Thr Val Cys
115 120 125

<210> SEQ ID NO 163
<211> LENGTH: 126
<212> TYPE: PRT
<213> ORGANISM: Artificial Sequence
<220> FEATURE:

<223> OTHER INFORMATION: Synthetic construct of TNFRI126-82 (E160N)

<400> SEQUENCE: 163

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Asn Lys Gln Asn Thr Val Cys
        115                 120                 125
```

<210> SEQ ID NO 164
<211> LENGTH: 126
<212> TYPE: PRT
<213> ORGANISM: Artificial Sequence
<220> FEATURE:
<223> OTHER INFORMATION: Synthetic construct of TNFRI126-83 (K161Q)

<400> SEQUENCE: 164

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Glu Gln Gln Asn Thr Val Cys
        115                 120                 125
```

<210> SEQ ID NO 165
<211> LENGTH: 126
<212> TYPE: PRT
<213> ORGANISM: Artificial Sequence
<220> FEATURE:
<223> OTHER INFORMATION: Synthetic construct of TNFRI126-84 (K161N)

<400> SEQUENCE: 165

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
```

35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Val Asn Cys Ser Leu Cys Leu Asn Gly
100 105 110

Thr Val His Leu Ser Cys Gln Glu Asn Gln Asn Thr Val Cys
115 120 125

<210> SEQ ID NO 166
<211> LENGTH: 171
<212> TYPE: PRT
<213> ORGANISM: Artificial Sequence
<220> FEATURE:
<223> OTHER INFORMATION: Synthetic construct of TNFRI171-1 (K48Q)

<400> SEQUENCE: 166

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 167
<211> LENGTH: 171
<212> TYPE: PRT
<213> ORGANISM: Artificial Sequence
<220> FEATURE:
<223> OTHER INFORMATION: Synthetic construct of TNFRI171-2 (K48N)

<400> SEQUENCE: 167

Asp Ser Val Cys Pro Gln Gly Asn Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

-continued

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 168
<211> LENGTH: 171
<212> TYPE: PRT
<213> ORGANISM: Artificial Sequence
<220> FEATURE:
<223> OTHER INFORMATION: Synthetic construct of TNFRI171-3 (Y49I)

<400> SEQUENCE: 168

```
Asp Ser Val Cys Pro Gln Gly Lys Ile Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 169
<211> LENGTH: 171
<212> TYPE: PRT
<213> ORGANISM: Artificial Sequence
<220> FEATURE:
<223> OTHER INFORMATION: Synthetic construct of TNFRI171-4 (Y49H)

<400> SEQUENCE: 169

```
Asp Ser Val Cys Pro Gln Gly Lys His Ile His Pro Gln Asn Asn Ser
  1               5                  10                  15
```

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 170
<211> LENGTH: 171
<212> TYPE: PRT
<213> ORGANISM: Artificial Sequence
<220> FEATURE:
<223> OTHER INFORMATION: Synthetic construct of TNFRI171-5 (P52A)

<400> SEQUENCE: 170

Asp Ser Val Cys Pro Gln Gly Lys Tyr Ile His Ala Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 171
<211> LENGTH: 171
<212> TYPE: PRT
<213> ORGANISM: Artificial Sequence
```

-continued

<220> FEATURE:
<223> OTHER INFORMATION: Synthetic construct of TNFRI171-6 (P52S)

<400> SEQUENCE: 171

```
Asp Ser Val Cys Pro Gln Gly Lys Tyr Ile His Ser Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 172
<211> LENGTH: 171
<212> TYPE: PRT
<213> ORGANISM: Artificial Sequence
<220> FEATURE:
<223> OTHER INFORMATION: Synthetic construct of TNFRI171-7 (K61Q)

<400> SEQUENCE: 172

```
Asp Ser Val Cys Pro Gln Gly Lys Tyr Ile His Pro Gln Asn Asn Ser
  1               5                  10                  15

Ile Cys Cys Thr Gln Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
```

165 170

<210> SEQ ID NO 173
<211> LENGTH: 171
<212> TYPE: PRT
<213> ORGANISM: Artificial Sequence
<220> FEATURE:
<223> OTHER INFORMATION: Synthetic construct of TNFRI171-8 (K61N)

<400> SEQUENCE: 173

Asp Ser Val Cys Pro Gln Gly Lys Tyr Ile His Pro Gln Asn Asn Ser
1 5 10 15

Ile Cys Cys Thr Asn Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 174
<211> LENGTH: 171
<212> TYPE: PRT
<213> ORGANISM: Artificial Sequence
<220> FEATURE:
<223> OTHER INFORMATION: Synthetic construct of TNFRI171-9 (K64Q)

<400> SEQUENCE: 174

Asp Ser Val Cys Pro Gln Gly Lys Tyr Ile His Pro Gln Asn Asn Ser
1 5 10 15

Ile Cys Cys Thr Lys Cys His Gln Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

```
His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 175
<211> LENGTH: 171
<212> TYPE: PRT
<213> ORGANISM: Artificial Sequence
<220> FEATURE:
<223> OTHER INFORMATION: Synthetic construct of TNFRI171-10 (K64N)

<400> SEQUENCE: 175

Asp Ser Val Cys Pro Gln Gly Lys Tyr Ile His Pro Gln Asn Asn Ser
  1               5                  10                  15

Ile Cys Cys Thr Lys Cys His Asn Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 176
<211> LENGTH: 171
<212> TYPE: PRT
<213> ORGANISM: Artificial Sequence
<220> FEATURE:
<223> OTHER INFORMATION: Synthetic construct of TNFRI171-11 (Y67I)

<400> SEQUENCE: 176

Asp Ser Val Cys Pro Gln Gly Lys Tyr Ile His Pro Gln Asn Asn Ser
  1               5                  10                  15

Ile Cys Cys Thr Lys Cys His Lys Gly Thr Ile Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95
```

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 177
<211> LENGTH: 171
<212> TYPE: PRT
<213> ORGANISM: Artificial Sequence
<220> FEATURE:
<223> OTHER INFORMATION: Synthetic construct of TNFRI171-12 (Y67H)

<400> SEQUENCE: 177

Asp Ser Val Cys Pro Gln Gly Lys Tyr Ile His Pro Gln Asn Asn Ser
  1               5                  10                  15

Ile Cys Cys Thr Lys Cys His Lys Gly Thr His Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 178
<211> LENGTH: 171
<212> TYPE: PRT
<213> ORGANISM: Artificial Sequence
<220> FEATURE:
<223> OTHER INFORMATION: Synthetic construct of TNFRI171-13 (L68I)

<400> SEQUENCE: 178

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Ile Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
```

```
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 179
<211> LENGTH: 171
<212> TYPE: PRT
<213> ORGANISM: Artificial Sequence
<220> FEATURE:
<223> OTHER INFORMATION: Synthetic construct of TNFRI171-14 (L68V)

<400> SEQUENCE: 179

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 180
<211> LENGTH: 171
<212> TYPE: PRT
<213> ORGANISM: Artificial Sequence
<220> FEATURE:
<223> OTHER INFORMATION: Synthetic construct of TNFRI171-15 (Y69I)

<400> SEQUENCE: 180

Asp Ser Val Cys Pro Gln Gly Lys Tyr Ile His Pro Gln Asn Asn Ser
  1               5                  10                  15
```

```
Ile Cys Cys Thr Lys Cys His Lys Gly Thr Tyr Leu Ile Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 181
<211> LENGTH: 171
<212> TYPE: PRT
<213> ORGANISM: Artificial Sequence
<220> FEATURE:
<223> OTHER INFORMATION: Synthetic construct of TNFRI171-16 (Y69H)

<400> SEQUENCE: 181

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu His Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 182
<211> LENGTH: 171
<212> TYPE: PRT
<213> ORGANISM: Artificial Sequence
<220> FEATURE:
```

<223> OTHER INFORMATION: Synthetic construct of TNFRI171-17 (D71N)

<400> SEQUENCE: 182

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asn Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 183
<211> LENGTH: 171
<212> TYPE: PRT
<213> ORGANISM: Artificial Sequence
<220> FEATURE:
<223> OTHER INFORMATION: Synthetic construct of TNFRI171-18 (D71Q)

<400> SEQUENCE: 183

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Gln Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 184
<211> LENGTH: 171
<212> TYPE: PRT
<213> ORGANISM: Artificial Sequence
<220> FEATURE:
<223> OTHER INFORMATION: Synthetic construct of TNFRI171-19 (D78N)

<400> SEQUENCE: 184

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asn Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 185
<211> LENGTH: 171
<212> TYPE: PRT
<213> ORGANISM: Artificial Sequence
<220> FEATURE:
<223> OTHER INFORMATION: Synthetic construct of TNFRI171-20 (D78Q)

<400> SEQUENCE: 185

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Gln Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
```

```
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 186
<211> LENGTH: 171
<212> TYPE: PRT
<213> ORGANISM: Artificial Sequence
<220> FEATURE:
<223> OTHER INFORMATION: Synthetic construct of TNFRI171-21 (D80N)

<400> SEQUENCE: 186

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asn Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 187
<211> LENGTH: 171
<212> TYPE: PRT
<213> ORGANISM: Artificial Sequence
<220> FEATURE:
<223> OTHER INFORMATION: Synthetic construct of TNFRI171-22 (D80Q)

<400> SEQUENCE: 187

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Gln Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95
```

-continued

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 188
<211> LENGTH: 171
<212> TYPE: PRT
<213> ORGANISM: Artificial Sequence
<220> FEATURE:
<223> OTHER INFORMATION: Synthetic construct of TNFRI171-23 (R82H)

<400> SEQUENCE: 188

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys His Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 189
<211> LENGTH: 171
<212> TYPE: PRT
<213> ORGANISM: Artificial Sequence
<220> FEATURE:
<223> OTHER INFORMATION: Synthetic construct of TNFRI171-24 (R82Q)

<400> SEQUENCE: 189

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Gln Glu Cys Glu Ser Gly Ser
        35                  40                  45

Phe Thr Ala Ser Glu Asn His Leu Arg His Cys Leu Ser Cys Ser Lys
     50                  55                  60
```

```
Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 190
<211> LENGTH: 171
<212> TYPE: PRT
<213> ORGANISM: Artificial Sequence
<220> FEATURE:
<223> OTHER INFORMATION: Synthetic construct of TNFRI171-25 (E83Q)

<400> SEQUENCE: 190

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Gln Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 191
<211> LENGTH: 171
<212> TYPE: PRT
<213> ORGANISM: Artificial Sequence
<220> FEATURE:
<223> OTHER INFORMATION: Synthetic construct of TNFRI171-26 (E83N)

<400> SEQUENCE: 191

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
```

```
            20                  25                  30

Pro Gly Pro Gly Gln Asp Thr Asp Cys Arg Asn Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 192
<211> LENGTH: 171
<212> TYPE: PRT
<213> ORGANISM: Artificial Sequence
<220> FEATURE:
<223> OTHER INFORMATION: Synthetic construct of TNFRI171-27 (E85Q)

<400> SEQUENCE: 192

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Gln Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 193
<211> LENGTH: 171
<212> TYPE: PRT
<213> ORGANISM: Artificial Sequence
<220> FEATURE:
<223> OTHER INFORMATION: Synthetic construct of TNFRI171-28 (E85N)
```

-continued

<400> SEQUENCE: 193

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Asn Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 194
<211> LENGTH: 171
<212> TYPE: PRT
<213> ORGANISM: Artificial Sequence
<220> FEATURE:
<223> OTHER INFORMATION: Synthetic construct of TNFRI171-29 (F89I)

<400> SEQUENCE: 194

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Ile Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 195
<211> LENGTH: 171
<212> TYPE: PRT
<213> ORGANISM: Artificial Sequence
<220> FEATURE:
<223> OTHER INFORMATION: Synthetic construct of TNFRI171-30 (F89V)

<400> SEQUENCE: 195

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Val Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 196
<211> LENGTH: 171
<212> TYPE: PRT
<213> ORGANISM: Artificial Sequence
<220> FEATURE:
<223> OTHER INFORMATION: Synthetic construct of TNFRI171-31 (E93Q)

<400> SEQUENCE: 196

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Gln Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140
```

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 197
<211> LENGTH: 171
<212> TYPE: PRT
<213> ORGANISM: Artificial Sequence
<220> FEATURE:
<223> OTHER INFORMATION: Synthetic construct of TNFRI171-32 (E93N)

<400> SEQUENCE: 197

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Asn Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 198
<211> LENGTH: 171
<212> TYPE: PRT
<213> ORGANISM: Artificial Sequence
<220> FEATURE:
<223> OTHER INFORMATION: Synthetic construct of TNFRI171-33 (L96I)

<400> SEQUENCE: 198

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Ile Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly

-continued

```
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 199
<211> LENGTH: 171
<212> TYPE: PRT
<213> ORGANISM: Artificial Sequence
<220> FEATURE:
<223> OTHER INFORMATION: Synthetic construct of TNFRI171-34 (L96V)

<400> SEQUENCE: 199

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Val Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 200
<211> LENGTH: 171
<212> TYPE: PRT
<213> ORGANISM: Artificial Sequence
<220> FEATURE:
<223> OTHER INFORMATION: Synthetic construct of TNFRI171-35 (R97H)

<400> SEQUENCE: 200

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu His His Cys Leu Ser Cys Ser Lys
     50                  55                  60
```

-continued

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 201
<211> LENGTH: 170
<212> TYPE: PRT
<213> ORGANISM: Artificial Sequence
<220> FEATURE:
<223> OTHER INFORMATION: Synthetic construct of TNFRI171-36 (R97Q)

<400> SEQUENCE: 201

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Gln His Cys Leu Cys Ser Lys Cys
50 55 60

Arg Lys Glu Met Gly Gln Val Glu Ile Ser Ser Cys Thr Val Asp Arg
65 70 75 80

Asp Thr Val Cys Gly Cys Arg Lys Asn Gln Tyr Arg His Tyr Trp Ser
85 90 95

Glu Asn Leu Phe Gln Cys Phe Asn Cys Ser Leu Cys Leu Asn Gly Thr
100 105 110

Val His Leu Ser Cys Gln Glu Lys Gln Asn Thr Val Cys Thr Cys His
115 120 125

Ala Gly Phe Phe Leu Arg Glu Asn Glu Cys Val Ser Cys Ser Asn Cys
130 135 140

Lys Lys Ser Leu Glu Cys Thr Lys Leu Cys Leu Pro Gln Ile Glu Asn
145 150 155 160

Val Lys Gly Thr Glu Asp Ser Gly Thr Thr
165 170

<210> SEQ ID NO 202
<211> LENGTH: 171
<212> TYPE: PRT
<213> ORGANISM: Artificial Sequence
<220> FEATURE:
<223> OTHER INFORMATION: Synthetic construct of TNFRI171-37 (L100I)

<400> SEQUENCE: 202

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Ile Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 203
<211> LENGTH: 171
<212> TYPE: PRT
<213> ORGANISM: Artificial Sequence
<220> FEATURE:
<223> OTHER INFORMATION: Synthetic construct of TNFRI171-38 (L100V)

<400> SEQUENCE: 203

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Val Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 204
<211> LENGTH: 171
<212> TYPE: PRT
<213> ORGANISM: Artificial Sequence
<220> FEATURE:
<223> OTHER INFORMATION: Synthetic construct of TNFRI171-39 (K104Q)

<400> SEQUENCE: 204

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Gln
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 205
<211> LENGTH: 171
<212> TYPE: PRT
<213> ORGANISM: Artificial Sequence
<220> FEATURE:
<223> OTHER INFORMATION: Synthetic construct of TNFRI171-40 (K104N)

<400> SEQUENCE: 205

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Asn
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

```
<210> SEQ ID NO 206
<211> LENGTH: 171
<212> TYPE: PRT
<213> ORGANISM: Artificial Sequence
<220> FEATURE:
<223> OTHER INFORMATION: Synthetic construct of TNFRI171-41 (R106H)

<400> SEQUENCE: 206

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys His Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 207
<211> LENGTH: 171
<212> TYPE: PRT
<213> ORGANISM: Artificial Sequence
<220> FEATURE:
<223> OTHER INFORMATION: Synthetic construct of TNFRI171-42 (R106Q)

<400> SEQUENCE: 207

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Gln Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140
```

```
Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 208
<211> LENGTH: 171
<212> TYPE: PRT
<213> ORGANISM: Artificial Sequence
<220> FEATURE:
<223> OTHER INFORMATION: Synthetic construct of TNFRI171-43 (K107Q)

<400> SEQUENCE: 208

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Gln Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 209
<211> LENGTH: 171
<212> TYPE: PRT
<213> ORGANISM: Artificial Sequence
<220> FEATURE:
<223> OTHER INFORMATION: Synthetic construct of TNFRI171-44 (K107N)

<400> SEQUENCE: 209

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Asn Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110
```

```
Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 210
<211> LENGTH: 171
<212> TYPE: PRT
<213> ORGANISM: Artificial Sequence
<220> FEATURE:
<223> OTHER INFORMATION: Synthetic construct of TNFRI171-45 (E108Q)

<400> SEQUENCE: 210

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Gln Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 211
<211> LENGTH: 171
<212> TYPE: PRT
<213> ORGANISM: Artificial Sequence
<220> FEATURE:
<223> OTHER INFORMATION: Synthetic construct of TNFRI171-46 (E108N)

<400> SEQUENCE: 211

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Asn Met Gly Gln Val Glu Ile Ser Ser Cys Thr Val Asp
```

65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 212
<211> LENGTH: 171
<212> TYPE: PRT
<213> ORGANISM: Artificial Sequence
<220> FEATURE:
<223> OTHER INFORMATION: Synthetic construct of TNFRI171-47 (M109I)

<400> SEQUENCE: 212

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Ile Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 213
<211> LENGTH: 171
<212> TYPE: PRT
<213> ORGANISM: Artificial Sequence
<220> FEATURE:
<223> OTHER INFORMATION: Synthetic construct of TNFRI171-48 (M109V)

<400> SEQUENCE: 213

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Val Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 214
<211> LENGTH: 171
<212> TYPE: PRT
<213> ORGANISM: Artificial Sequence
<220> FEATURE:
<223> OTHER INFORMATION: Synthetic construct of TNFRI171-49 (E113Q)

<400> SEQUENCE: 214

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Gln Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 215
<211> LENGTH: 171
<212> TYPE: PRT
<213> ORGANISM: Artificial Sequence
<220> FEATURE:
<223> OTHER INFORMATION: Synthetic construct of TNFRI171-50 (E113N)

<400> SEQUENCE: 215

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Asn Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 216
<211> LENGTH: 171
<212> TYPE: PRT
<213> ORGANISM: Artificial Sequence
<220> FEATURE:
<223> OTHER INFORMATION: Synthetic construct of TNFRI171-51 (D120N)

<400> SEQUENCE: 216

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asn
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 217
```

```
<211> LENGTH: 171
<212> TYPE: PRT
<213> ORGANISM: Artificial Sequence
<220> FEATURE:
<223> OTHER INFORMATION: Synthetic construct of TNFRI171-52 (D120Q)

<400> SEQUENCE: 217

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Gln
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 218
<211> LENGTH: 171
<212> TYPE: PRT
<213> ORGANISM: Artificial Sequence
<220> FEATURE:
<223> OTHER INFORMATION: Synthetic construct of TNFRI171-53 (R121H)

<400> SEQUENCE: 218

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

His Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
```

```
145                 150                 155                 160

Asn Val Lys Gly Thr Glu Asp Ser Gly Thr Thr
                165                 170


<210> SEQ ID NO 219
<211> LENGTH: 171
<212> TYPE: PRT
<213> ORGANISM: Artificial Sequence
<220> FEATURE:
<223> OTHER INFORMATION: Synthetic construct of TNFRI171-54 (R121Q)

<400> SEQUENCE: 219

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Gln Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 220
<211> LENGTH: 171
<212> TYPE: PRT
<213> ORGANISM: Artificial Sequence
<220> FEATURE:
<223> OTHER INFORMATION: Synthetic construct of TNFRI171-55 (D122N)

<400> SEQUENCE: 220

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asn Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110
```

```
Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 221
<211> LENGTH: 171
<212> TYPE: PRT
<213> ORGANISM: Artificial Sequence
<220> FEATURE:
<223> OTHER INFORMATION: Synthetic construct of TNFRI171-56 (D122Q)

<400> SEQUENCE: 221

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Gln Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 222
<211> LENGTH: 171
<212> TYPE: PRT
<213> ORGANISM: Artificial Sequence
<220> FEATURE:
<223> OTHER INFORMATION: Synthetic construct of TNFRI171-57 (R128H)

<400> SEQUENCE: 222

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80
```

```
Arg Asp Thr Val Cys Gly Cys His Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 223
<211> LENGTH: 171
<212> TYPE: PRT
<213> ORGANISM: Artificial Sequence
<220> FEATURE:
<223> OTHER INFORMATION: Synthetic construct of TNFRI171-58 (R128Q)

<400> SEQUENCE: 223

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Gln Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 224
<211> LENGTH: 171
<212> TYPE: PRT
<213> ORGANISM: Artificial Sequence
<220> FEATURE:
<223> OTHER INFORMATION: Synthetic construct of TNFRI171-59 (K129Q)

<400> SEQUENCE: 224

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
```

35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Gln Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 225
<211> LENGTH: 171
<212> TYPE: PRT
<213> ORGANISM: Artificial Sequence
<220> FEATURE:
<223> OTHER INFORMATION: Synthetic construct of TNFRI171-60 (K129N)

<400> SEQUENCE: 225

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Asn Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 226
<211> LENGTH: 171
<212> TYPE: PRT
<213> ORGANISM: Artificial Sequence
<220> FEATURE:
<223> OTHER INFORMATION: Synthetic construct of TNFRI171-61 (Y132I)

<400> SEQUENCE: 226

-continued

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Ile Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 227
<211> LENGTH: 171
<212> TYPE: PRT
<213> ORGANISM: Artificial Sequence
<220> FEATURE:
<223> OTHER INFORMATION: Synthetic construct of TNFRI171-62 (Y132H)

<400> SEQUENCE: 227

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln His Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 228
<211> LENGTH: 171
```

<212> TYPE: PRT
<213> ORGANISM: Artificial Sequence
<220> FEATURE:
<223> OTHER INFORMATION: Synthetic construct of TNFRI171-63 (R133H)

<400> SEQUENCE: 228

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr His His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 229
<211> LENGTH: 171
<212> TYPE: PRT
<213> ORGANISM: Artificial Sequence
<220> FEATURE:
<223> OTHER INFORMATION: Synthetic construct of TNFRI171-64 (R133Q)

<400> SEQUENCE: 229

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Gln His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160
```

```
Asn Val Lys Gly Thr Glu Asp Ser Gly Thr Thr
                165                 170


<210> SEQ ID NO 230
<211> LENGTH: 171
<212> TYPE: PRT
<213> ORGANISM: Artificial Sequence
<220> FEATURE:
<223> OTHER INFORMATION: Synthetic construct of TNFRI171-65 (Y135I)

<400> SEQUENCE: 230

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Ile Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 231
<211> LENGTH: 171
<212> TYPE: PRT
<213> ORGANISM: Artificial Sequence
<220> FEATURE:
<223> OTHER INFORMATION: Synthetic construct of TNFRI171-66 (Y135H)

<400> SEQUENCE: 231

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His His Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
```

```
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 232
<211> LENGTH: 171
<212> TYPE: PRT
<213> ORGANISM: Artificial Sequence
<220> FEATURE:
<223> OTHER INFORMATION: Synthetic construct of TNFRI171-67 (W136H)

<400> SEQUENCE: 232

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr His
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 233
<211> LENGTH: 171
<212> TYPE: PRT
<213> ORGANISM: Artificial Sequence
<220> FEATURE:
<223> OTHER INFORMATION: Synthetic construct of TNFRI171-68 (W136S)

<400> SEQUENCE: 233

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80
```

```
Arg Asp Thr Val Cys Gly Cys Arg Lys Asn Gln Tyr Arg His Tyr Ser
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 234
<211> LENGTH: 171
<212> TYPE: PRT
<213> ORGANISM: Artificial Sequence
<220> FEATURE:
<223> OTHER INFORMATION: Synthetic construct of TNFRI171-69 (E138Q)

<400> SEQUENCE: 234

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Gln Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 235
<211> LENGTH: 171
<212> TYPE: PRT
<213> ORGANISM: Artificial Sequence
<220> FEATURE:
<223> OTHER INFORMATION: Synthetic construct of TNFRI171-70 (E138N)

<400> SEQUENCE: 235

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45
```

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Asn Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 236
<211> LENGTH: 171
<212> TYPE: PRT
<213> ORGANISM: Artificial Sequence
<220> FEATURE:
<223> OTHER INFORMATION: Synthetic construct of TNFRI171-71 (L140I)

<400> SEQUENCE: 236

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Ile Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 237
<211> LENGTH: 171
<212> TYPE: PRT
<213> ORGANISM: Artificial Sequence
<220> FEATURE:
<223> OTHER INFORMATION: Synthetic construct of TNFRI171-72 (L140V)

<400> SEQUENCE: 237

Asp Ser Val Cys Pro Gln Gly Lys Tyr Ile His Pro Gln Asn Asn Ser
```

-continued

```
  1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Val Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 238
<211> LENGTH: 171
<212> TYPE: PRT
<213> ORGANISM: Artificial Sequence
<220> FEATURE:
<223> OTHER INFORMATION: Synthetic construct of TNFRI171-73 (F141I)

<400> SEQUENCE: 238

```
Asp Ser Val Cys Pro Gln Gly Lys Tyr Ile His Pro Gln Asn Asn Ser
  1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Ile Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 239
<211> LENGTH: 171
<212> TYPE: PRT

```
<213> ORGANISM: Artificial Sequence
<220> FEATURE:
<223> OTHER INFORMATION: Synthetic construct of TNFRI171-74 (F141V)

<400> SEQUENCE: 239

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Val Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 240
<211> LENGTH: 171
<212> TYPE: PRT
<213> ORGANISM: Artificial Sequence
<220> FEATURE:
<223> OTHER INFORMATION: Synthetic construct of TNFRI171-75 (F144I)

<400> SEQUENCE: 240

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160
```

-continued

```
Asn Val Lys Gly Thr Glu Asp Ser Gly Thr Thr
                165                 170


<210> SEQ ID NO 241
<211> LENGTH: 171
<212> TYPE: PRT
<213> ORGANISM: Artificial Sequence
<220> FEATURE:
<223> OTHER INFORMATION: Synthetic construct of TNFRI171-76 (F144V)

<400> SEQUENCE: 241

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 242
<211> LENGTH: 171
<212> TYPE: PRT
<213> ORGANISM: Artificial Sequence
<220> FEATURE:
<223> OTHER INFORMATION: Synthetic construct of TNFRI171-77 (L150I)

<400> SEQUENCE: 242

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Ile Asn Cys Ser Leu Cys Ile Asn Gly
            100                 105                 110

Thr Val His Leu Ser Cys Gln Glu Lys Gln Asn Thr Val Cys Thr Cys
        115                 120                 125
```

```
His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 243
<211> LENGTH: 171
<212> TYPE: PRT
<213> ORGANISM: Artificial Sequence
<220> FEATURE:
<223> OTHER INFORMATION: Synthetic construct of TNFRI171-78 (L150V)

<400> SEQUENCE: 243

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Val Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 244
<211> LENGTH: 171
<212> TYPE: PRT
<213> ORGANISM: Artificial Sequence
<220> FEATURE:
<223> OTHER INFORMATION: Synthetic construct of TNFRI171-79 (L156I)

<400> SEQUENCE: 244

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
```

```
                85                  90                  95

Ser Glu Asn Leu Phe Gln Cys Ile Asn Cys Ser Leu Cys Leu Asn Gly
            100                 105                 110

Thr Val His Ile Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 245
<211> LENGTH: 171
<212> TYPE: PRT
<213> ORGANISM: Artificial Sequence
<220> FEATURE:
<223> OTHER INFORMATION: Synthetic construct of TNFRI171-80 (L156V)

<400> SEQUENCE: 245

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Val Asn Cys Ser Leu Cys Leu Asn Gly
            100                 105                 110

Thr Val His Val Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 246
<211> LENGTH: 171
<212> TYPE: PRT
<213> ORGANISM: Artificial Sequence
<220> FEATURE:
<223> OTHER INFORMATION: Synthetic construct of TNFRI171-81 (E160Q)

<400> SEQUENCE: 246

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Gln Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 247
<211> LENGTH: 171
<212> TYPE: PRT
<213> ORGANISM: Artificial Sequence
<220> FEATURE:
<223> OTHER INFORMATION: Synthetic construct of TNFRI171-82 (E160N)

<400> SEQUENCE: 247

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Asn Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 248
<211> LENGTH: 171
<212> TYPE: PRT
<213> ORGANISM: Artificial Sequence
<220> FEATURE:
<223> OTHER INFORMATION: Synthetic construct of TNFRI171-83 (K161Q)

<400> SEQUENCE: 248

Asp Ser Val Cys Pro Gln Gly Lys Tyr Ile His Pro Gln Asn Asn Ser
  1               5                  10                  15
```

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Ile Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 249
<211> LENGTH: 171
<212> TYPE: PRT
<213> ORGANISM: Artificial Sequence
<220> FEATURE:
<223> OTHER INFORMATION: Synthetic construct of TNFRI171-84 (K161N)

<400> SEQUENCE: 249

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Val Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 250
<211> LENGTH: 171
<212> TYPE: PRT
<213> ORGANISM: Artificial Sequence
```

```
<220> FEATURE:
<223> OTHER INFORMATION: Synthetic construct of TNFRI171-85 (E200Q)

<400> SEQUENCE: 250

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
                165                 170


<210> SEQ ID NO 251
<211> LENGTH: 171
<212> TYPE: PRT
<213> ORGANISM: Artificial Sequence
<220> FEATURE:
<223> OTHER INFORMATION: Synthetic construct of TNFRI171-86 (E200N)

<400> SEQUENCE: 251

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Asn
145                 150                 155                 160

Asn Val Lys Gly Thr Glu Asp Ser Gly Thr Thr
```

165 170

<210> SEQ ID NO 252
<211> LENGTH: 171
<212> TYPE: PRT
<213> ORGANISM: Artificial Sequence
<220> FEATURE:
<223> OTHER INFORMATION: Synthetic construct of TNFRI171-87 (K203Q)

<400> SEQUENCE: 252

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Ile Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 253
<211> LENGTH: 171
<212> TYPE: PRT
<213> ORGANISM: Artificial Sequence
<220> FEATURE:
<223> OTHER INFORMATION: Synthetic construct of TNFRI171-88 (K203N)

<400> SEQUENCE: 253

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Val Asn Cys Ser Leu Cys Leu Asn Gly
100 105 110

Thr Val His Leu Ser Cys Gln Glu Lys Gln Asn Thr Val Cys Thr Cys
115 120 125

```
His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Asn Gly Thr Glu Asp Ser Gly Thr Thr
                165                 170


<210> SEQ ID NO 254
<211> LENGTH: 171
<212> TYPE: PRT
<213> ORGANISM: Artificial Sequence
<220> FEATURE:
<223> OTHER INFORMATION: Synthetic construct of TNFRI171-89 (E206Q)

<400> SEQUENCE: 254

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Gln Asp Ser Gly Thr Thr
                165                 170


<210> SEQ ID NO 255
<211> LENGTH: 171
<212> TYPE: PRT
<213> ORGANISM: Artificial Sequence
<220> FEATURE:
<223> OTHER INFORMATION: Synthetic construct of TNFRI171-90 (E206N)

<400> SEQUENCE: 255

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95
```

```
Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Asn Asp Ser Gly Thr Thr
                165                 170


<210> SEQ ID NO 256
<211> LENGTH: 171
<212> TYPE: PRT
<213> ORGANISM: Artificial Sequence
<220> FEATURE:
<223> OTHER INFORMATION: Synthetic construct of TNFRI171-91 (D207Q)

<400> SEQUENCE: 256

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Ile Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Gln Ser Gly Thr Thr
                165                 170


<210> SEQ ID NO 257
<211> LENGTH: 171
<212> TYPE: PRT
<213> ORGANISM: Artificial Sequence
<220> FEATURE:
<223> OTHER INFORMATION: Synthetic construct of TNFRI171-92 (D207N)

<400> SEQUENCE: 257

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
```

```
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 258
<211> LENGTH: 171
<212> TYPE: PRT
<213> ORGANISM: Artificial Sequence
<220> FEATURE:
<223> OTHER INFORMATION: Synthetic construct of TNFRI171-201
      (L68V/R133Q)

<400> SEQUENCE: 258

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Gln His Tyr Trp
                85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 259
<211> LENGTH: 171
<212> TYPE: PRT
<213> ORGANISM: Artificial Sequence
<220> FEATURE:
<223> OTHER INFORMATION: Synthetic construct of TNFRI171-202
      (L68V/F141V)

<400> SEQUENCE: 259

Asp Ser Val Cys Pro Gln Gly Lys Tyr Ile His Pro Gln Asn Asn Ser
```

-continued

```
  1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Val Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 260
<211> LENGTH: 171
<212> TYPE: PRT
<213> ORGANISM: Artificial Sequence
<220> FEATURE:
<223> OTHER INFORMATION: Synthetic construct of TNFRI171-203 (R133Q/F141V)

<400> SEQUENCE: 260

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Gln His Tyr Trp
                 85                  90                  95

Ser Glu Asn Leu Val Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 261
<211> LENGTH: 171

<212> TYPE: PRT
<213> ORGANISM: Artificial Sequence
<220> FEATURE:
<223> OTHER INFORMATION: Synthetic construct of TNFRI171-204
(L68V/K161Q)

<400> SEQUENCE: 261

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 262
<211> LENGTH: 171
<212> TYPE: PRT
<213> ORGANISM: Artificial Sequence
<220> FEATURE:
<223> OTHER INFORMATION: Synthetic construct of TNFRI171-205
(L68V/K161N)

<400> SEQUENCE: 262

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140
```

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 263
<211> LENGTH: 171
<212> TYPE: PRT
<213> ORGANISM: Artificial Sequence
<220> FEATURE:
<223> OTHER INFORMATION: Synthetic construct of TNFRI171-206
(L68V/D207N)

<400> SEQUENCE: 263

Asp Ser Val Cys Pro Gln Gly Lys Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Val Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asn Ser Gly Thr Thr
165 170

<210> SEQ ID NO 264
<211> LENGTH: 171
<212> TYPE: PRT
<213> ORGANISM: Artificial Sequence
<220> FEATURE:
<223> OTHER INFORMATION: Synthetic construct of TNFRI171-207
(K161Q/D207N)

<400> SEQUENCE: 264

Asp Ser Val Cys Pro Gln Gly Lys Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

```
Ser Glu Asn Leu Phe Gln Cys Val Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 265
<211> LENGTH: 171
<212> TYPE: PRT
<213> ORGANISM: Artificial Sequence
<220> FEATURE:
<223> OTHER INFORMATION: Synthetic construct of TNFRI171-208
      (L68V/E200Q)

<400> SEQUENCE: 265

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Val Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
                165                 170


<210> SEQ ID NO 266
<211> LENGTH: 171
<212> TYPE: PRT
<213> ORGANISM: Artificial Sequence
<220> FEATURE:
<223> OTHER INFORMATION: Synthetic construct of TNFRI171-209
      (E200Q/D207N)

<400> SEQUENCE: 266

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45
```

-continued

```
Phe Thr Ala Ser Glu Asn His Leu Arg His Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Val Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asn Ser Gly Thr Thr
                165                 170
```

<210> SEQ ID NO 267
<211> LENGTH: 519
<212> TYPE: DNA
<213> ORGANISM: Artificial Sequence
<220> FEATURE:
<223> OTHER INFORMATION: Synthetic construct of Met-TNFRI171 nucleic acid sequence for bacterial expression

<400> SEQUENCE: 267

```
atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300

ctgttccagt gttttaattg ctccctgtgt ctgaacggca ctgtgcatct gtcctgtcag    360

gagaagcaga atacagtttg tacctgccat gcaggtttct ttctaagaga aaacgagtgt    420

gtctcctgta gtaactgtaa gaaaagcctg gagtgcacga agttgtgcct accccagatt    480

gagaatgtta agggcactga ggactcaggc accacataa                           519
```

<210> SEQ ID NO 268
<211> LENGTH: 384
<212> TYPE: DNA
<213> ORGANISM: Artificial Sequence
<220> FEATURE:
<223> OTHER INFORMATION: Synthetic construct of Met-TNFRI126 nucleic acid sequence for bacterial expression

<400> SEQUENCE: 268

```
atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300

ctgttccagt gttttaattg ctccctgtgt ctgaacggca ctgtgcatct gtcctgtcag    360

gagaagcaga atacagtttg ttaa                                           384
```

-continued

```
<210> SEQ ID NO 269
<211> LENGTH: 330
<212> TYPE: DNA
<213> ORGANISM: Artificial Sequence
<220> FEATURE:
<223> OTHER INFORMATION: Synthetic construct of Met-TNFRI108 nucleic
      acid sequence for bacterial expression

<400> SEQUENCE: 269

atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300

ctgttccagt gttttaattg ctccctgtaa                                     330
```